(12) United States Patent
Kawakami et al.

(10) Patent No.: US 7,411,677 B2
(45) Date of Patent: Aug. 12, 2008

(54) DRIVERLESS ELLIPSOMETER AND ELLIPSOMETRY

(75) Inventors: Shojiro Kawakami, Sendai (JP); Takashi Sato, Sendai (JP); Naoki Hashimoto, Sendai (JP); Yoshihiro Sasaki, Miyagi (JP)

(73) Assignees: Photonic Lattice Inc., Miyagi (JP); Japan Science and Technology Agency, Saitama (JP)

( * ) Notice: Subject to any disclaimer, the term of this patent is extended or adjusted under 35 U.S.C. 154(b) by 0 days.

(21) Appl. No.: 10/572,285

(22) PCT Filed: Jan. 23, 2004

(86) PCT No.: PCT/JP2004/000633

§ 371 (c)(1),
(2), (4) Date: Apr. 13, 2007

(87) PCT Pub. No.: WO2005/029050

PCT Pub. Date: Mar. 31, 2005

(65) Prior Publication Data

US 2007/0268490 A1 Nov. 22, 2007

(30) Foreign Application Priority Data

| Sep. 17, 2003 | (JP) | ............................. 2003-363854 |
| Dec. 5, 2003 | (JP) | ............................. 2003-407485 |
| Dec. 10, 2003 | (JP) | ............................. 2003-411786 |

(51) Int. Cl.
  *G01J 4/00* (2006.01)
(52) U.S. Cl. ....................... 356/365; 356/364; 356/369
(58) Field of Classification Search ................. 356/364, 356/365, 369
See application file for complete search history.

(56) References Cited

U.S. PATENT DOCUMENTS 4,158,506 A * 6/1979 Collett ....................... 356/365

(Continued)

FOREIGN PATENT DOCUMENTS

| JP | 4-147040 | 5/1992 |
| JP | 2002-116085 | 4/2002 |

OTHER PUBLICATIONS

International Search Report of PCT/JP2004/000633 dated Apr. 20, 2004.

*Primary Examiner*—Roy M Punnoose
(74) *Attorney, Agent, or Firm*—Westerman, Hattori, Daniels & Adrian, LLP.

(57) ABSTRACT

A small and high-speed polarization analysis device and ellipsometer having no driving section are provided by overlapping one polarizer array rendered by arranging a plurality of polarizer regions of mutually different optical axis directions in the form of stripes and one wavelength plate array rendered by arranging a plurality of wavelength plate regions of fixed retardation and mutually different optical axis directions in the form of stripes so that the respective stripes of the plurality of polarizer regions and of the plurality of wavelength plate regions intersect one another and by disposing a light-receiving element array so that the intensities of light that has passed through the matrix-like intersection parts can be individually measured. As a method of analyzing a two-dimensional intensity distribution pattern that is observed by the light-receiving element array of the polarization analysis device, either one of (or both of) the algorithms of a method that determines incident polarized waves by mathematically fitting pattern shapes or performing database matching or a method that performs a Fourier transform on pattern shapes and determines incident polarized waves from the frequency components is (are) used. Furthermore, if necessary, more accurate polarization analysis is also possible by adopting a signal processing method that removes signals from light-receiving element regions that receive unnecessary scattered light and diffracted light.

24 Claims, 38 Drawing Sheets

U.S. PATENT DOCUMENTS

| | | | |
|---|---|---|---|
| 5,327,285 A | * | 7/1994 | Faris .......................... 359/483 |
| 5,416,324 A | * | 5/1995 | Chun ....................... 250/341.3 |
| 5,479,015 A | * | 12/1995 | Rudman et al. ............. 250/332 |
| 6,075,235 A | | 6/2000 | Chun |

* cited by examiner

FIG. 8
INCIDENT POLARIZED WAVE ↔
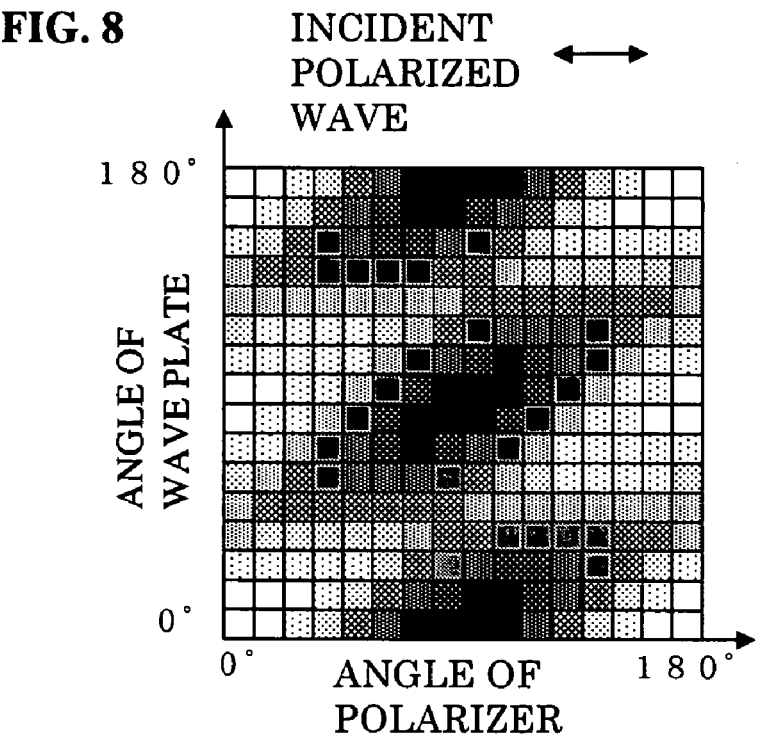
POLARIZER - WAVE PLATE
16 × 16 PARTITIONS
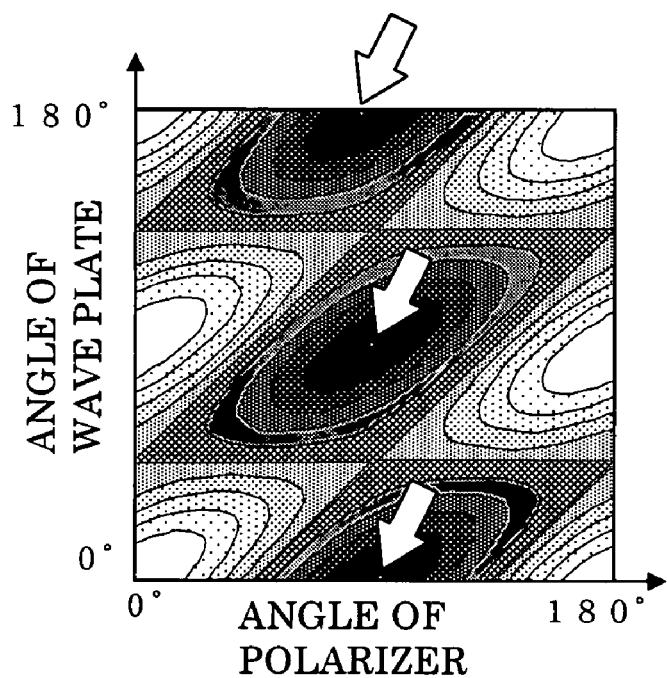
POLARIZER - WAVE PLATE
181 × 181 PARTITIONS
0 — 1

FIG. 12
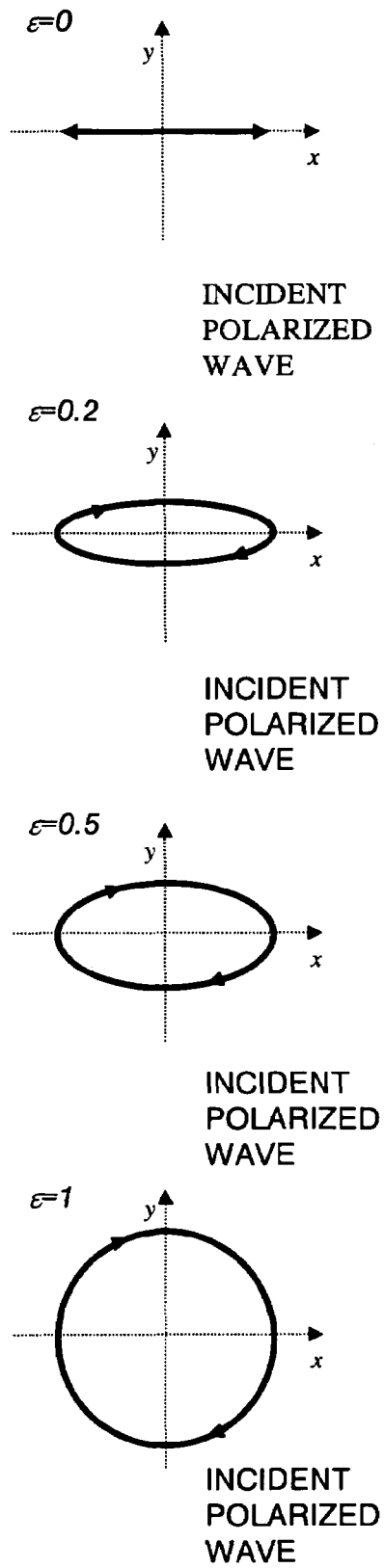
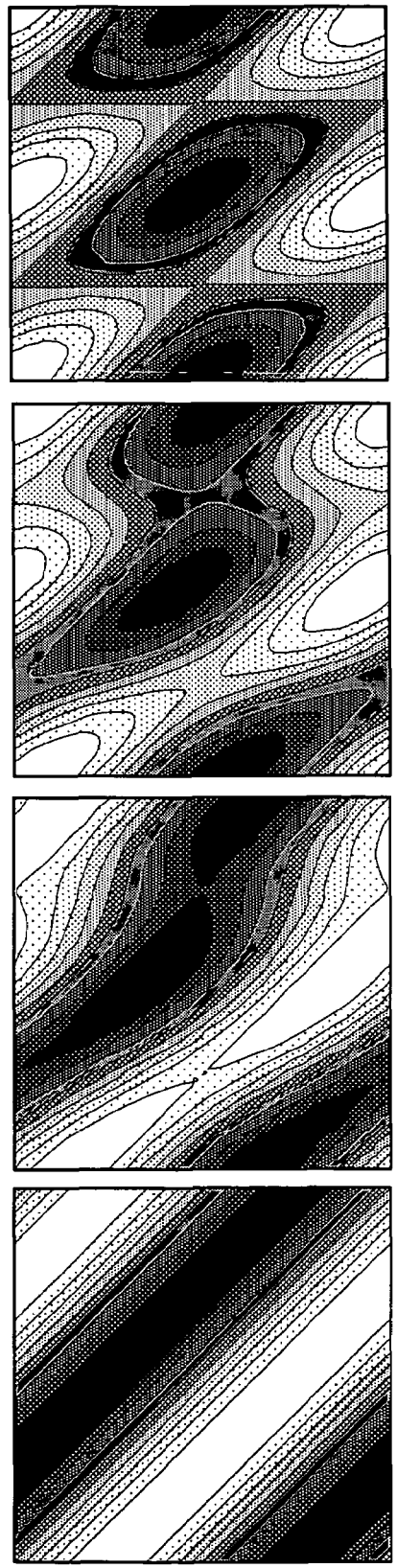

FIG. 16
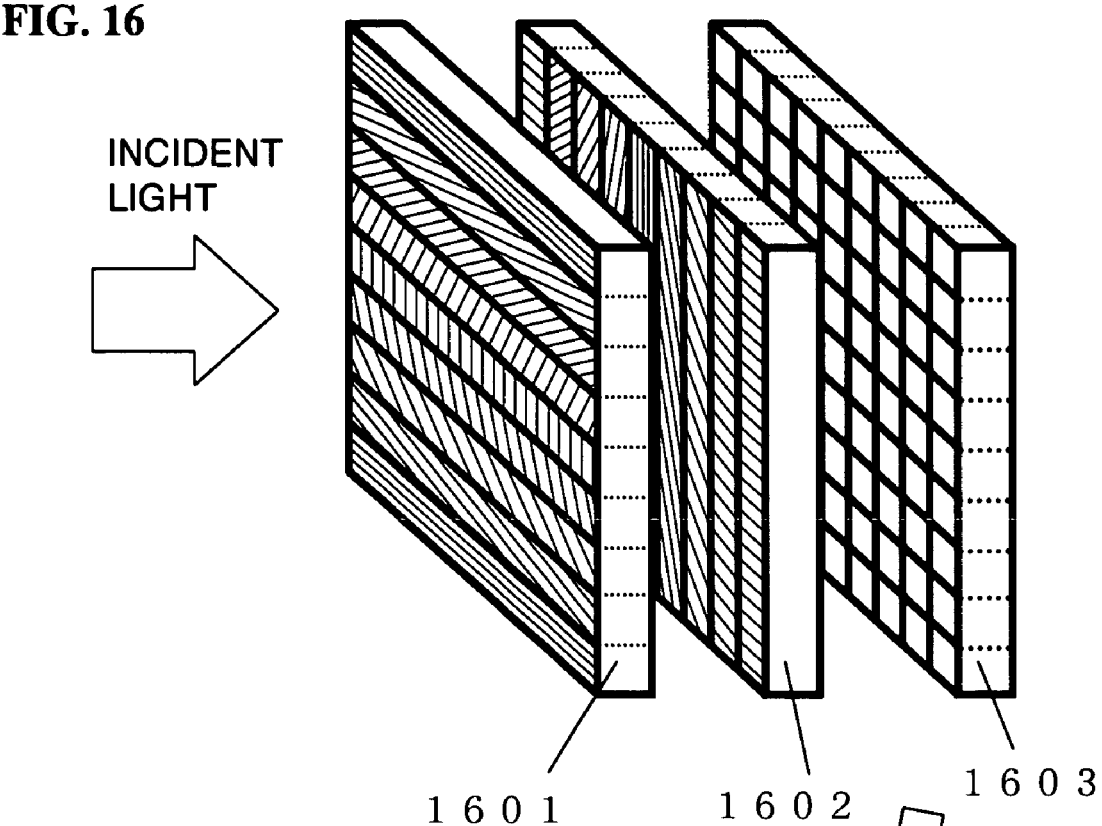
INCIDENT LIGHT
1 6 0 1    1 6 0 2    1 6 0 3
FIG. 16A
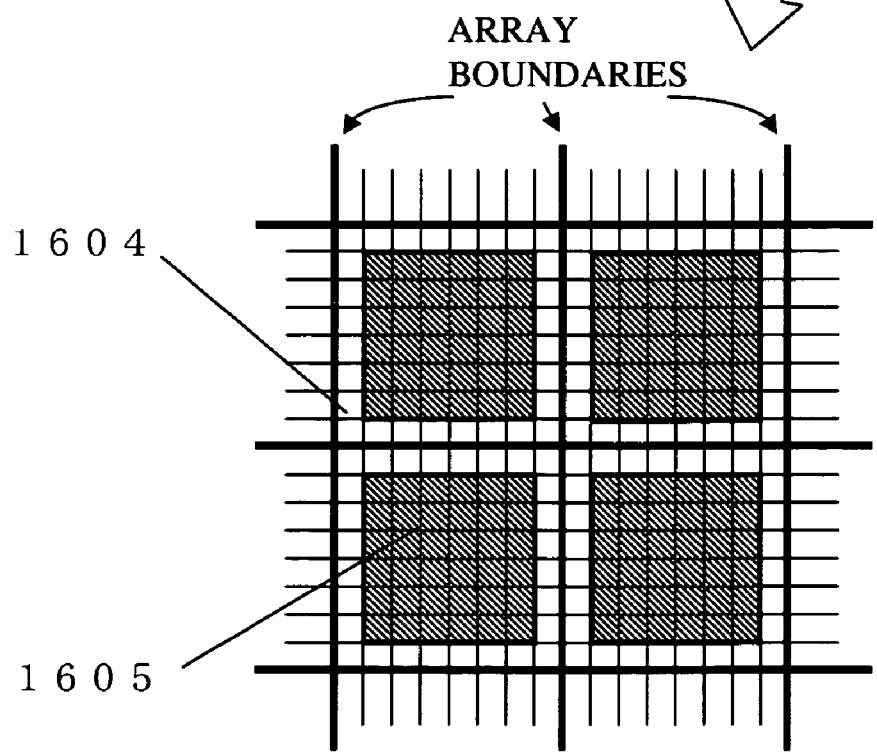
ARRAY BOUNDARIES
FIG. 16B

FIG. 17

| POLARIZATION STATE OF INCIDENT LIGHT AND OBSERVED INTENSITY DISTRIBUTION | FREQUENCY COMPONENT OBTAINED BY MEANS OF FOURIER TRANSFORM AND INCIDENT POLARIZED LIGHT STATE DETERMINED FROM FREQUENCY COMPONENT |
|---|---|
| $\varepsilon=0.5, \gamma=0°$ 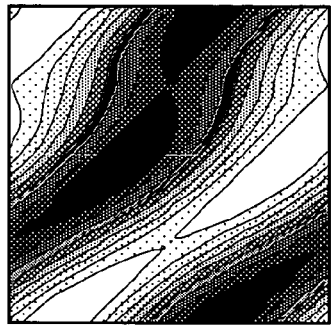 | AMPLITUDE    PHASE (deg.)<br>X:   0.1500         0.0<br>Y:   0.1500         0.0<br>Z:   0.4000       -90.0<br><br>⇨  $\varepsilon=0.5, \gamma=0°$ |
| $\varepsilon=0.5, \gamma=45°$ 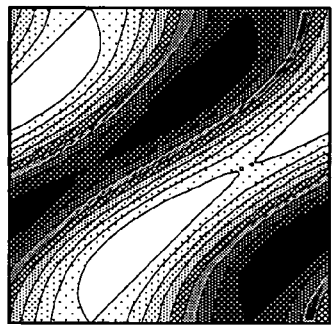 | AMPLITUDE    PHASE (deg.)<br>X:   0.1500        90.0<br>Y:   0.1500        90.0<br>Z:   0.4000       -90.0<br><br>⇨  $\varepsilon=0.5, \gamma=45°$ |
| $\varepsilon=0.5, \gamma=90°$ 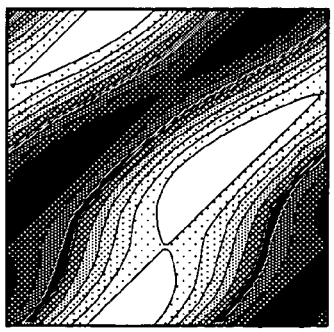 | AMPLITUDE    PHASE (deg.)<br>X:   0.1500       180.0<br>Y:   0.1500       180.0<br>Z:   0.4000       -90.0<br><br>⇨  $\varepsilon=0.5, \gamma=90°$ |

FIG. 18

| POLARIZATION STATE OF INCIDENT LIGHT AND OBSERVED INTENSITY DISTRIBUTION | FREQUENCY COMPONENT OBTAINED BY MEANS OF FOURIER TRANSFORM AND INCIDENT POLARIZED LIGHT STATE DETERMINED FROM FREQUENCY COMPONENT |
|---|---|
| $\varepsilon=0, \gamma=0°$ 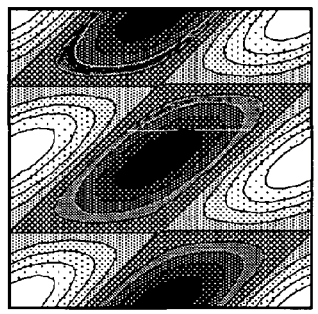 | AMPLITUDE   PHASE (deg.)<br>X :   0.2500       0.0<br>Y :   0.2500       0.0<br>Z :   0.0            -<br>⇨ $\varepsilon=0, \gamma=0°$ |
| $\varepsilon=0.2, \gamma=0°$ 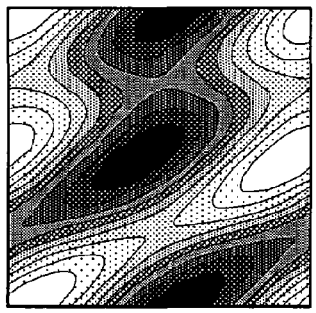 | AMPLITUDE   PHASE (deg.)<br>X :   0.2308       0.0<br>Y :   0.2308       0.0<br>Z :   0.1923      -90.0<br>⇨ $\varepsilon=0.2, \gamma=0°$ |
| $\varepsilon=1$  | AMPLITUDE   PHASE (deg.)<br>X :   0.0          0.0<br>Y :   0.0          0.0<br>Z :   0.5000      -90.0<br>⇨ $\varepsilon=1$ |

FIG. 19
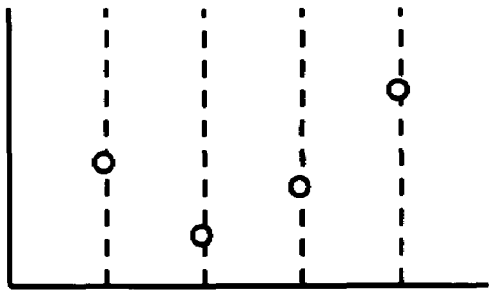
FIG. 19A
SAMPLE POINT SEQUENCE
(CONTAINING NOISE)
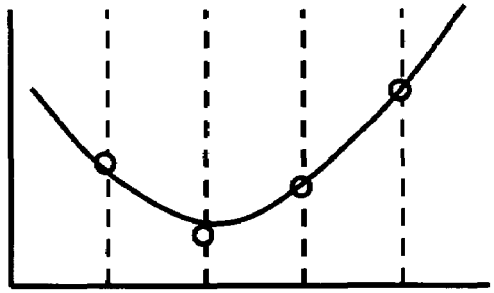
FIG. 19B
FITTING USING SECOND-ORDER
FUNCTION OF UNKNOWN
COEFFICIENT
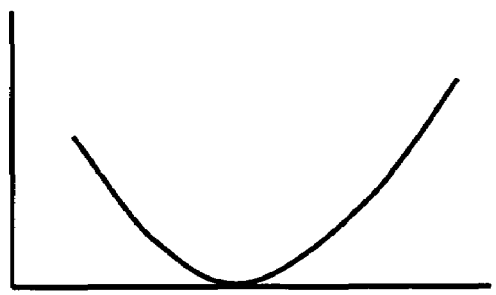
FIG. 19C
TEMPLATE CURVE OBTAINED
THROUGH FOURIER ANALYSIS
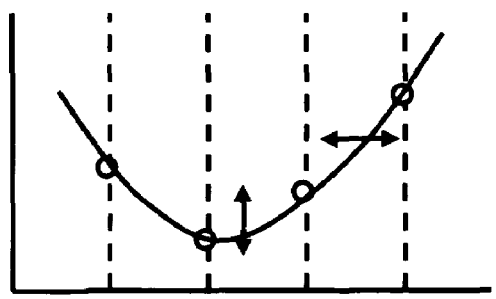
FIG. 19D
HIGHLY ACCURATE
FITTING USING PARALLEL
MOVEMENT OF TEMPLATE

DRIVERLESS ELLIPSOMETER AND ELLIPSOMETRY

CROSS REFERENCE TO RELATED APPLICATIONS

This application is a 35 USC § 371 National Stage application of PCT Application No. PCT/JP04/00633 filed Jan. 23, 2004, which claims the benefit under 35 USC § 119(a) of Japan Application No. 2003-411786 filed Dec. 10, 2003; Japan Application No. 2003-407485 filed Dec. 05, 2003; and Japan Application No. 2003-363854 filed Sep. 17, 2003.

TECHNICAL FIELD

The present invention relates to an optical polarization analysis device and an ellipsometer that measures the optical constant and thickness of a thin film by using the optical polarization analysis device.

BACKGROUND ART

Representative methods for analyzing the film quality and film thickness of a thin film include ellipsometry, which is a known old procedure. Ellipsometry is a procedure that inputs light in a specified polarization state to a thin-film sample and determines the film thickness and the refractive index of a sample and so forth by measuring the ratio ρ between the reflectance $R_p$ of a component (p polarized wave) whose electric field is parallel to the incident face and the reflectance Rs of a component (s polarized wave) whose electric field is perpendicular to the incident face, in the light that is reflected by the sample. Here, ρ is generally a complex number and can be expressed as $\rho = R_p/R_s = \tan(\psi) \times \exp(j\Delta)$. ψ and Δ are parameters that express the polarization state of the light (reflected light) to be measured and are known as ellipsometry angles. ρ is a value determined by the optical constant (n) and thickness (d) of the thin-film sample and, therefore, if the polarization state (ψ, Δ) of the reflected light can be determined by using an ellipsometer, the optical constant and film thickness of the sample can conversely be calculated.

As methods for determining ψ and Δ by performing polarization analysis of the reflected light from the sample by means of an ellipsometer, the quenching method and the rotating analyzer method and so forth that appear in documents in the Applied Physics Handbook (Applied Physics Society compilation, 1990, Maruzen, pages 20 to 22) have been used. The quenching method determines ψ and Δ by receiving the reflected light (generally elliptically polarized light) from the sample by means of an optical receiver after the light has passed through the ¼ wavelength plate and then the polarizer and then reading the rotation angle at which the optical intensity is minimum by independently rotating the ¼ wavelength plate and polarizer. However, because this method searches for the minimum value by means of two variables, there is the disadvantage that it takes a relatively long time even when performing only one measurement. One rotating analyzer method is a method that performs polarization analysis by using only the analyzer without using the ¼ wavelength plate. The rotating analyzer method measures the variation in the photoreception intensity when the polarizer is rotated once and, if the photoreception intensity is obtained as a function of the angle, ψ and Δ can be determined through calculation. However, there is the inconvenience that there is then no distinction of the phase difference from Δ (2π−Δ), that is, no distinction regarding whether this is a clockwise elliptically polarized light wave or a counterclockwise elliptically polarized light wave. Because it is necessary to perform measurement two or more times for the measurement of one point by inserting and removing the ¼ wavelength plate and so forth in order to avoid this problem, measurement is complicated and necessitates a great deal of time, which makes this method barely any different from the earlier quenching method.

Due to the marked progress of semiconductor technology in recent years, in the progress of various devices toward increased performance and miniaturization, the accuracy required of thin-film processes such as CVD and sputtering has become extremely strict and, for example, a film that is a few nanometers thick is also required to be made with an accuracy of 0.1 nm. Currently, in order to implement such highly accurate film deposition (or film-deposition devices), there is a great need for highly accurate film-thickness/film quality monitors that make it possible to perform inline measurement of the film thickness and film quality of the sample in the process. Ellipsometry is capable of accurately measuring the film thickness and film quality of thin films and is therefore said to be suited to such film-deposition monitor systems. However, conventional ellipsometry adopts complex measurement methods such as those mentioned earlier and, therefore, such devices are generally large-scale and highly expensive devices with a low measurement speed. Hence, the introduction of such devices into a process apparatus has proved difficult.

For a driverless polarization analysis device, a procedure for analyzing polarized wave states by measuring the optical intensity of four different polarized components by causing the light beam being measured to pass through respective polarizers or a wavelength plate and a polarizer after being divided into four has been proposed (Japanese Patent Application Laid Open No. H5-113371). Such a polarization measurement device is suited to simple and high-speed polarization analysis and the measurement principle has been well known for a long time as introduced in documents such as monocrystalline optics (Applied Physics Society Optics Conference, 1990, published by Morikita, pages 139 to 140). Therefore, in order to implement such a polarization analysis device, a large number of optical elements such as a beam splitter, polarizing beam splitter, ¼ wavelength plate, polarizer, and light-receiving element are required, and miniaturization of the device is difficult. Further, because it is very difficult to assemble the respective parts accurately, the measurement accuracy is poor and, therefore, an ellipsometer that necessitates highly accurate measurement of the thickness and optical constant of the thin film is not suitable.

As mentioned earlier, a procedure for analyzing the polarization state of incident light highly accurately by using a highly accurate and small-scale driverless polarization analysis device suited to ellipsometry has not yet been proposed.

DISCLOSURE OF THE INVENTION

The present invention provides a driverless polarization analysis device or ellipsometer that is constituted by integrating a polarizer array having a plurality of regions with mutually different optical axis directions, a wavelength plate array having a plurality of regions with mutually different optical axis directions or retardations (phase differences), and a light-receiving element array, as well as a polarization analysis method that employs the driverless polarization analysis device or ellipsometer. By adopting an artificial optical material that comprises a multidimensional cyclic structure known as a photonic crystal as the polarizer array and wavelength plate array, a highly reliable device that is sufficiently small can be implemented.

First, a polarizer and wavelength plate that comprise photonic crystals will first be described. A transparent medium 102 with a high refractive index and a medium 103 with a low refractive index are alternately stacked while preserving the shape at the interface on a transparent material substrate 1001 in which a row of cyclical grooves such as that in FIG. 1 are formed. Although each layer is cyclical in the x direction, each layer may be uniform in the y direction or may have a cyclical or acyclical structure of greater length in the y direction than in the x direction. Such a fine cyclical structure (photonic crystal) can be made with favorable reproducibility and high uniformity by using a system known as the autocloning technique (Japanese Patent Application Laid Open No. H10-335758). When unpolarized light or elliptically polarized light enters the cyclical structure thus created from a direction perpendicular to or oblique to plane xy, TE mode and TM mode light is exited within the cyclical structure with respect to a polarized wave parallel to the row of grooves, that is, polarized wave y and with respect to a polarized wave x that is orthogonal to polarized wave y. The propagation constant of TE mode and TM mode can be selected in a wide range by means of the refractive index of the material constituting the cyclical structure, the cycle of plane xy, and the stacking cycle.

FIG. 2 is an example of a dispersion curve of a two-dimensional structure in a case where Si is used as the high refractive index material and $SiO_2$ is used as the low refractive index material. The vertical axis represents a value rendered by normalizing the reciprocal number of the wavelength λ by means of a stacking cycle Lz and the horizontal axis represents a value rendered by normalizing a phase variation amount $k_z L_z$ ($k_z$ is the propagation constant in the z direction) by π when one cycle is propagated. A white circle indicates the TE wave and a black circle indicates the TM wave. $L_x$ represents the cycle in the in-plane direction and, here, $L_z/L_x=1$. If the frequency of the incident light is within the bandgap, the mode of the frequency cannot be propagated within the cyclical structure and the incident light is reflected or diffracted. On the other hand, if the frequency of the light is within the energy band, light can be transmitted within the cyclical structure. In frequency region 201, the TE wave is in the bandgap and is reflected and the TM wave is transmitted because same is in the propagation band and the structure therefore operates as a polarization separation element (Japanese Patent Application Laid Open No. 2001-83321). In frequency region 202, the TE wave is transmitted and the TM wave is reflected and the structure operates as a polarizer. On the other hand, in frequency region 203, the TE wave and TM wave are both in the propagation band and are transmitted. However, in this case, the respective propagation constants are different because the two curves are displaced and the structure operates as a wavelength plate that supplies two modes with a phase difference. By suitably designing the material used for the substrate pattern and deposition film, the stacking cycle, and number of stacked layers, an wavelength plate that provides an optional phase difference can be designed and, if the phase difference is π/2, for example, the structure can be made to operate as a ¼ wavelength plate. In addition, because the cycle and direction of the grooves can be changed independently for each region of one substrate, the characteristics of the photonic crystal can be changed for each region. This is called as a multipattern photonic crystal. For example, if the photonic crystal is a polarizer, the optical axis direction can be changed in each region and, if the photonic crystal is a wavelength plate, the optical axis direction and phase difference can be changed.

As the low refractive index medium that constitutes the photonic crystal, a material of which $SiO_2$ is the principal component is most typical, which has a wide transparent wavelength range and is also chemically, thermally, and mechanically stable, whereby straightforward film deposition can be performed. Further, a material with a lower refractive index such as another optical glass, $MgF_2$, for example, may be used as the low refractive index medium. A semiconductor such as Si or Ge, or the like, or an oxide or nitride such as $Ta_2O_5$, $TiO_2$, $Nb_2O_5$, $HfO_2$, or $Si_3N_4$, can be used as the high refractive index material. Because refractive of the semiconductor material is large, there is the advantage that a large bandgap is obtained. However, the useful wavelength bandwidth is limited to near-infrared. Meanwhile, because of their wide transparent wavelength range, an oxide or nitride can also be used in the visible light range.

When a photonic crystal polarizer or wavelength plate is made by means of autocloning, cyclical grooves as shown in the earlier first substrate 101 in FIG. 1 are made by means of electron beam lithography and dry etching on a substrate. Further photolithography, interference exposure, stamping technique using a metal die may be used in the formation of the groove pattern. Further, although the cross-sectional shape of the grooves is a rectangle in FIG. 1, a triangle or another shape may also be used. Si, quartz glass, or another optical glass or the like can be used as the substrate. The pitch of the recesses and protrusions is on the order of half the wavelength of the incident light, that is, on the order of 0.4 μm for light of 0.8 μm and the depth of the grooves is on the order of 0.2 μm, for example. A multiplicity of films are stacked alternately on the substrate by using a target such as $Ta_2O_5$ and $SiO_2$ and combining sputter deposition and bias sputtering. Here, it is essential to suitably establish a bias condition so that the cyclical corrugated shape is preserved in the x axis direction of each layer. An example of the condition is as follows. In the film deposition of the $Ta_2O_5$ layer, the gas pressure was 2 mTorr and the target application high frequency power was 300 W. In the film deposition of the $SiO_2$ layer, the gas pressure was 6 mTorr and the target application high frequency power was 300 W. Sputter etching was performed after the film deposition of the $SiO_2$ layer and the gas pressure was 2 mTorr, and the substrate application high frequency power was 90 W.

The polarization analysis device of the present invention will be described next. A representative example of the driverless polarization analysis device that uses a wavelength plate array and polarizer array is shown in FIG. 3. The wavelength plate array 301 has a plurality of regions the orientation of the optical axes of which is different arranged in M rows and the design is such that the retardation amount of the respective regions is constant (ideally a ¼ wavelength plate). Further, a polarizer array 302 has a plurality of regions in which the polarization direction of the transmitted light is different arranged in N rows and the design is such that the polarized wave quench ratio of the respective regions is sufficiently high. A polarization analysis device can be implemented by sticking together this wavelength plate array and polarizer array so that same lie orthogonal to each other and disposing, behind the wavelength plate array and polarizer array, a light-receiving element array 303 that is capable of individually receiving light transmitted by M×N regions that are made as a result of the overlap between the wavelength plate array and polarizer array. The photonic crystal polarizer can be used as a polarizer array and wavelength plate array, whereby the device can be miniaturized and afforded greater accuracy.

When light enters such a polarization analysis device, the polarized wave state of the incident light is converted in each of the respective regions by means of the wavelength plate array, whereupon only a specified polarized component that is fixed in the direction of the axis of the respective regions of the polarizer array is transmitted. Therefore, each of the light-receiving elements of the light-receiving element array detects the optical intensity of the light transmitted by the wavelength plate and polarizer with respectively different angles, that is, the optical intensity of the respectively different polarized wave components. As a result, by analyzing the intensity of the light detected by each of the light-receiving elements, the polarization state of the incident light can be grasped two-dimensionally. By way of example, FIG. 4 shows an example of the simulation results of the intensity distribution of light that is sensed by a detector array of 256 elements when the phase difference of the wavelength plate array is π/2 (¼ wavelength) and the number of partitions of the wavelength plate array and polarizer array is 16 in a polarization analysis device such as that described above. Here, the simulation results for cases where the regions of the ¼ wavelength plate array are arranged in the vertical direction such that the angle of the principal axis of each region is changed 12° at a time from 0° to 180°, the angle of the principal axis (angle of the transmitted polarized wave) of each region of the polarizer array is the same, and the regions of the ¼ wavelength plate are arranged in the horizontal direction such that the angle of the principal axis of each region is changed 12° at a time from 0° to 180°. As can also be seen from the results, the intensity distribution shape of the light observed by the light-receiving elements is changed in accordance with the polarization state of the incident light. Hence, by analyzing the intensity distribution pattern, the polarization state of the incident light can also conversely be stopped.

Here, a theoretical (mathematical) study is performed on the intensity distribution pattern observed by the polarization analysis device of the present invention. Because the polarization states of the light entering the device is expressed by ψ and Δ, which are ellipsometry angles, Johnson's vector of the light that has passed through the wavelength plate and polarizer can be expressed as $$\vec{u} = \begin{pmatrix} 1 & 0 \\ 0 & 0 \end{pmatrix} \begin{pmatrix} \cos\phi & \sin\phi \\ -\sin\phi & \cos\phi \end{pmatrix} \begin{pmatrix} \cos\theta & -\sin\theta \\ \sin\theta & \cos\theta \end{pmatrix} \begin{pmatrix} e^{j\alpha} & 0 \\ 0 & 1 \end{pmatrix} \begin{pmatrix} \cos\theta & \sin\theta \\ -\sin\theta & \cos\theta \end{pmatrix} \begin{pmatrix} 1 \\ \tan\Psi \cdot e^{j\Delta} \end{pmatrix}$$ (Equation 1)

In this equation, θ is the principal axis angle of the wavelength plate, α expresses the retardation (phase difference) of the wavelength plate, and φ expresses the principal axis angle of the polarizer. As shown in FIG. 5, the polarization state of the incident light is expressed by the ellipticity (ε) and tilt (γ) of the elliptically polarized wave rather than being expressed by the ellipsometry angle. However, an image of the polarization state is easy to take. By using this image, the polarization state of the incident light can be substituted as $$\begin{pmatrix} 1 \\ \tan\Psi \cdot e^{j\Delta} \end{pmatrix} = \begin{pmatrix} \cos\gamma & -\sin\gamma \\ \sin\gamma & \cos\gamma \end{pmatrix} \begin{pmatrix} 1 \\ j\varepsilon \end{pmatrix}$$ (Equation 2)

Therefore, the polarized wave state of light that reaches the light-receiving element array can consequently be expressed as:

$$\vec{u} = \begin{pmatrix} 1 & 0 \\ 0 & 0 \end{pmatrix} \begin{pmatrix} \cos(\phi-\theta) & \sin(\phi-\theta) \\ -\sin(\phi-\theta) & \cos(\phi-\theta) \end{pmatrix} \begin{pmatrix} e^{j\alpha} & 0 \\ 0 & 1 \end{pmatrix} \begin{pmatrix} \cos(\theta-\gamma) & \sin(\theta-\gamma) \\ -\sin(\theta-\gamma) & \cos(\theta-\gamma) \end{pmatrix} \begin{pmatrix} 1 \\ j\varepsilon \end{pmatrix}$$ (Equation 3)

and the observed optical intensity can be determined by $$|\vec{u}|^2 = \vec{u}^* \cdot \vec{u}$$ (Equation 4)

That is, the intensity distribution observed by the light-receiving element array is expressed as a function of the incident polarized wave state (ε, γ) and the angle (θ) of the wavelength plate and the angle (φ) of the polarizer. θ and φ are known device-dependent values and, therefore, the polarization state of the incident light may be accurately found by analyzing the shape of the observed optical intensity distribution, but is also obvious from a theoretical viewpoint.

The simplest method of analyzing the intensity distribution pattern is a method that detects the position of the minimum value of the measured pattern. This corresponds to the quenching method by a conventional ellipsometer mentioned earlier. In the quenching method, the ellipticity and tilt of the incident light can be determined directly from the angle of the wavelength plate and the angle of the wavelength plate and polarizer when the polarizer is rotated and the incident light is completely quenched. On the other hand, by specifying the position of a dark spot (minimum value, zero point) that is produced in the two-dimensional intensity distribution by means of exactly the same principles as for the case of the new polarization analysis device that uses the wavelength plate array and polarizer array of the present invention, that is, the principal axis angle of the polarizer and the wavelength plate, the polarization state of the incident light can be found instantly. However, this method does not utilize the majority of the two-dimensional information observed and it is hard to say that this method adequately produces the benefits of the new polarization analysis device. Further, because the dark spot is displaced from the ideal position when the phase difference of the wavelength plate is not strictly a ¼ wavelength, for example, there is the inconvenience that highly accurate polarized wave analysis is impossible.

Therefore, as a pattern analysis method that analyzes the shape of the pattern by using a greater number of data points and is able to also perform correction with respect to the shift of the wavelength plate, the present invention proposes a two-dimensional pattern Fourier analysis method and a dark spot vicinity shape fitting method. The Fourier analysis method uses the fact the intensity distribution pattern observed by the polarization analysis device is expressed by a simple frequency component and judges the incident polarized light state from the phase value and the amplitude of the respective frequency components found by subjecting the pattern shape to a Fourier transform. In the first dark spot vicinity shape fitting method, an accurate dark spot position is calculated by finding the pattern shape in the vicinity of the minimum value of the optical intensity by means of an approximation calculation. High-speed and highly accurate polarization analysis that is resistant to noise is made possible through the combined usage of these two methods of analysis.

The polarization analysis device of the present invention as described above or an ellipsometer that uses the polarization analysis device of the present invention can be made highly accurately by using a photonic crystal (a multi-pattern photonic crystal). Further, as the light-receiving element array, a conventional image sensor such as a CCD or the like can be used. Therefore, in comparison with conventional products, the ellipsometer of the present invention is capable not just of implementing a very small and stable device but also a highly reliable device. Hence, new usage methods that are almost impossible for conventional ellipsometers to perform such as usage as a real time monitor of film thickness and film quality through introduction of the device in a thin-film process device is also to be expected. The claims of the present invention will be described simply hereinbelow.

The polarization analysis device according to claim 1 comprises a polarizer array having a plurality of regions in which the directions of transmitted polarized waves are different and a wavelength plate array having a plurality of regions in which the phase difference supplied to transmitted light is fixed and the optical axis directions are different, wherein the wavelength plate array and polarizer array are disposed overlapping one another such that wavelength plate array is disposed at the front and the polarizer array is disposed at the rear, and a light-receiving element array is disposed two-dimensionally to be capable of individually receiving light passed through respective regions obtained by the overlap between the wavelength plates and polarizers. Here, the wavelength plate array, polarizer array and light-receiving element array can be integrated by being stuck together directly. However, a relay lens may be disposed between the respective arrays to form an image that has been transmitted by the respective arrays on the next array. Further, in order to implement highly accurate polarized wave analysis for all the polarized wave states, the phase difference of the respective regions of the wavelength plate array is ¼ wavelength ($\pi/2$ radians) and the optical axis direction of the wavelength plate array and the optical axis direction of the polarizer array desirably cover a range of at least 0° to 180°. In addition, the higher the number of partitions of the regions of the polarizer array and wavelength plate array, the higher the measurement accuracy.

The polarization analysis device according to claim 2 comprises a polarizer array having at least two or more stripe-like regions in which the directions of transmitted polarized waves are different, and a wavelength plate array having at least two or more stripe-like regions in which phase differences supplied to transmitted light are uniform and optical axis directions are different, wherein the wavelength plate array and the polarizer array are arranged such that the wavelength plate array is at the front and the polarizer array is at the rear and the respective stripes of the wavelength plate array and the polarizer array intersect one another, and a light-receiving element array is disposed so as to be capable of individually receiving light passed through the respective regions of intersection. Similarly to the case of claim 1, although the wavelength plate array, polarizer array and light-receiving element array can also be integrated by being stuck together directly, a relay lens may be disposed between the respective arrays to form an image that has been transmitted by the respective arrays on the next array. Further, in order to implement highly accurate polarized wave analysis for all the polarized wave states, the phase difference of the respective regions of the wavelength plate array is ¼ wavelength ($\pi/2$ radians) and the optical axis direction of the wavelength plate array and the optical axis direction of the polarizer array desirably cover a range of at least 0° to 180°. In addition, the higher the number of stripe-like regions of the polarizer array and wavelength plate array, the higher the measurement accuracy.

The polarization analysis device according to claim 3, wherein the polarizer array and the wavelength plate array comprise a dielectric multilayered film in which the shape of the layers is cyclical in the stacking direction and in which the shape of each layer has a cyclical corrugated shape that is repeated in one direction in a plane determined for each region.

The polarization analysis device according to claim 4, comprising: a polarizer array having a plurality of regions in which the directions of transmitted polarized waves are different; and a wavelength plate array having a plurality of regions in which optical axis directions are uniform and phase differences of transmitted light are different, wherein the wavelength plate array and the polarizer array are disposed to overlap one another such that the wavelength plate array is at the front and the polarizer array is at the rear, and a light element array is disposed so as to be capable of individually receiving light passed through respective regions that are obtained due to the overlap between the wavelength plates and polarizers. Here, although the wavelength plate array, polarizer array and light-receiving element array can also be integrated by being stuck together directly, a relay lens may be disposed between the respective arrays to form an image that has been transmitted by the respective arrays on the next array. Further, in order to implement highly accurate polarized wave analysis for all the polarized wave states, the phase difference of the respective regions of the wavelength plate array desirably covers a range of 0° to 360° and the principal axis angle of the polarizer array desirably covers a range of 0° to 180°. In addition, the higher the number of partitions of the polarizer array and wavelength plate array, the higher the measurement accuracy.

The polarization analysis device according to claim 5, comprising: a polarizer array having at least two or more stripe-like regions in which the directions of transmitted polarized, waves are different; and a wavelength plate array having at least two or more stripe-like regions in which optical axis directions are uniform and phase differences of transmitted light are different, wherein the wavelength plate array and the polarizer array are arranged such that the wavelength plate array is at the front and the polarizer array is at the rear and the respective stripes of the wavelength plate array and the polarizer array intersect one another, and a light element array is disposed so as to be capable of individually receiving light passed through the respective regions of intersection. Here, as the case of claim 4, although the wavelength plate array, polarizer array and light-receiving element array can also be integrated by being stuck together directly, a relay lens may be disposed between the respective arrays to form an image that has been transmitted by the respective arrays on the next array. Further, in order to implement highly accurate polarized wave analysis for all the polarized wave states, the phase difference of the respective regions of the wavelength plate array desirably covers a range of 0° to 360° and the principal axis angle of the polarizer array desirably covers a range of 0° to 180°. In addition, the higher the number of partitions of the polarizer array and wavelength plate array, the higher the measurement accuracy.

The polarization analysis device according to claim 6 is the polarization analysis device according to claim 4 or 5, wherein the polarizer array comprises a dielectric multilayered film the shape of which is cyclical in the stacking direction and in which the shape of each layer has a cyclical corrugated shape that is repeated in one direction within a plane determined for each region and the wavelength plate array comprises a dielectric multilayered film the shape of which is cyclical in the stacking direction and which has a common corrugated shape that is cyclical in one direction with a repetitive cycle determined for each region.

The polarization analysis device according to claim 7 is a polarization analysis device that combines the polarization analysis device according to claim 1, 2 or 3 and the polarization analysis device according to claim 4, 5, or 6, wherein the light beam to be measured enters each of the polarization analysis devices.

The polarization analysis device according to claim 8 is the polarization analysis device according to any of claims 1 to 7, wherein unnecessary multiple reflection light is reduced by providing a light-absorbing layer between the wavelength plate array and the polarizer array or between the polarizer array and the light-receiving element array or both, or by forming a nontransparent region or transparent region at the boundary of the respective array regions for at least one of the wavelength plate array and the polarizer array or the light-receiving element array.

The polarization analysis device according to claim 9, wherein, by providing an isotropic transparent region for incident polarized light in a peripheral part of the wavelength plate array and the polarizer array in the polarization analysis device according to any of claims 1 to 8 or through combination with the light-receiving element array by providing an isotropic transparent region for incident polarized light in a portion of the boundary part of the respective regions of the wavelength plate array and the polarizer array, an intensity distribution of incident light and a transmission loss distribution of the wavelength plate array and the polarizer array are measured as well as the conventionally measured intensity distribution of light passed through a wavelength plate and polarizer, and the measurement results are corrected.

The polarization analysis device according to claim 10, wherein, in order to suppress the effects of diffracted light and scattered light from the boundary part of the respective regions of the wavelength plate array and the polarizer array in the polarization analysis device according to any of claims 1 to 9, a light-shielding region is provided in the boundary part of the respective regions of the wavelength plate array and the polarizer array or a region of the light-receiving element array that corresponds with the boundary part of the wavelength plate array and the polarizer array is light-shielded. Naturally, the light-shielding of the boundary part of the wavelength plate array and the polarizer array and the light-shielding of the region corresponding with the light-receiving element array may be performed at the same time.

The polarization analysis device according to claim 11 is a polarization analysis device, wherein measurement errors caused by positional fluctuations of the incident light beam are avoided by arranging a plurality of the polarization analysis device according to any of claims 1 to 10 within a plane.

The light measurement device or light measurement system according to claim 12 employs the polarization analysis device according to any of claims 1 to 11.

The ellipsometer according to claim 13 is an ellipsometer that causes polarized light of a specified wavelength to enter a measurement sample at a predetermined angle, introduces the reflected light reflected by the measurement sample to the polarization analysis device according to any of claims 1 to 11 and obtains the amplitude reflectance ratio of the P polarization component and the S polarization component from an optical intensity distribution obtained by a light-receiving element array. In this case, an optical wavelength filter that corresponds with wavelengths of incident light can also be inserted in front of the polarization analysis device in order to improve the measurement accuracy by removing light excluding the reflected light reflected by the sample.

The ellipsometer according to claim 14 is an ellipsometer that causes light of a specified wavelength and a specified polarized state to enter a substrate surface undergoing thin-film deposition at a predetermined angle in a vacuum thin-film formation device, introduces reflected light reflected by the substrate surface to the polarization analysis device according to any of claims 1 to 11, and obtains the amplitude reflectance ratio of the P polarization component and S polarization component from an optical intensity distribution obtained by the light-receiving element array. In this case, an optical wavelength filter that corresponds with the wavelength of the incident light is desirably inserted in front of the polarization analysis device in order to remove radiant light and scattered light in the film-deposition device excluding the reflected light reflected by the sample.

The film thickness and film quality control device according to claim 15 is a film thickness and film quality control device, wherein film thickness and film quality information obtained by the ellipsometer according to claim 13 or 14 is fed back to a device for controlling the film deposition speed or film deposition time.

The film thickness and film quality control device according to claim 16 is a film thickness and film quality control device, comprising: at least two or more of the ellipsometers according to claim 13 or 14, wherein information obtained by measuring the film thickness and film quality in different positions of the substrate at each point is fed back to a film thickness and film quality distribution correction control device.

The polarization analysis method or polarization analysis system according to claim 17 is a polarization analysis method or polarization analysis system, wherein, in a polarization analysis device in which a wavelength plate array having a plurality of regions in which the phase differences are fixed and the optical axis directions are different and a polarizer array having a plurality of regions in which the directions of transmitted polarized waves are different are made to overlap one another and a light-receiving element array is disposed in two dimensions so as to be capable of individually receiving light passed through a certain region of the wavelength plate and a certain region of the polarizer, the polarization state of incident light is obtained by using the characteristics that a two-dimensional intensity distribution pattern observed by means of the light-receiving element array is exhibited by only a DC component and at most three frequency components.

The polarization analysis method or polarization analysis system according to claim 18 is a polarization analysis method or polarization analysis system, wherein, by fitting or inserting sample values in use of the characteristics of a pattern shape in the neighborhood of a maximum point or a minimum point of an intensity distribution pattern observed by the light-receiving element array in the polarization analysis method or polarization analysis system according to claim 17, the ellipsometry quenching point or the minimum of the flow amount are determined and the polarization state of incident light is obtained.

The polarization analysis method or polarization analysis system according to claim 19 is a polarization analysis method or polarization analysis system, wherein a Fourier transform is adopted as the method of analyzing the formation of the observed intensity distribution pattern in the polarization analysis method or polarization analysis system according to claim 7.

The polarization analysis method or polarization analysis system according to claim 20 is a polarization analysis method or polarization analysis system, wherein the polarization analysis method according to claim 18 and the polarization analysis method according to claim 19 are combined.

The polarization analysis method or polarization analysis system according to claim 21 is a polarization analysis method or polarization analysis system, wherein, by analyzing the shape of the observed intensity distribution pattern in the polarization analysis method or polarization analysis system according to any of claims 17 to 20, the value of the phase difference of the wavelength plate array used by the polarization analysis device is detected and shifts from the design values are self-corrected.

The signal processing method according to claim 22 is a signal processing method, wherein, in order to remove the effects of scattered light and diffracted light from the boundary part of the respective regions of the wavelength plate array or polarizer array in the polarization analysis method or polarization analysis system according to any of claims 17 to 21, signals are removed from a region that receives the scattered light and diffracted light among signals output by the light-receiving element array.

BRIEF DESCRIPTION OF THE DRAWINGS

FIG. 8 shows examples of the difference in the intensity distribution pattern depending on the number of partitions of the wavelength plate and polarizer;

FIG. 12 is an example of the observed intensity distribution pattern (relationship with the tilt of the incident polarized wave);

FIG. 16 shows a signal processing system that removes the effects caused by the boundary part of an array;

FIG. 17 is a simulation result (1) of Fourier analysis of an intensity distribution pattern;

FIG. 18 is a simulation result (2) of Fourier analysis of an intensity distribution pattern;

FIG. 19 is an example of a pattern analysis algorithm that combines usage of Fourier analysis and dark spot detection;

BEST MODE FOR CARRYING OUT THE INVENTION

Figure 1:
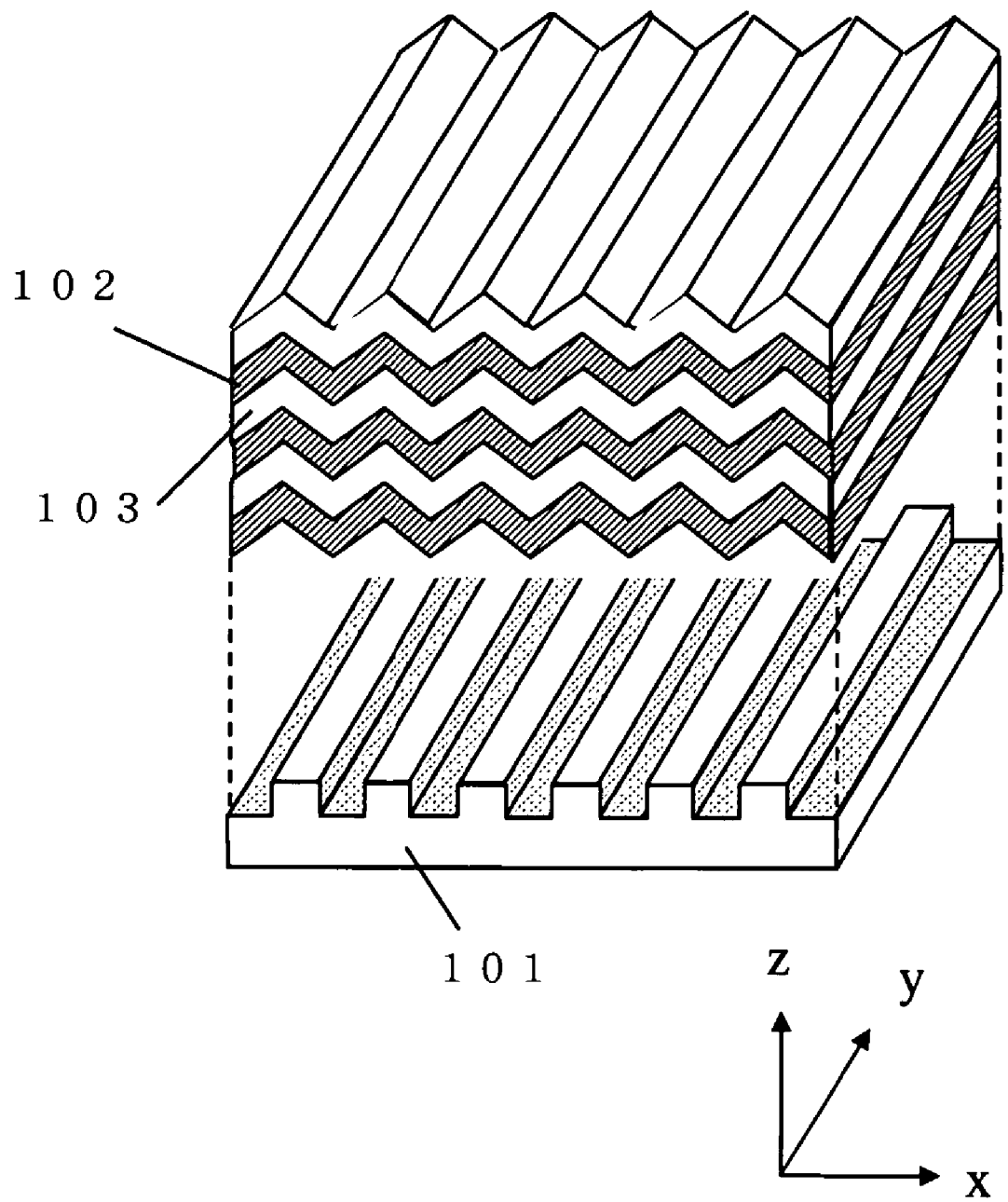
FIG. 1 is a conceptual view of a polarizer or wavelength plate comprising a photonic crystal.
Figure 2:
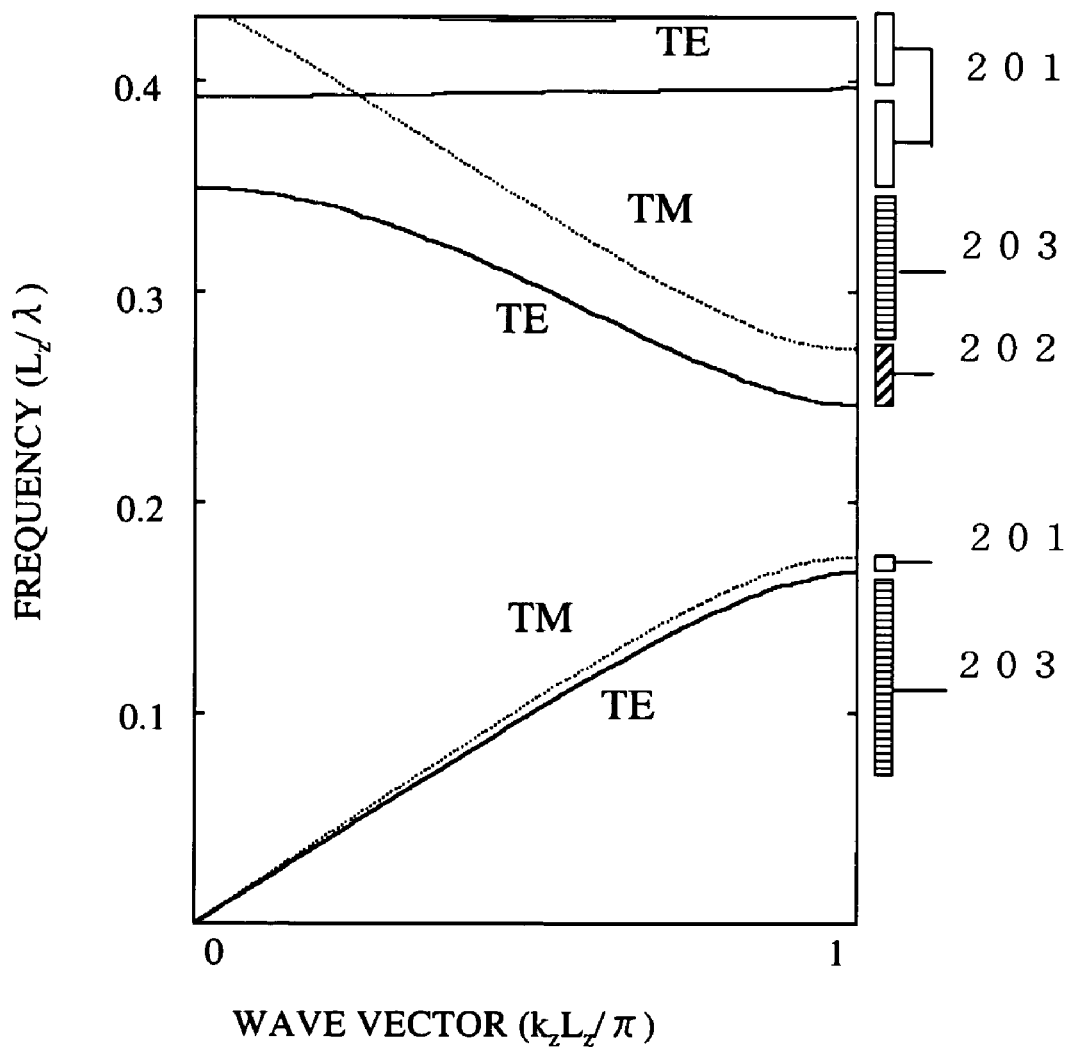
FIG. 2 is a band diagram representing the propagation characteristic of the photonic crystal shown in FIG. 1.

A polarization analysis device that is constituted by a combination of a polarizer array comprising an autocloning-type photonic crystal, a wavelength plate array similarly comprising an autocloning-type photonic crystal, and a light-receiving element array will be described first. As mentioned earlier, the photonic crystal polarizer and photonic crystal wavelength plate has the constitution in FIG. 1 and is made by performing autocloning to grow two inorganic materials 102 and 103 on a substrate 101 formed having a two-dimensional groove pattern. Here, by controlling the cycle of the grooves created on the substrate 101, the material used in the film deposition, and the cycle of each layer, and so forth, various characteristics such as the refractive index of light and bandwidth of the photonic bandgap (PBG) can be freely designed. By using these characteristics to suitably select the design parameters, not only is it possible to create a polarizer (polarization splitter) that transmits one polarized wave (TM: polarized wave perpendicular to the substrate pattern) and blocks another polarized wave (TE: polarized wave parallel to the substrate pattern) with respect to light of a certain specified wavelength, but a wavelength plate that provides an optional phase difference between the two polarized waves can also be created.

Figure 3:
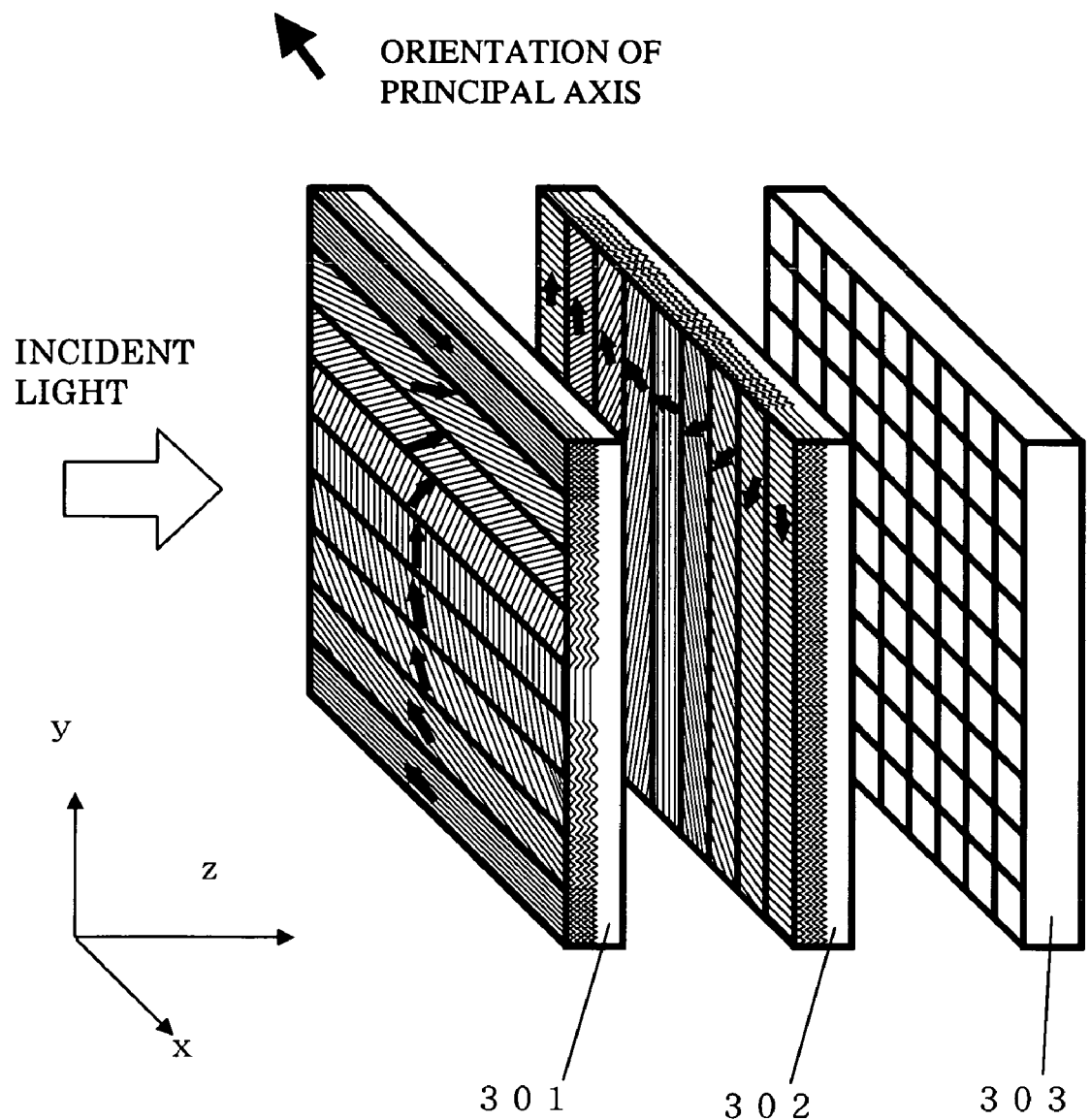
FIG. 3 is an 'angle variation-type' polarization analysis device that is constituted by using a photonic crystal.

A constitutional example in which a 'wavelength plate angle variation-type' polarization analysis device that employs a photonic crystal represented by claim 3 of the present invention is shown in FIG. 3. The wavelength plate array 301 and polarizer array 302 are constituted by using an autocloning-type photonic crystal and each of the complex structures illustrated can be fabricated by a single process. The photonic crystal wavelength plate array 301 is produced by arranging M regions that are produced by changing the groove direction (the orientation of the optical axis of the wavelength plate) a little at a time and the design is such that the retardation amount of the respective regions (phase difference between the TM light and TE light) is fixed. Similarly, the photonic crystal polarizer array 302 is also produced by arranging N regions that are produced by changing the groove direction (the direction of the light-shielded polarized wave) a little at a time, the design being such that the polarized wave quench ratio of the respective regions is sufficiently high. In FIG. 3, the x axis direction is the horizontal direction, the y axis direction is the vertical direction, and the angle of the axes of the wavelength plate and polarizer is changed gradually from 0° to 180° with the x axis serving as a reference. However, the adoption of a reference axis and the range of the angle and so forth are optional. Further, in FIG. 3, regions with different crystal axes are disposed so that the respective angle in the x direction (horizontally) of the wavelength plate array 301 and in the y direction (vertically) of the polarizer array 302 gradually changes. However, if the arrangement directions of the wavelength plate and polarizer intersect one another, the arrangement direction and arrangement order are optional. The wavelength plate array and polarizer plate array are stuck together so that same lie orthogonal to each other, behind which the light-receiving element array 303 is disposed and the intensity of light transmitted by M×N regions that are created by the overlap between the wavelength plate array and the polarizer array is individually measured. Existing parts such as the CCD can be used for the optical receiver array and a sufficiently small device can be implemented.

The incident light is input by the polarization analysis device with a sufficiently large spot size. Only a specified polarized wave component of the incident light that is fixed in the direction of the axis of the respective regions of the polarizer array is transmitted following conversion of the polarized wave state for each region by means of the wavelength plate array. Therefore, the light-receiving elements of the optical receiver element array separately detect the light transmitted by the respective wavelength plate and polarizer at respectively different angles, whereby the polarization state of the incident light can be grasped two-dimensionally by analyzing the intensity of the light detected by the light-receiving elements.

Figure 4:
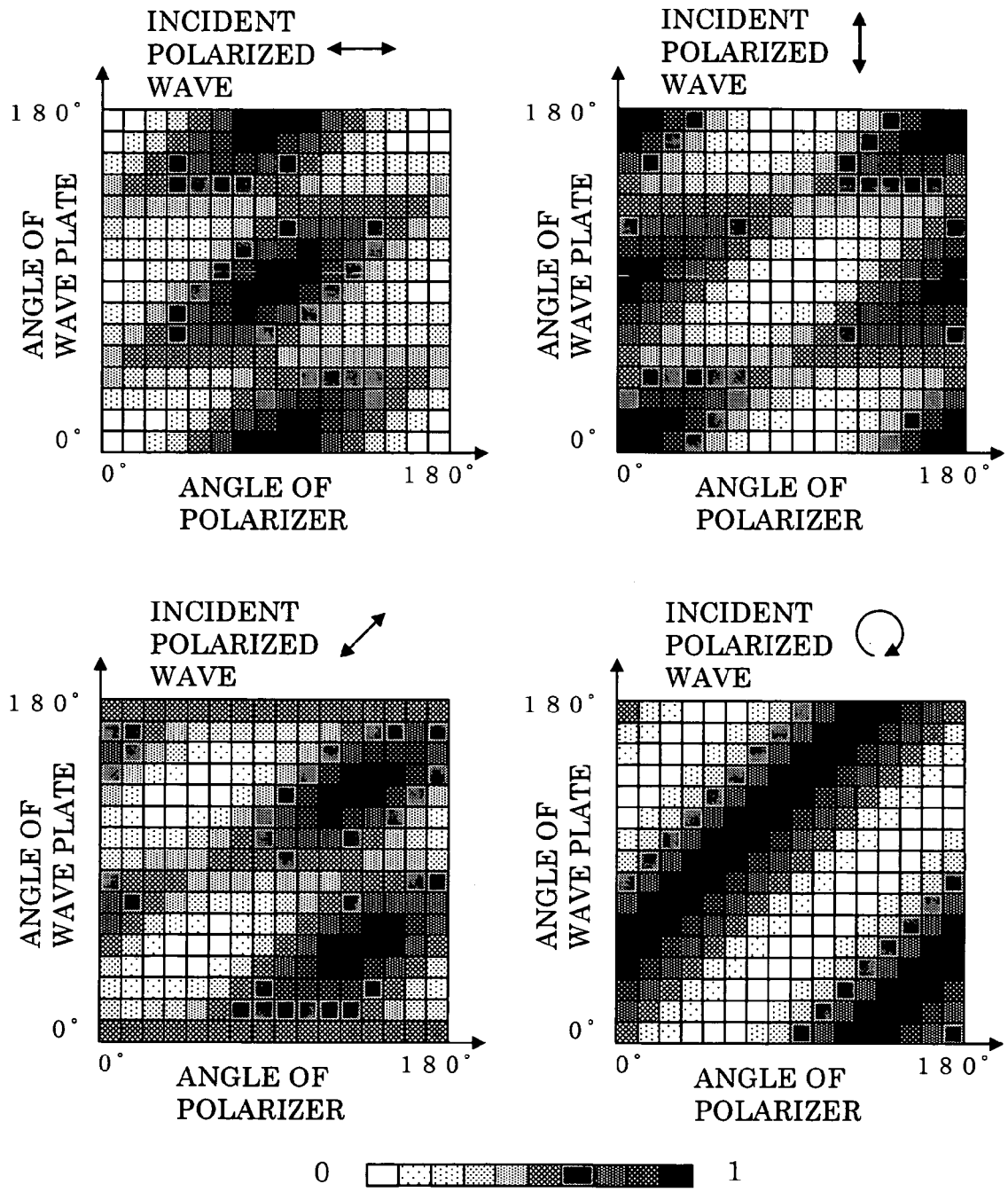
FIG. 4 is an example of the intensity distribution of light that is observed when the polarization analysis device of FIG. 3 is used.

FIG. 4 shows an example of simulation results of the intensity distribution of light sensed by a detector array of 256 elements when the phase difference of the wavelength plate array is $\pi/2$ (¼ wavelength) and the number of partitions of the wavelength plate array and polarizer array is 16, in a wavelength plate angle variation-type polarization analysis device of this kind. Here, the simulation results for cases where the regions of the ¼ wavelength plate array are arranged in the vertical direction such that the angle of the principal axis of each region is changed 12° at a time from 0° to 180°, the angle of the principal axis (angle of the transmitted polarized wave) of each region of the polarizer array is the same, and the regions of the ¼ wavelength plate are arranged in the horizontal direction such that the angle of the principal axis of each region is changed 12° at a time from 0° to 180°. As can also be seen from the results, because the intensity distribution shape of the light detected by the detector changes in accordance with the polarization state of the incident light, the polarization state of the incident light can be judged by analyzing the intensity distribution pattern thus obtained. Great results can be expected in miniaturizing the device, shortening the measurement time, and increasing the measurement accuracy in comparison with a quenching-type ellipsometer that employs a conventional rotating ¼ wavelength plate and rotating polarizer and so forth.

Figure 6:
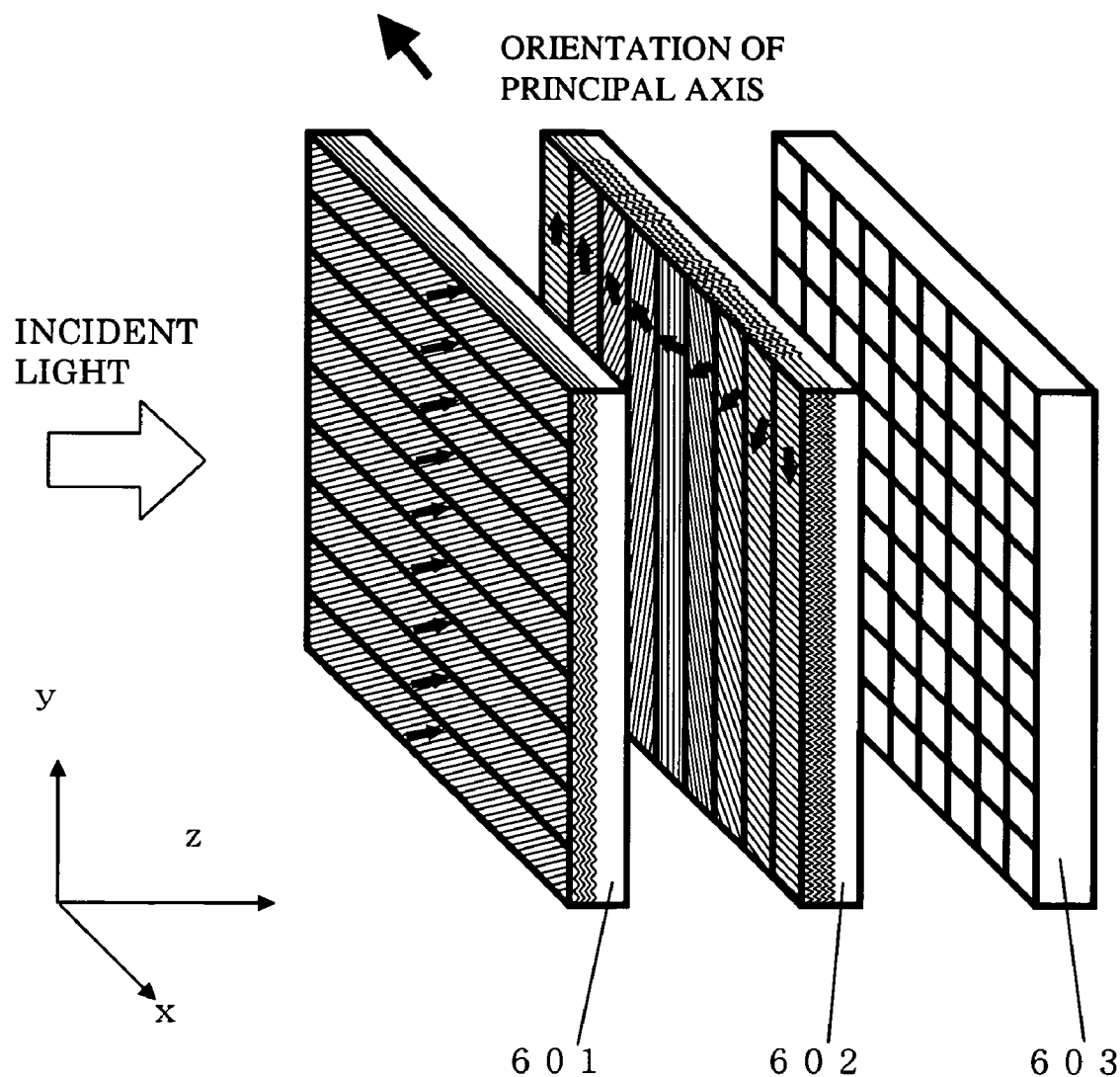
FIG. 6 is a 'phase difference variation-type' polarization analysis device that is constituted by using a photonic crystal.

Thereafter, a constitutional example that implements a 'wavelength plate phase difference variation-type' polarization analysis device that uses a photonic crystal represented by claim 6 of the present invention is shown in FIG. 6. A wavelength plate array 601 and polarizer array 602 are formed by an autocloning-type photonic crystal and the complex structure illustrated can be implemented easily. The plurality of array 602 is the same as that illustrated in FIG. 3 (claim 3) mentioned earlier and is produced by arranging N regions produced by changing the groove direction (direction of the light-shielded polarized wave) a little at a time, the design being such that the polarized wave quench ratio of the respective regions is sufficiently high. Meanwhile, the orientation of the grooves (orientation of the optical axis) is the same for all the regions of the wavelength plate array 601 and the retardation amount of the respective regions is changed to produce M different retardation amounts. Although the optical axis of the wavelength plate array is 45° to the x axis (horizontal direction) in FIG. 6, the optical axis may be set at an optional angle such as 0° or 90°. Further, as in the case of the wavelength plate angle variation-type polarization analysis device (FIG. 3), the adoption of a reference axis, array arrangement direction, arrangement order, the angle range of the principal axis of the polarizer array, and the range of the phase difference of the wavelength plate array are optional. The wavelength plate array and polarizer array are stuck together to lie orthogonal to one another, behind which a light-receiving element array 603 is disposed and the intensity of light transmitted by M×N regions that are created by the overlap between the wavelength plate array and the polarizer array is individually measured. A case that employs this wavelength plate phase difference variation-type polarization analysis device is the same as the earlier case of the wavelength plate angle variation-type polarization analysis device and is capable of grasping the polarization state of incident light two-dimensionally by analyzing the angle of light that is received by the respective light-receiving elements of the light-receiving element array.

Figure 7:
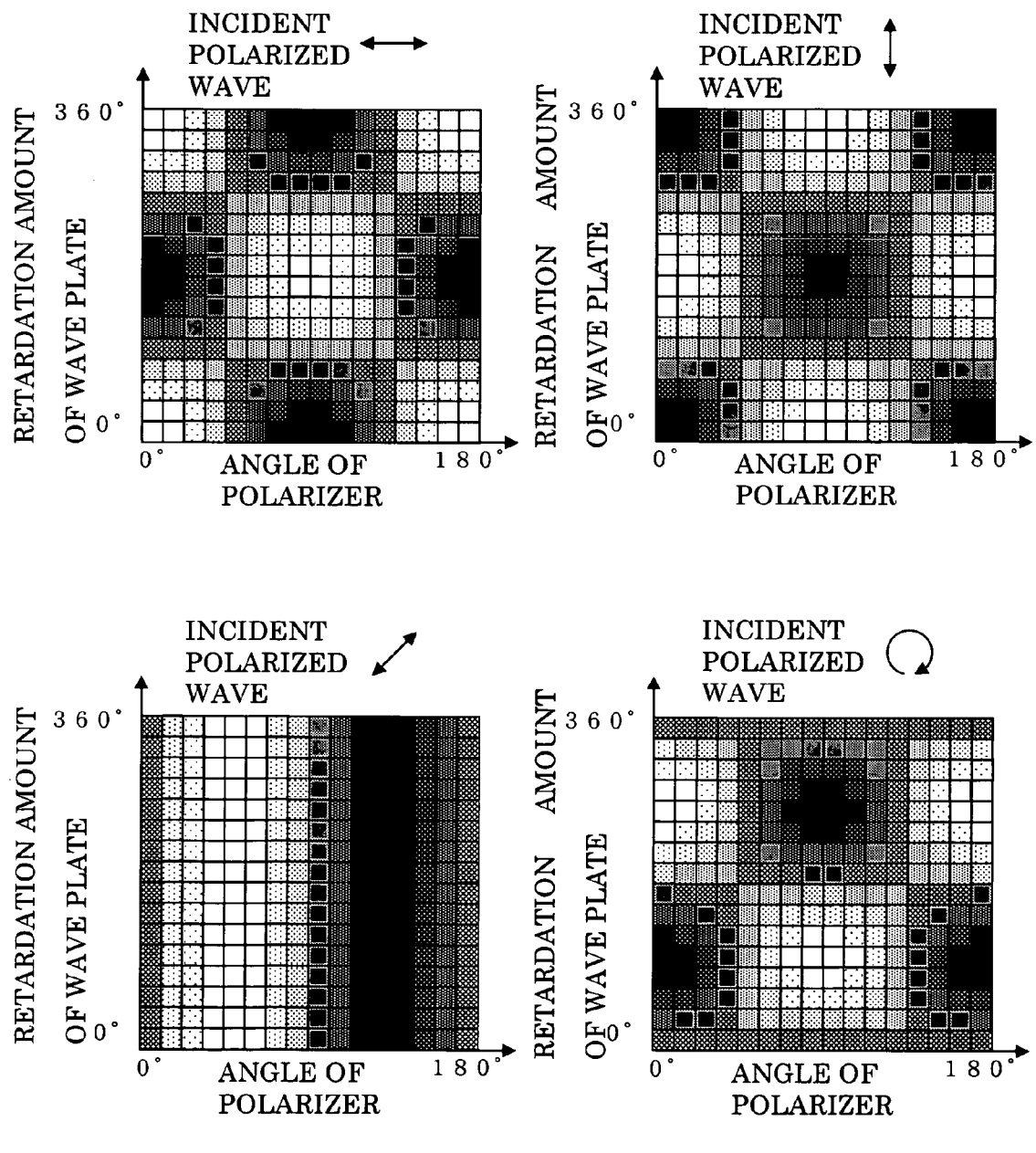
FIG. 7 shows examples of the intensity distribution of light that is observed when the polarization analysis device in FIG. 6 is used.

FIG. 7 shows an example of the intensity distribution of light that is sensed by a light-receiving element array in a case where the number of partitions of the wavelength plate array and polarizer array is 16, the principal axis of the polarizer array is changed a 12° at a time from 0° to 180°, and the retardation amount of the wavelength plate array is changed 24° at a time from 0° to 360°, in a phase difference variation-type polarized wave analysis device. As the earlier case in FIG. 4, the principal axis angle of the polarizer (orientation of the polarized wave transmitted) is plotted on the horizontal axis and the retardation amount of the wavelength plate is plotted on the vertical axis, and the optical intensity that is sensed by the optical receivers of 256 elements was found by means of simulation. In this case also, because the intensity distribution of the light detected by the detector changes in accordance with the polarization state of the incident light, the polarization state of the incident light can be judged by analyzing the intensity distribution pattern thus obtained. Great results can be expected in miniaturizing the device, shortening the measurement time, and increasing the measurement accuracy in comparison with a rotating quenching-type ellipsometer that employs a conventional phase modulator.

A polarization analysis method in cases employing a wavelength plate angle variation-type polarization analysis device and a wavelength plate phase difference variation-type polarization analysis device will be described next. As has already been mentioned, the shape of the intensity distribution pattern observed by the polarization analysis device of the present invention is dependent on the polarization state of the incident light. Therefore, the polarization state of the incident light is judged conversely by analyzing the observed intensity distribution pattern. A method for detecting a maximum value (bright spot) or a minimum value (dark spot, zero point) of the intensity distribution pattern of the intensity distribution pattern, which is the simplest method for the pattern analysis method, will be explained in simple terms hereinbelow.

If the angle range of the wavelength plate array and polarizer array is suitably chosen for the polarization analysis device in the case of either a wavelength angle variation-type polarization analysis device or a wavelength plate phase difference variation-type polarization analysis device, the bright spot and dark spot required for the observed intensity distribution pattern exist and the positions of the bright spot and dark spot depends on the incident polarized wave. Therefore, if the bright spot position or dark spot position can be detected, the polarization state can be specified. In reality, because a case where the intensity of the incident light fluctuates with time and a case where the beam profile of the incident light is not uniform over the whole range of the array may also be considered, it is clear that detecting the dark spot is more straightforward than detecting the bright spot. Therefore, although a case of dark spot detection is described hereinbelow, exactly the same theory is also established for a case of bright spot detection.

If the number of partitions of the wavelength plate array and polarizer array can, in theory, be increased without limit, the position of the dark spot in the observed intensity distribution pattern can be accurately known. However, because the number of partitions in an actual array is limited, an error corresponding to the number of partitions in the array depends on the position of the dark spot thus obtained. As an example, FIG. 8 shows simulation results of an intensity distribution when a linearly polarized wave in the horizontal direction enters in two different cases, namely when the principal axis angle of the wavelength plate array and polarizer array is changed 12° at a time from 0° to 180° (16 partitions) and 1° at a time (181 partitions), in a wavelength plate angle variation-type polarization analysis device. As illustrated, when there are 181 partitions, two dark spots (indicated by a white spot and an arrow) is found with an accuracy of ±1°. However, when there are 16 partitions, because the partitions are choppy, it is difficult to accurately find the dark spot positions. In order to improve the resolution of the dark spot positions, the greater the number of partitions of the array the better. However, when the actual fabrication and costs and so forth are considered, it is desirable to implement as small a partition number as possible.

Figure 9:
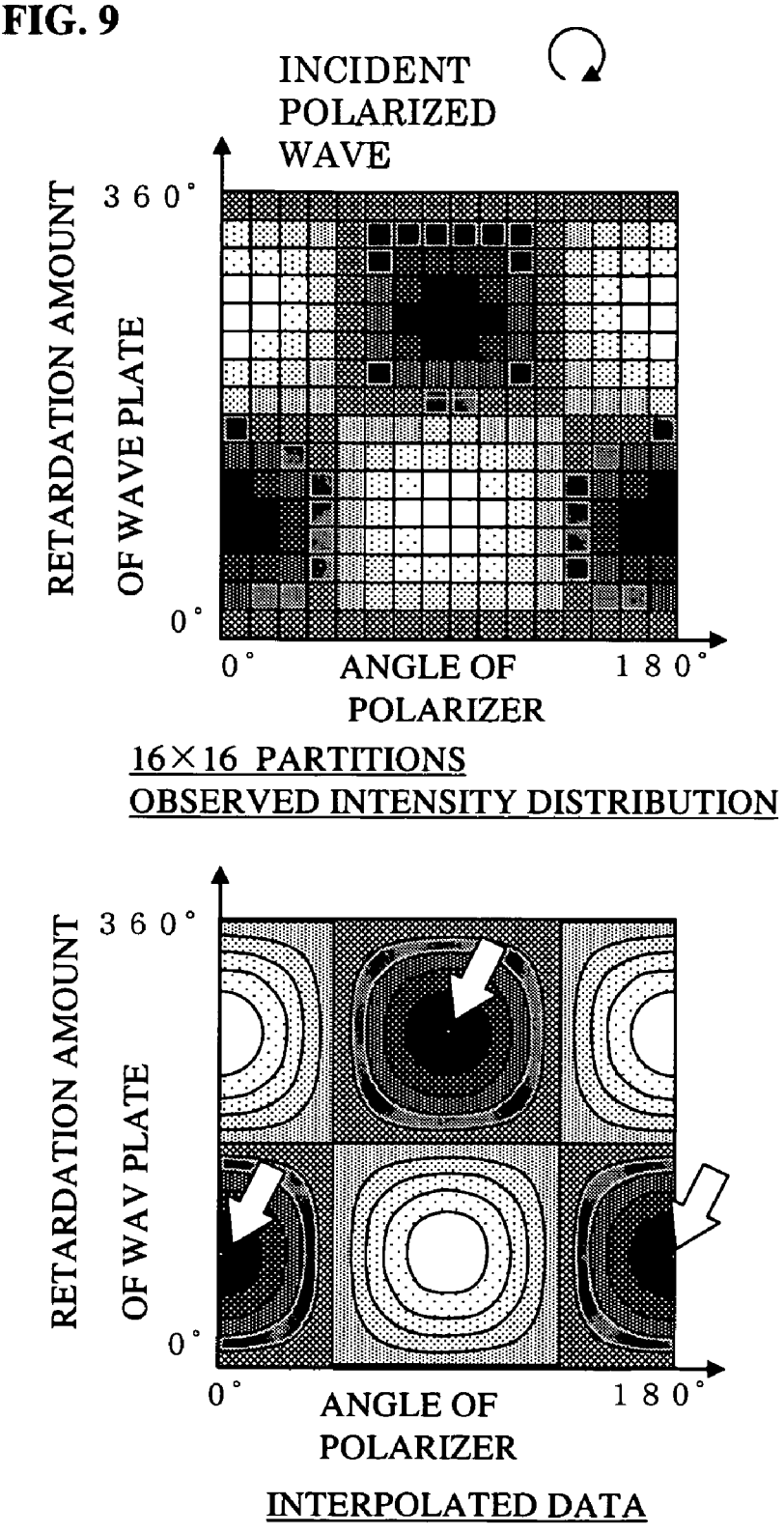
FIG. 9 is an example of the relationship between the observed intensity distribution pattern and the intensity distribution after interpolation.

In order to find the dark spot positions as accurately as possible with a small number of partitions, a method that interpolates the scattered intensity distribution observed and determines a continuous intensity distribution through calculation is effective. By way of example, a case where the wavelength plate array in a wavelength plate phase difference variation-type polarized wave analysis device has a principal axis angle that is 45° to the horizontal, the phase difference is change 24° at a time from 0° to 360° (16 partitions) and where the principal axis angle of the polarizer array is changed 12° at a time from 0° to 180° (16 partitions) may be considered. FIG. 9 shows simulation results of a continuous intensity distribution rendered by performing spline interpolation on the observed intensity distribution and the results obtained in a case where a clockwise circularly polarized wave enters the polarization analysis device. As can be seen from FIG. 9, it can be seen that, by interpolating the intensity distribution, a continuous intensity distribution is obtained that is also not inferior in comparison with a case where the array partition number is increased. Working from the interpolated data, it is possible to find a point of minimum intensity (indicated by a white spot) by means of an approximation calculation. Therefore, an accurate polarized wave state can be judged even with a small partition number. Because there is a correlation between the positional accuracy for the dark spot found using interpolation and the partition number of the array, the partition number of the array may be determined on the basis of the accuracy required of the device.

As mentioned earlier, with the dark spot detection method, a polarization state can be judged instantly on the basis of the relative intensity distribution of light detected by the light-receiving element array. Hence, information on the absolute value of the optical intensity is not required. This is characterized by performing relatively accurate polarization analysis even in a case where the incident light has an intensity distribution and when there are optical intensity fluctuations, and so forth, for example. However, dark spot detection is not flawless and, as also mentioned earlier, in cases where the retardation amount of the wavelength plate is not strictly a ¼ wavelength, for example, the measurement accuracy is poor because the dark spot position is shifted from the ideal position. In order to resolve this problem, the present invention provides two methods, namely, the 'Fourier analysis method and 'pattern shape fitting method' as the polarized wave analysis method.

Figure 5:
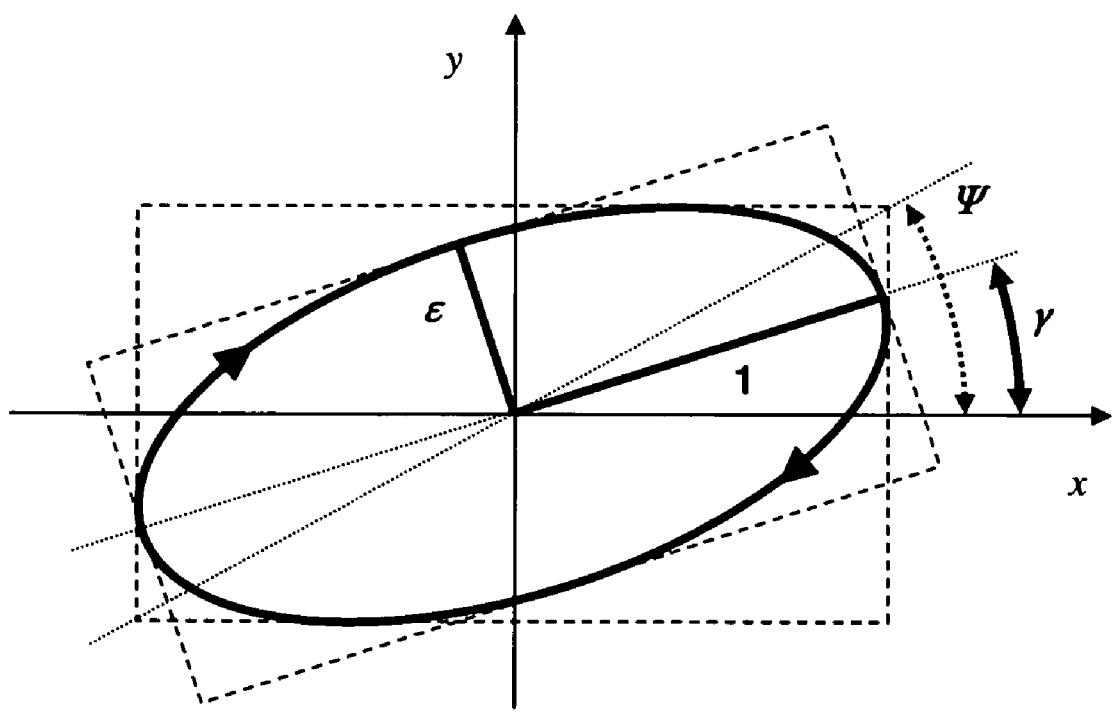
FIG. 5 is a conceptual view of a method of representing the polarization state of light.
Figure 10:
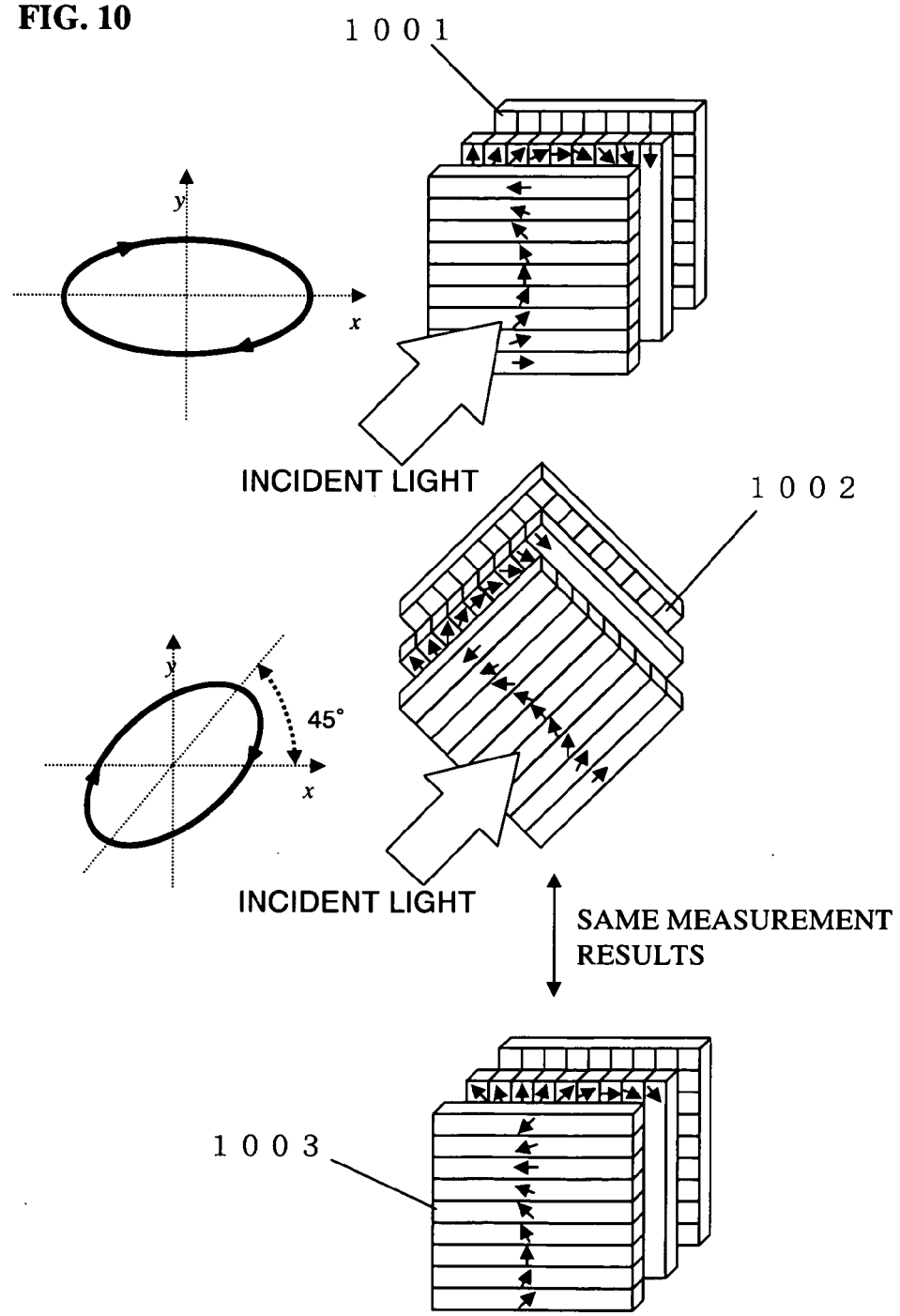
FIG. 10 is a conceptual view of the relationship between the tilt of the incident polarized wave and the observed intensity distribution pattern.
Figure 11:
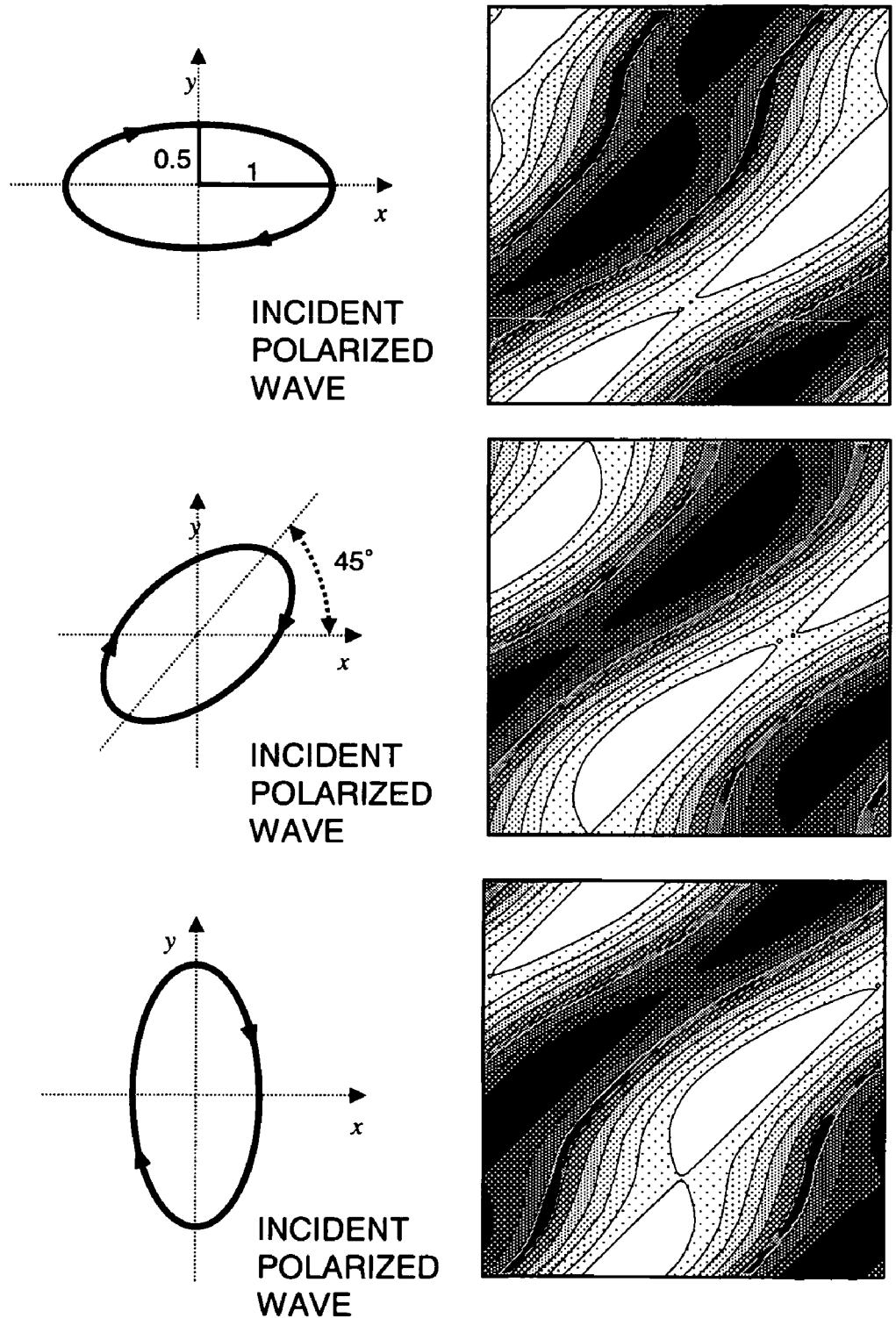
FIG. 11 is an example of the observed intensity distribution pattern (relationship with the ellipticity of the incident polarized wave)

Before these pattern shape analysis procedures are described, the characteristics of pattern shapes observed by means of a light-receiving element array will be explained simply. As also indicated by Equations 3 and 4 that describe FIG. 5, the optical intensity distribution observed by the polarization analysis device used by the present invention can be expressed as a function of the ellipticity ($\epsilon$) and elliptical tilt ($\gamma$) of the incident light. Here, the tilt ($\gamma$) of the ellipse is defined with a certain axis direction (the horizontal direction in this case) serving as the reference but the direction of the reference axis is optional. Therefore, changing the tilt ($\gamma$) of the ellipse is equivalent to changing the adoption of a reference axis, that is, the arrangement order of the respective regions of the wavelength plate array and the polarizer array. For example, as shown in FIG. 10, the intensity distribution obtained in cases where the ellipticity of the incident polarized light is constant (the value of $\epsilon$ is optional) and a polarization analysis device 1001 is disposed horizontally when the tilt of the ellipse is 0°, and the result observed when a polarization analysis device 1002 is disposed at 45° in the same way when the tilt of the ellipse is 45 degrees are exactly the same. The measurement results obtained by the polarization analysis device 1002 and the measurement results obtained by the polarization analysis device 1003 are the same. This corresponds to a case where the arrangement order of the wavelength plate array and the polarizer array of the polarization analysis device 1001 are interchanged. As detailed earlier, it can be seen that, when the tilt of the polarized wave of the incident light is changed, the intensity distribution pattern observed moves horizontally within the plane and the corrugated shape of the pattern does not change. By way of example, FIG. 11 shows the observed optical intensity distribution when the ellipticity of the incident light is constant ($\epsilon$=0.5) and the angle ($\gamma$) of the ellipse is changed to 0°, 45°, and 90°.

Figure 13:
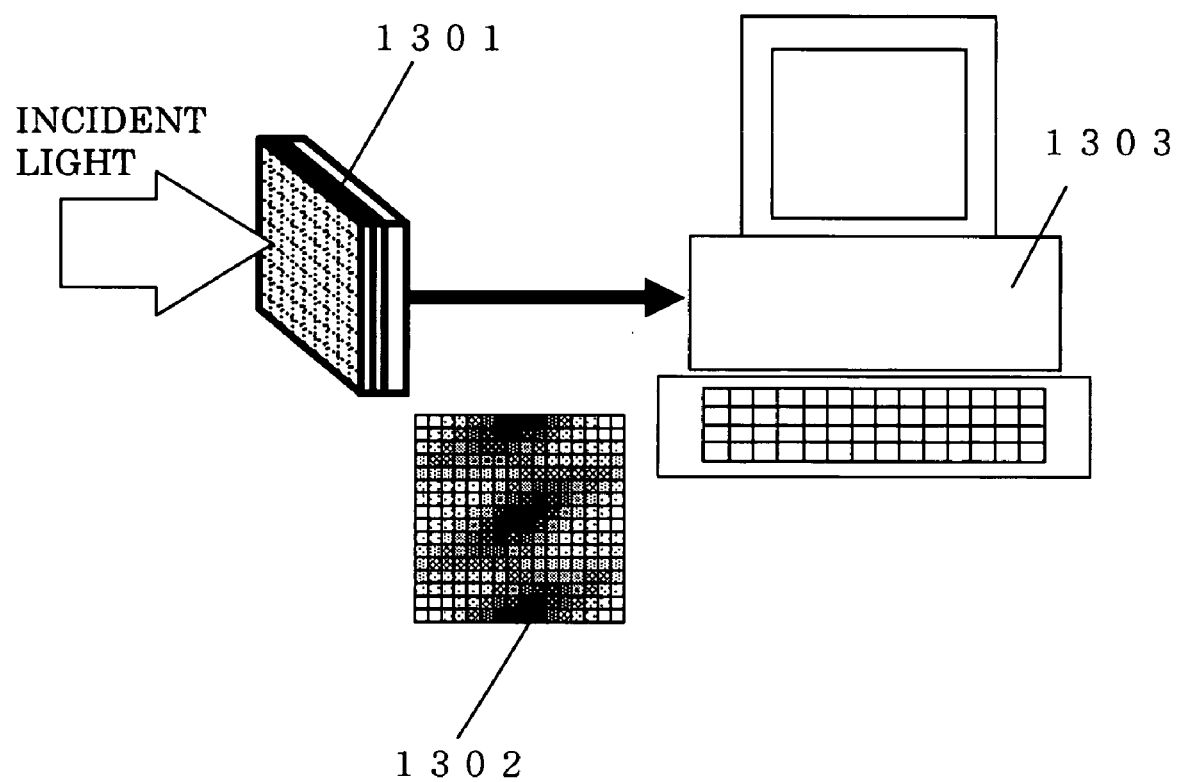
FIG. 13 is a constitutional example of a polarization analysis system that analyzes an intensity distribution pattern.

On the other hand, a change in the pattern shape when the ellipticity of the incident light is changed can be easily conceived. By way of example, FIG. 12 shows the observed optical intensity distribution when the tilt of the incident light is fixed at $\gamma$=0° and the ellipticity $\epsilon$ is changed to 0 (linear polarization), 0.2, 0.5, 1 (clockwise circularly polarized light). When the incident light is linearly polarized light, the pattern is a 'ship's bottom-type' cyclical shape, whereas the pattern shape is extended as the ellipticity increases. In the case of circularly polarized light, a limited linear cyclical shape rendered by extending the ellipse limitlessly is produced. As mentioned hereinabove, it is clear that the ellipticity ($\epsilon$) of the incident polarized light can be found from the corrugated shape of the optical intensity distribution pattern observed by the light-receiving element array and the tilt ($\gamma$) of the incident polarized light can be determined from the relative position (coordinates) in the plane of the pattern. FIG. 13 shows a constitutional example of a device for implementing the polarization analysis method or polarization analysis system of the present invention. An optical intensity distribution 1302 that is observed by a polarization analysis device 1301 that employs a wavelength plate array and a polarizer array is received by a CPU1303 and the two-dimensional pattern shape of the optical intensity distribution 1302 is analyzed. The polarization analysis method in each case will be explained hereinbelow.

First, as an example of a polarized wave analysis method that uses fitting of the optical intensity distribution indicated by claim 18, a polarization analysis algorithm that analyzes the contour shape of the observed intensity distribution pattern will be described. The contour shape of the intensity distribution can be found simply by extracting points of equal intensity form the observed intensity distribution data. Here, when the number of partitions of the wavelength plate array and polarizer array is small, a method that calculates the contour shape after finding a smooth intensity distribution by interpolating the observed scattered values by means of a fitting calculation is effective in order to obtain a more accurate contour shape. The contour may be found for the whole area of the observed intensity distribution pattern as shown in FIGS. 11 and 12 but may also be found for only a bright spot neighborhood or dark spot neighborhood in which the characteristics of the pattern are most favorably observed. If the shape and position of the contour thus found can be analyzed, the polarization state of the incident light can be found as mentioned earlier. Here, as examples of procedures for analyzing the shape of the contour, a method for analyzing the tilt and position of the contour shape of a pattern dark spot (minimum value) neighborhood and a method for a comparison with a pre-prepared pattern database will be described in simple terms.

Figure 14:
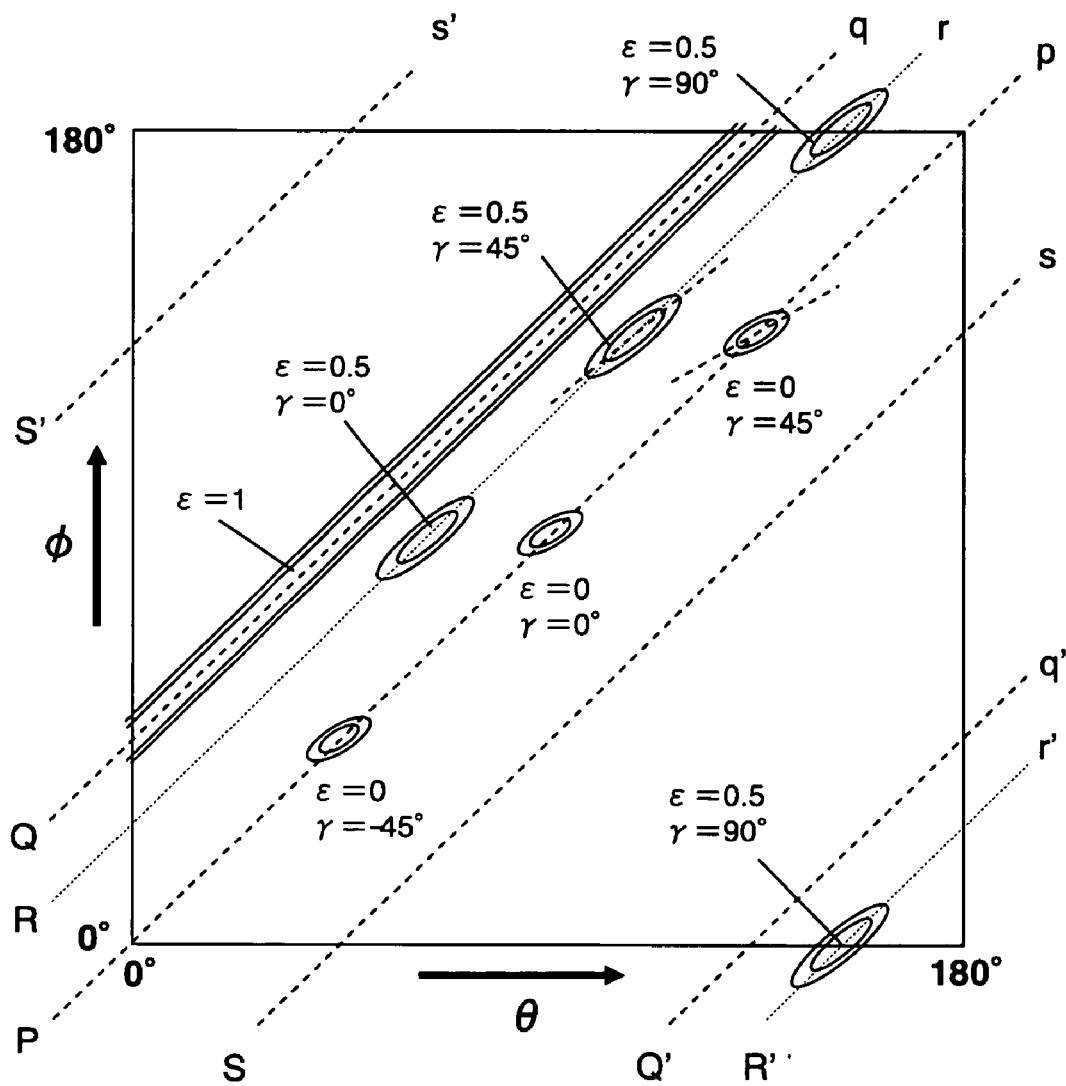
FIG. 14 shows the contour shape in the vicinity of the dark spot of the observed intensity distribution pattern.

First, the method for detecting the tilt and position of the contour will be described. By way of example, the results of rendering a contour only of the dark spot neighborhood of the observed intensity distribution pattern are shown together in FIG. 14 for cases where the incident light is linearly polarized light ($\epsilon$=0), clockwise circularly polarized light ($\epsilon$=1), and clockwise elliptically polarized light ($\epsilon$=0.5) shown earlier in FIGS. 4 and 11. Generally, when the principal axis angle range of the wavelength plate array and polarizer array is from 0° to 180°, a dark spot exists in two locations within the plane. However, because confusion is avoided in FIG. 14, only a representative dark spot neighborhood contour is displayed. This can also be seen from FIG. 14 but the contour shape of the dark spot neighborhood is substantially elliptical and the shape can be expressed as Equation (5):

$$A(\phi-\phi_0)^2+B(\phi-\phi_0)(\theta-\theta_0)+C(\theta-\theta_0)^2+D=0 \qquad \text{(Equation 5)}$$

Here, A, B, C, and D are constants. It is clear that, when the ellipticity ($\epsilon$) of the incident polarized wave is fixed, the position of the dark spot exists on a specified straight line that is determined by the ellipticity. For example, in the case of linearly polarized light ($\epsilon$=1), the dark spot exists on a straight line P-p, in the case of clockwise circularly polarized light, the dark spot exists on a straight line Q-q or Q'-q', and in the case of elliptically polarized light where $\epsilon$=0.5, the dark spot position exists on a straight line R-r or R'-r'. Further, although not illustrated, the dark spot position when counterclockwise circularly polarized light enters the device exists on the straight line S-s or S'-s' in symmetry with when clockwise circularly polarized light enters the device. It can be seen that, when the tilt ($\gamma$) of the incident polarized light changes, the dark spot position moves onto the straight line determined by the ellipticity ($\epsilon$).

It is also clear that the tilt of the ellipse obtained as the contour of the dark spot neighborhood varies according to the ellipticity of the incident light. Although the contour in the case of circularly polarized light is a limited linear shape the ellipse of which is infinitely long and narrow, the tilt of the locus of the minimum value is 1 and, as the ellipticity decreases, so does the tilt of the ellipse of the contour. By using this fact, the polarization state of the incident light can also be determined. In any event, if the contour shape of the intensity distribution pattern observed by the polarization analysis device can be fitted by means of Equation 5 above, the tilt and position can be accurately found and, therefore, the polarization state ($\epsilon$ and $\gamma$) of the incident light can be accurately found.

Figure 15:
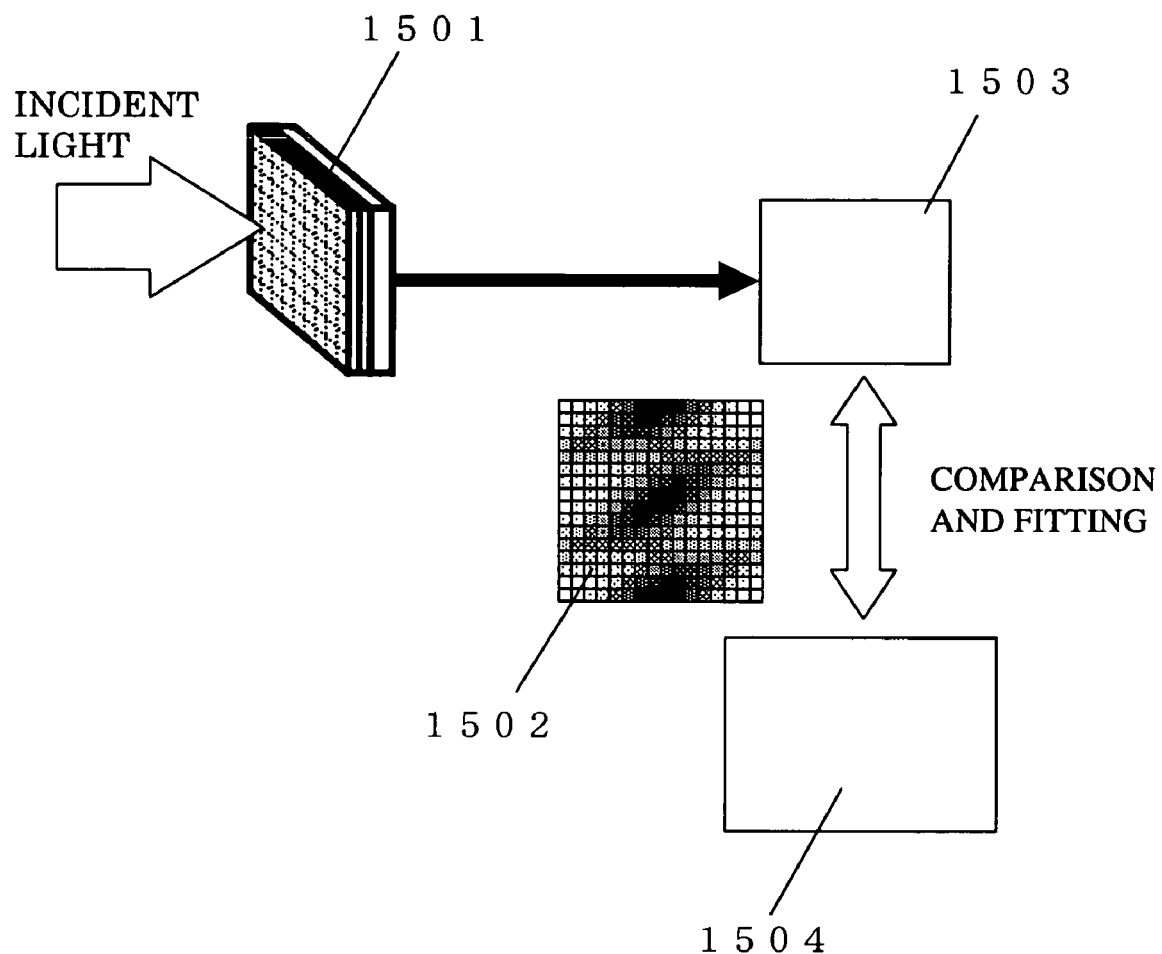
FIG. 15 is a conceptual view of a polarization analysis method that compares a pattern shape with a database.

As another example of a contour shape analysis method, FIG. 15 shows a procedure that compares the pattern shape thus found with a database. In this case, a database is made beforehand using pattern shapes corresponding with various polarized wave states, an intensity distribution pattern observed by the polarization analysis device 1501 is converted to contour data by the CPU 1502 and compared with the pattern shapes that have accumulated in a database 1503, and the polarization state of the incident light is found by searching for matching data. Naturally, the procedure for detecting the position and tilt of the contour mentioned earlier and the procedure for a database comparison are performed at the same time, whereby more accurate polarization analysis can also be performed.

A polarization analysis algorithm (Fourier analysis method) for performing a Fourier transform on an observed intensity distribution pattern to find the frequency component that is illustrated in claim 19 will be described next. When the equations (Equations 3 and 4) for the optical intensity distribution observed by the polarization analysis device used by the present invention are described once again, $$\vec{u} = \begin{pmatrix} 1 & 0 \\ 0 & 0 \end{pmatrix} \begin{pmatrix} \cos(\phi-\theta) & \sin(\phi-\theta) \\ -\sin(\phi-\theta) & \cos(\phi-\theta) \end{pmatrix} \begin{pmatrix} e^{j\alpha} & 0 \\ 0 & 1 \end{pmatrix} \begin{pmatrix} \cos(\theta-\gamma) & \sin(\theta-\gamma) \\ -\sin(\theta-\gamma) & \cos(\theta-\gamma) \end{pmatrix} \begin{pmatrix} 1 \\ j\varepsilon \end{pmatrix} \quad \text{(Equation 6)}$$

and $$|\vec{u}|^2 = \vec{u}^* \cdot \vec{u} \quad \text{(Equation 7)}$$

When these equations are normalized by the incident light intensity by modifying these equations, $$|\vec{u}|^2 \cdot \frac{1}{1+\varepsilon^2} = \frac{1}{2} + \quad \text{DC component} \quad \text{(Equation 8)}$$
$$\frac{1}{4} \cdot \frac{1-\varepsilon^2}{1+\varepsilon^2}(1+\cos\alpha)\cdot\cos(\Phi-2\gamma) + \quad X$$
$$\frac{1}{4} \cdot \frac{1-\varepsilon^2}{1+\varepsilon^2}(1-\cos\alpha)\cdot\cos(2\Theta-\Phi-2\gamma) + \quad Y$$
$$\frac{\varepsilon}{1+\varepsilon^2}\sin\alpha\cdot\sin(\Theta-\Phi) \quad Z$$

are obtained. Here, the substitutions $2\phi=\Phi$ and $2\theta=\Theta$ are made for the purpose of simplification. Equation 8 shows that the observed two-dimensional intensity distribution consists of three frequency components which are $\Phi$, $2\Theta-\Phi$, and $\Theta-\Phi$. In the case of X, Y, and Z, which show the respective frequency components in Equation 8, it is clear that, when the incident light is linearly polarized light ($\varepsilon=0$), Z=0, and when the incident light is linearly polarized light ($\varepsilon=1$), X=Y=0. Further, because the tilt ($\gamma$) of the incident light is expressed as the phase of X and Y, it can be seen that the amplitude of the respective frequency components, that is, the shape of the intensity distribution does not change even when $\gamma$ has changed, which conforms to the earlier mentioned results.

It is clear from Equation 8 that if the spectral can be calculated by performing a Fourier transform on the intensity distribution observed by the polarization analysis device and the amplitude and phase of the respective frequency components can be found, the polarization state of the incident light can be accurately found. That is, when the values of the respective frequency components X, Y, Z are known, the tilt ($\gamma$) of the incident polarized light can be found as ½ the value of the phase of X or Y as indicated by $$\gamma = (\text{phase of X})/2 \text{ or } \gamma = (\text{phase of Y})/2 \quad \text{(Equation 9)}$$

and the ellipticity ($\epsilon$) of the incident light can be found from the value of the amplitude of Z as Equation (10):

$$\varepsilon = \frac{\sin\alpha - \sqrt{\sin^2\alpha - 4(\text{amplitude of } Z)}}{2(\text{amplitude of } Z)} \quad \text{(Equation 10)}$$

As an example of the polarization analysis using a Fourier transform, FIGS. 17 and 18 show an intensity distribution observed by a light-receiving element array, the results of performing a Fourier transform on this intensity distribution, and the results of back-calculating the incident polarized light state from the respective frequency components found by means of the Fourier transform for cases where the ellipticity of the incident polarized wave is changed and the tilt is changed (FIGS. 11 and 12). The illustrated results are produced by analyzing the intensity distribution in a case where the wavelength plate array and polarizer array of the polarization analysis device are divided into 64 and the principal axis is changed 2.8125° at a time from 0° to 180° (accurately speaking, up to 177.1875°). Further, the respective frequency components determined by the Fourier transform are normalized by the incident light intensity. As is clear from the results, it can be seen that the polarization state obtained by back-calculating from the values of the respective frequency components thus obtained conform to the incident polarized light.

However, in the case of an actual polarization analysis device, in addition to the effects of stray light from the outside, noise is superposed on the observed intensity distribution, which is caused by a variety of electrical noise. Further, when the optical response of the light-receiving element array is nonlinear, a correct intensity distribution is not obtained. Therefore, there can be cases of large errors in the polarization state found simply by means of the fitting calculation and Fourier analysis. Even in such a case, by combining both the contour analysis method and Fourier analysis method as illustrated by claim 20, more accurate polarization analysis can be implemented. For example, if an accurate contour shape can be found by finding a first-order approximation value for the pattern shape of the dark spot neighborhood of the pattern from the results of the Fourier analysis of the intensity distribution pattern containing noise and fitting sample values by using the approximation value, the polarization state of the incident light can be determined highly accurately.

Furthermore, as a noise countermeasure of the polarization analysis device, a method that combines usage of a polarization analysis method that uses contour analysis and Fourier analysis methods and a method (quenching method) that detects the positions of the minimum value (dark spot) of the pattern constituting the conventional polarization analysis method is effective. As described earlier, a quenching method is an extremely simple polarization analysis method that makes it possible to find the state of incident polarized light instantly from coordinate information of one point (minimum point, for example) in an intensity distribution pattern. If an intensity distribution pattern for a dark spot neighborhood can be precisely fitted with the observed sample values by using information on a first-order approximate position for a dark spot and on the shape of a second-order curve of an intensity distribution of the dark spot neighborhood that is obtained by performing a Fourier analysis of the whole of the observed intensity distribution pattern as shown in FIGS. 19C and 19D, for example, by using this quenching method, and if a second-order approximation value relating to the position of the dark spot can be accurately found, highly accurate polarization analysis is possible in comparison with a case of performing fitting of sample points without any information as (b) (although the measurement data is actually two-dimensional information, a one-dimensional case is shown in FIG. 19 for the sake of simplicity). In addition, when the shape of the whole pattern is analyzed, the optical intensity and measurement time (gate time) can be determined through consideration so that the light-receiving element array is not saturated even at a maximum value and, because there is no need to pay attention to the saturation of the maximum value when the focus is on the minimum value (dark spot), high S/N data can also be acquired for a relatively long time. With such a procedure, more accurate fitting is possible for the shape of the dark spot neighborhood, whereby the accuracy of analyzing the state of an incident polarized wave can be improved.

Examples of the present invention will be described next.

EXAMPLE 1

Figure 20:
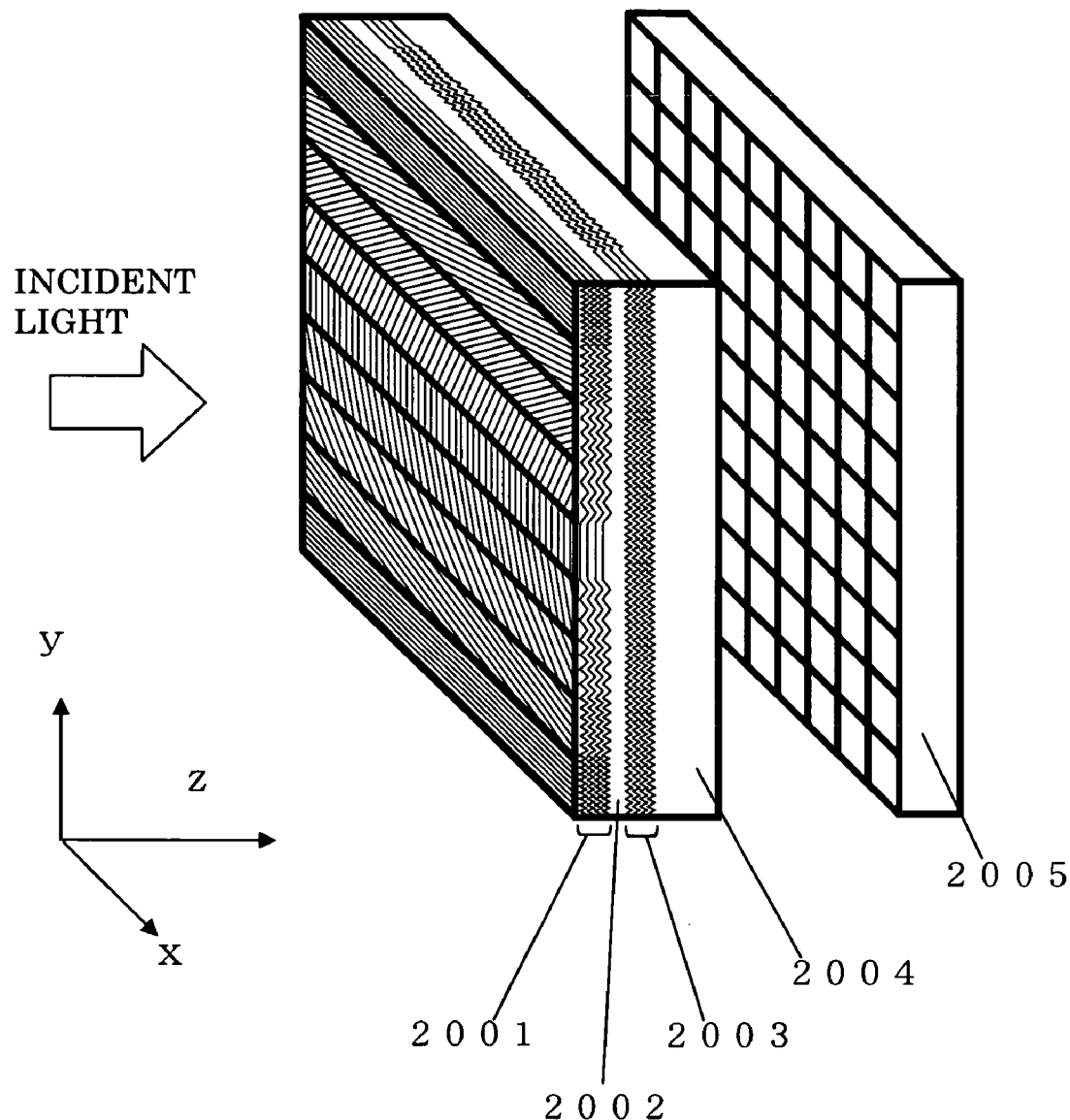
FIG. 20 is a conceptual view of a method for integrating a wavelength plate array and a polarizer array.

An example in which the wavelength plate array and polarizer array in the polarization analysis device of claims 1 to 6 are integrated is shown in FIG. 20. A polarizer array is created by forming a groove pattern on the substrate 2004 and depositing a multilayered film 2003 on the groove pattern of substrate 2004. A termination layer 2002 of the polarizer array layer is deposited quite thickly and, when sputter etching is performed strongly at the same time, the corrugated shape formed by autocloning is eliminated and a level surface is completed. There is no particular problem even when mechanical grinding is used to smooth the surface. Thereafter, a wavelength plate array is created by newly forming a wavelength plate line and space pattern by means of lithography and depositing a multilayered film 2001 by means of autocloning. For alignment of the patterns of the polarizer array and wavelength plate array, alignment markers may be placed on a portion of the substrate beforehand. Thus, if the polarizer array and wavelength plate array can be formed integrally, a smaller polarization analysis device can be implemented in combination with a light-receiving element array 2005.

EXAMPLE 2

Figure 21:
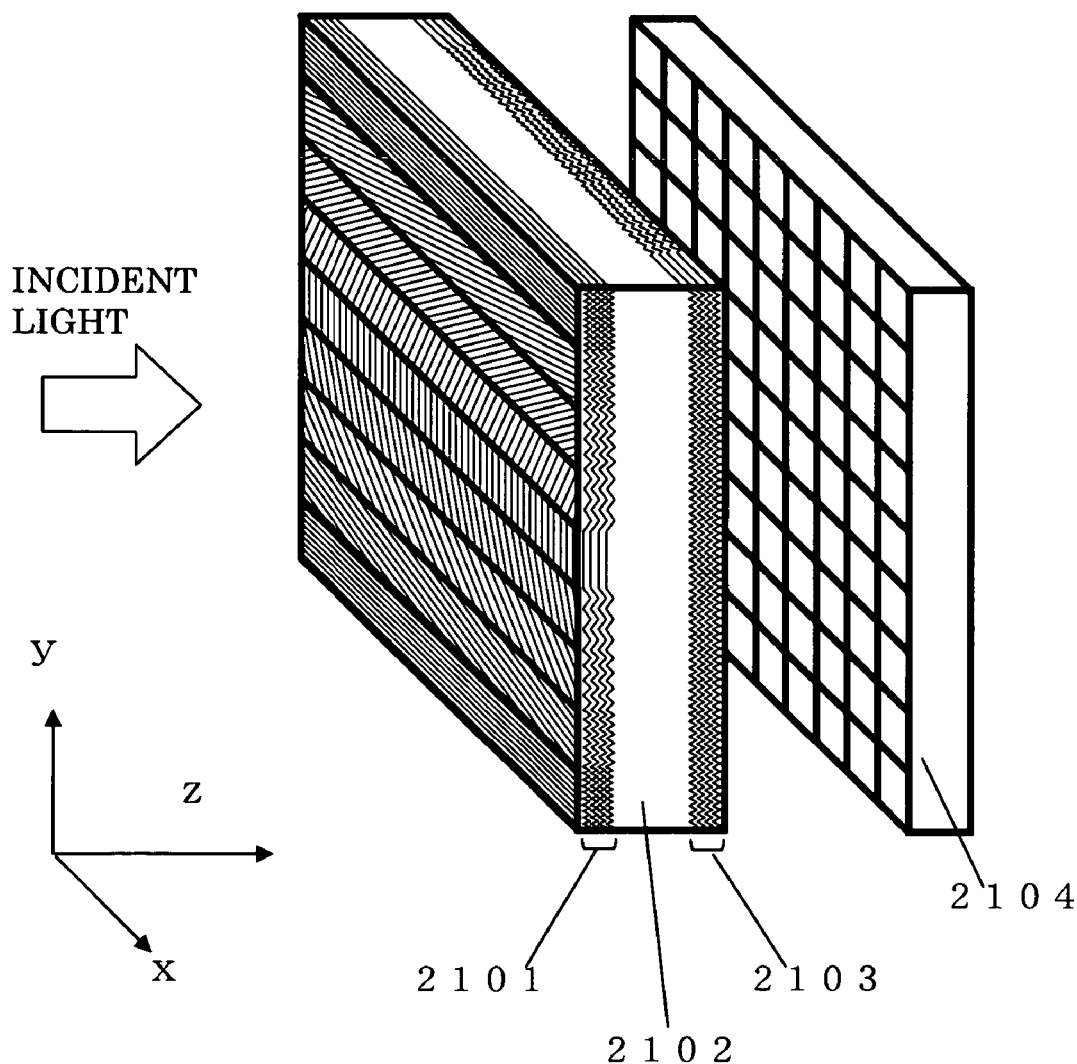
FIG. 21 is a conceptual view of a second method for integrating a wavelength plate array and a polarizer array.

FIG. 21 shows another example that integrates the wavelength plate array and polarizer array of the polarization analysis device of claims 1 to 6. In this case, integration can be implemented by forming a groove pattern on the upper and rear sides of a substrate 2102 and forming a wavelength plate array layer 2101 and a polarizer array layer 2103 by means of autocloning. For pattern alignment, a transparent substrate such as $SiO_2$ may be used for the substrate 2102 and alignment markers may be added to the substrate. A small polarization analysis device can be implemented by combining the integrated wavelength plate/polarizer array with a light-receiving element array 2104.

EXAMPLE 3

Although also clear from FIGS. 4 and 7, the position of zero intensity appears as a line rather than a spot when a certain specified polarized wave enters either a wavelength plate angle variation-type polarization analysis device or a wavelength plate phase difference variation-type polarization analysis device. For example, in the case of an angle variation-type polarization analysis device (FIG. 4), when clockwise or counterclockwise circularly polarized light enters the polarization analysis device, in the case of a phase difference variation-type polarization analysis device (FIG. 7), and when linearly polarized light of the same direction as the principal axis angle of the wavelength plate or of a direction orthogonal to the direction of the principal axis angle enters the polarization analysis device, the intensity distribution is linear. When dark spot detection is adopted as the polarization analysis algorithm, the bottom position (or peak position) of these singular points and the polarization state of the neighborhood of these singular points is no longer fixed to a point and judgment of the polarization state is difficult.

Figure 22:
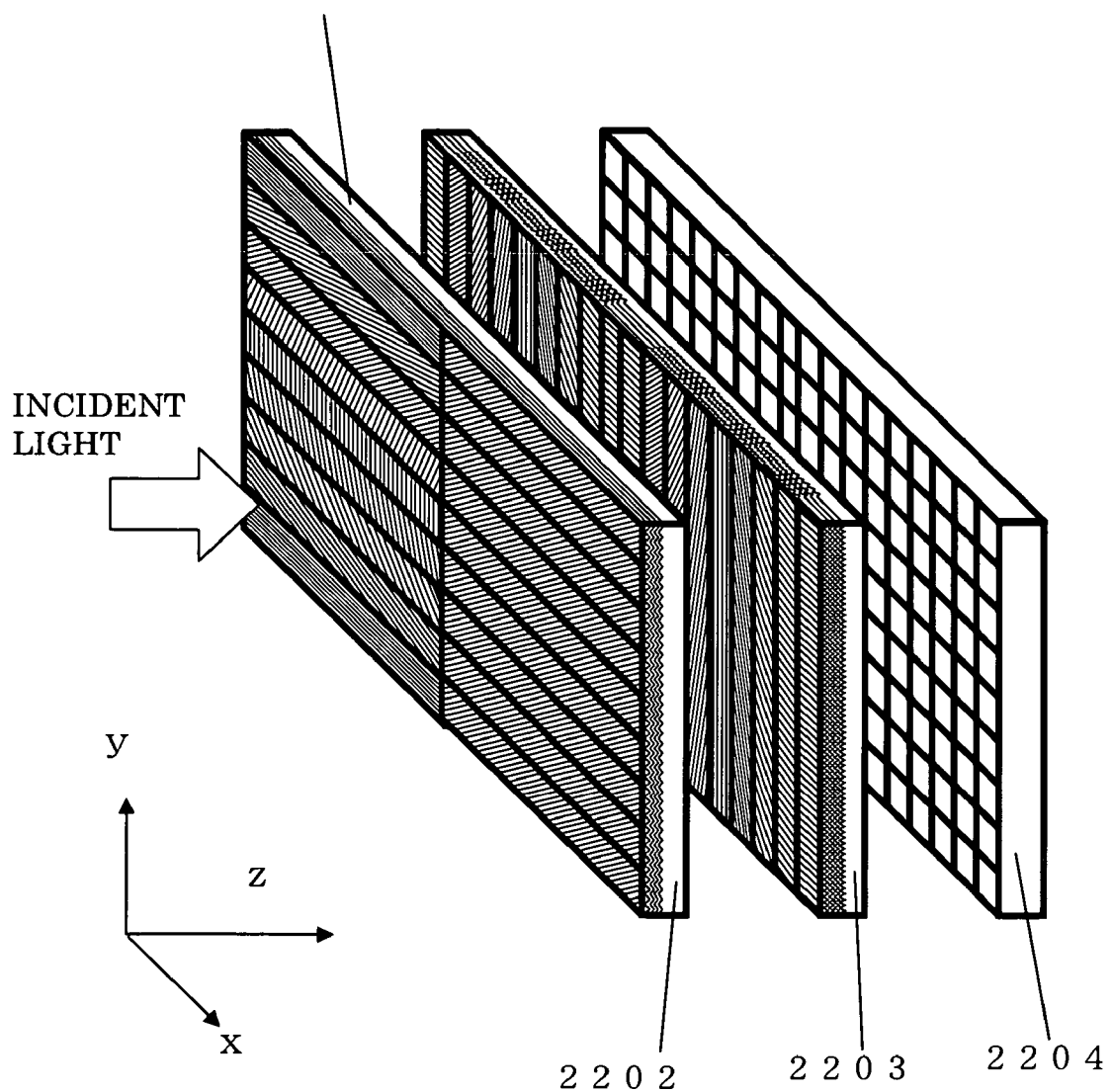
FIG. 22 is a conceptual view of a polarization analysis device produced by integrating the polarization analysis devices of FIGS. 3 and 6.

Therefore, a method for combining and complementarily using a wavelength plate angle variation-type polarization analysis device and a wavelength plate phase difference variation-type polarization analysis device is shown in FIG. 22 as the example of claim 7 of the present invention. A principal axis angle variation-type ¼ wavelength plate array 2201 and a retardation amount (phase difference) variation-type wavelength plate array 2202 are formed on the same substrate and combined with a polarizer array 2203, and the optical intensity distribution is measured by an optical detector array 2204. Because a variety of patterns can be made by means of the same process by means of an autocloning-type photonic crystal, complicated patterns such as those illustrated can also be easily made. Although respective regions are lined up in the y axis direction in the drawings, the positions and order for arranging the respective regions are optional. In this case, even when the intensity distribution is linear in one region and the judgment of polarization states is difficult, the zero point position can be accurately found in another region. Hence, the judgment of all the polarized wave states can be performed without problems. The present invention is advantageous on account of being able to perform implementation by means of an adequately small-scale and simple process by using a photonic crystal even in the case of a complicated constitution of this kind.

EXAMPLE 4

Figure 23:
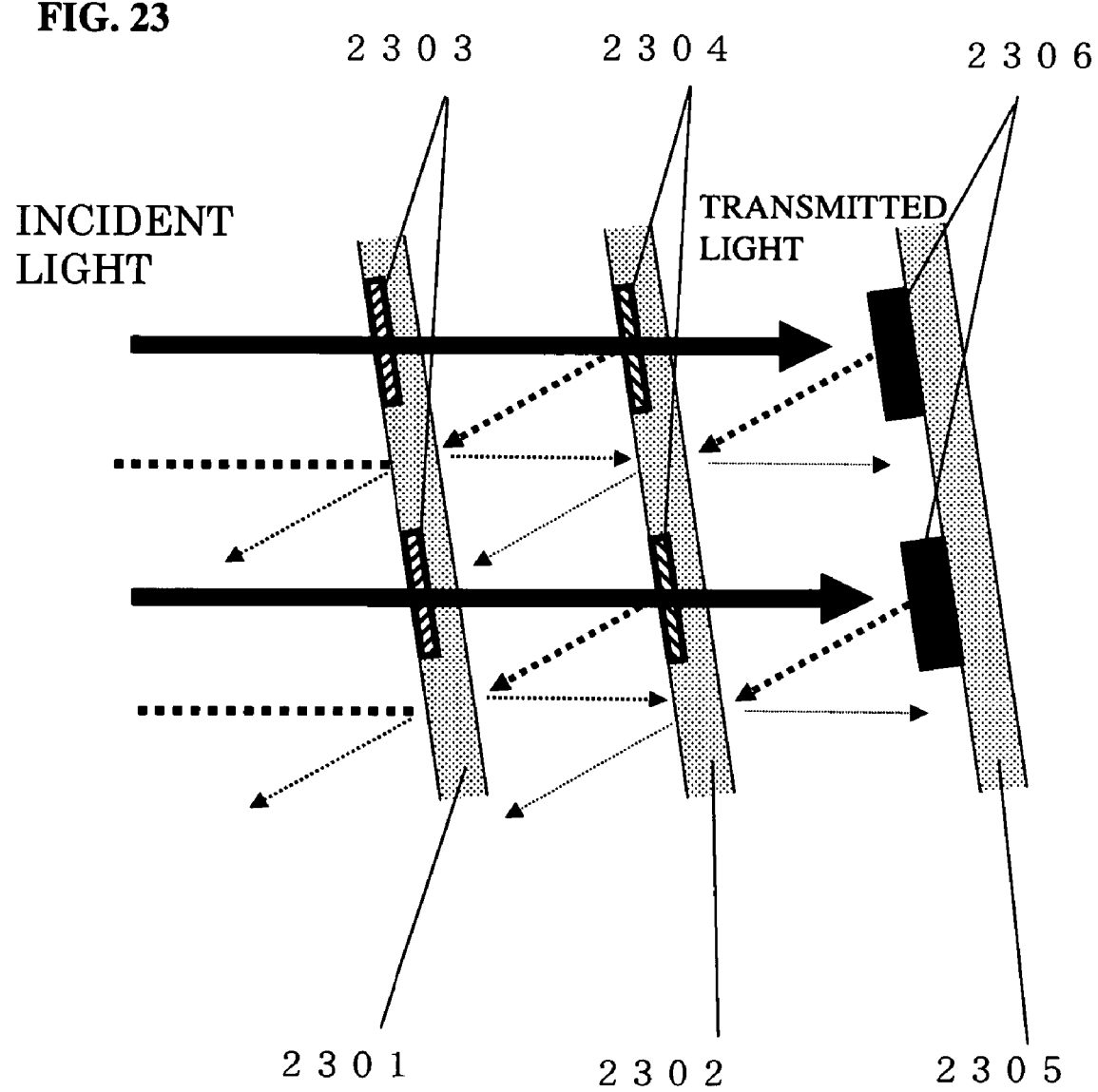
FIG. 23 is a conceptual view of a method that suppresses multiple echo of light in the polarization analysis device.

The polarization analysis device of claims 1 to 7 is a device constituted by a combination of three planar devices of a polarizer array, a wavelength plate array, and a light-receiving element array and there is therefore the possibility of the problem of multiple reflection of light between the polarizers, wavelength plates, and light-receiving elements. One of the examples of claim 8 is shown in FIG. 23 as a method for avoiding the effects of multiple reflection. FIG. 23 shows a cross-section of a wavelength plate array 2301, a polarizer array 2302, and a light-receiving element array 2305. In this case, a groove pattern area 2303 is formed at fixed intervals on the wavelength plate array 2301 and only the region where the groove pattern exists is the region that functions as the wavelength plate. Other regions without grooves are simple multilayered films that are transparent or nontransparent to light. Similarly also for the polarizer array substrate 2302, a polarizer pattern 2304 is formed in only one part, while the other regions are transparent or nontransparent to light. The two sheets of the wavelength plate array and polarizer array are combined with a light-receiving element array and arranged oriented in the direction of incidence of the light. As illustrated, by suitably selecting the pitch of the groove pattern and the interval and insertion angle of the two arrays, a component detected by a light-receiving element after undergoing multiple reflection between the respective layers in the light that is reflected by the polarizer array can be markedly reduced.

EXAMPLE 5

Figure 24:
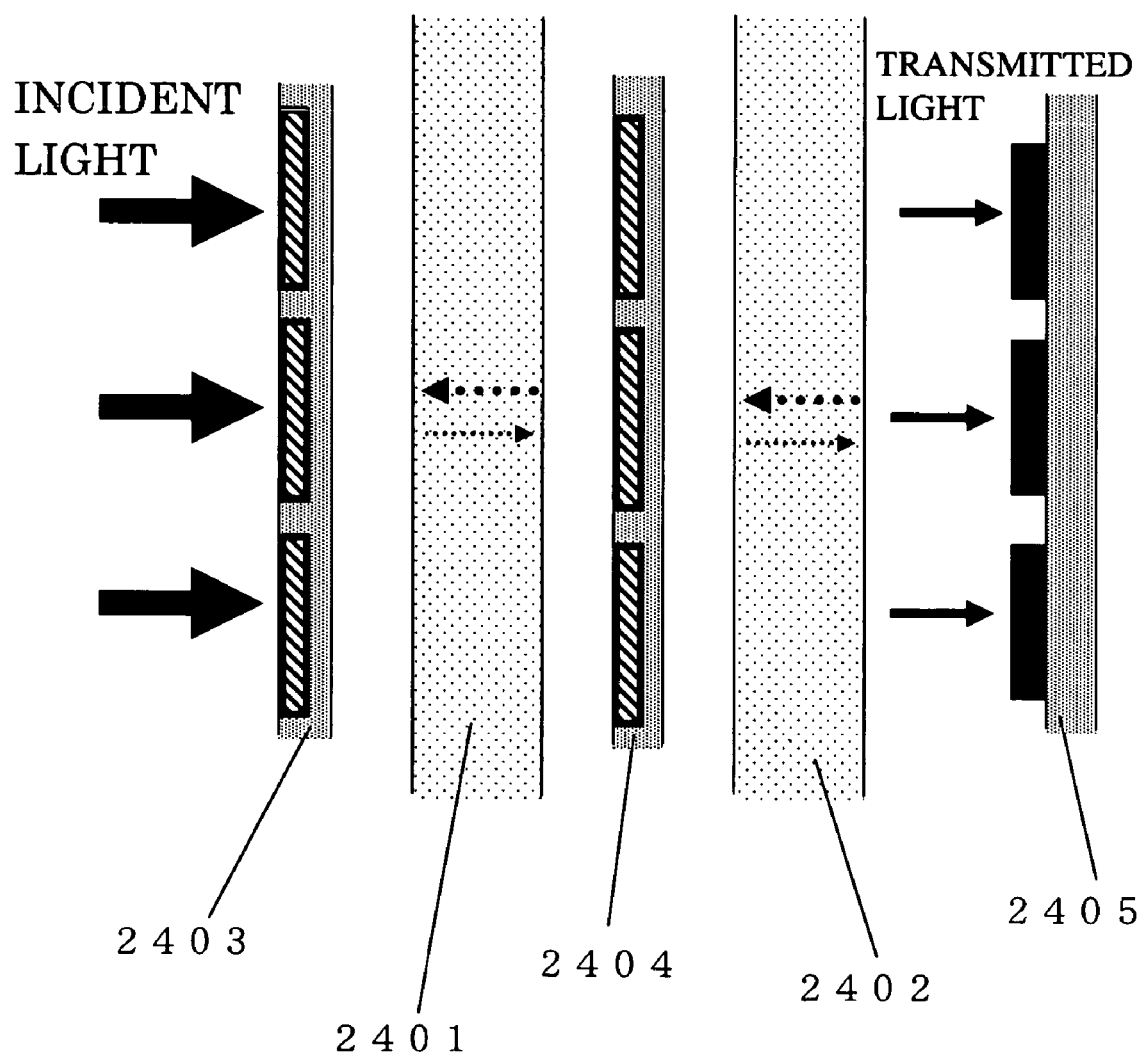
FIG. 24 is a conceptual view of a second method that suppresses multiple echo of light in the polarization analysis device.

FIG. 24 shows another example of the method for reducing the effects of multiple reflection of light between the wavelength plate array, polarizer array, and light-receiving element array of claim 8. This is a structure rendered by disposing light-absorbing substrates 2401 and 2402 between a wavelength plate array 2403 and polarizer array 2404 or between a wavelength plate array 2404 and a light-receiving element array 2405. A case where these elements are integrated by means of a method of fabrication that sticks the elements together and deposits the elements on one substrate is also the same. With such a constitution, the optical transmission intensity is weak but the intensity of the incident light is normally considered to be sufficiently strong in comparison with the sensitivity of the optical detector and there is therefore no problem in practice. The light reflected by the polarizer array 2404 and the light-receiving element array 2405 and so forth is absorbed after being propagated within the absorption layers 2401 and 2402 and gradually weakens. Hence, the component that is re-reflected and detected by the detector can be sufficiently small.

EXAMPLE 6

Figure 25:
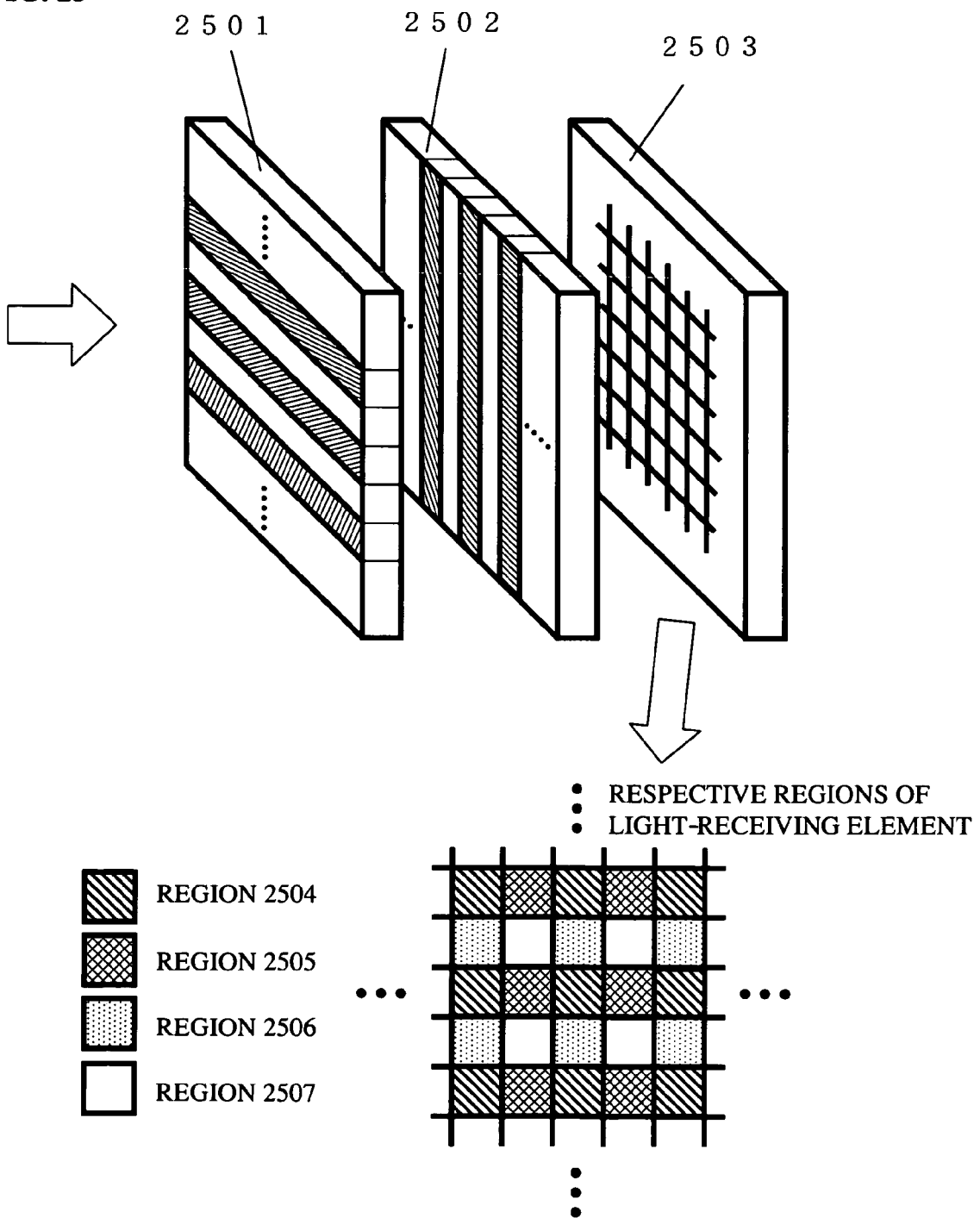
FIG. 25 is a constitutional example (1) of a polarization analysis device that corrects an incident light intensity distribution and loss distribution.

As an example of claim 9, FIG. 25 shows an embodiment in which a transparent region is provided between the respective regions of the wavelength plate array and polarizer array and the incident light intensity distribution and a distribution for the loss of the wavelength plate array and the polarizer array are measured. The respective regions of a wavelength plate array 2501 are arranged spaced apart from one another and the respective regions of a polarizer array 2502 are similarly arranged spaced apart from one another. Patternless regions of the polarizer array or wavelength plate array are designed to be transparent with respect to light. When a photonic crystal is used, complex structures such as those illustrated can also be created easily by means of a single process. When the wavelength plate array and polarizer array are combined with a light-receiving element array 2503, the respective light-receiving elements can be classified into a region 2504 that measures light components transmitted by both the wavelength plate and the polarizer, a region 2005 that measures the light transmitted by only the wavelength plate, a region 2506 that measures light transmitted by only the polarizer, and a region 2507 that measures light that is not transmitted by either the wavelength plate or polarizer (light transmitted by a transparent region). The intensity distribution information of the incident light can be determined from the optical intensity distribution measured by region 2507. Similarly, the loss distribution of the wavelength plate array can be evaluated from the intensity distribution measured by region 2505 and the loss distribution of the polarizer array can be evaluated from the intensity distribution measured by region 2506. By using such data, the intensity distribution measured by measurement region 2504 can be corrected, whereby highly accurate polarized wave analysis is possible.

EXAMPLE 7

Figure 26:
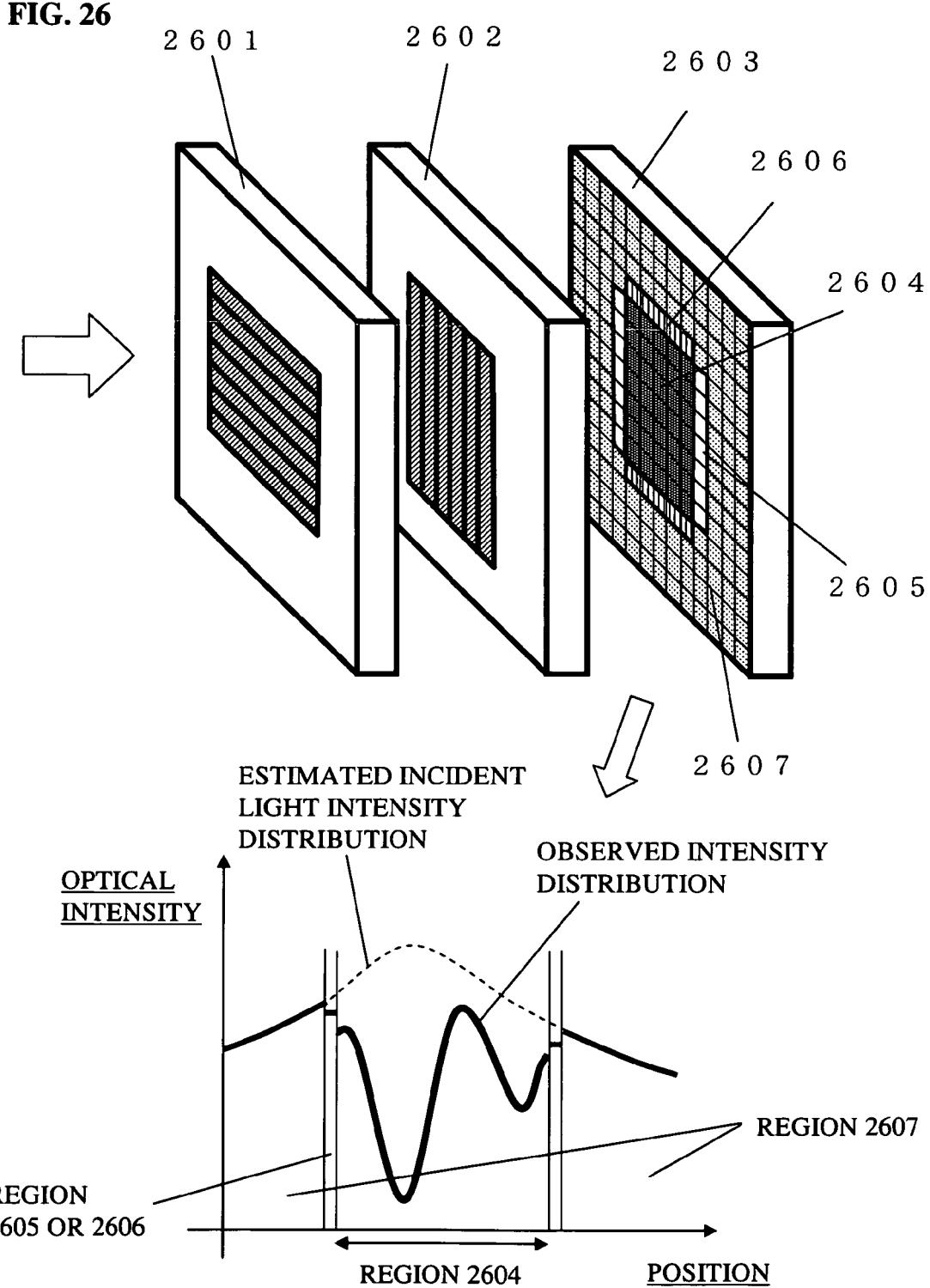
FIG. 26 is a constitutional example (2) of a polarization analysis device that corrects an incident light intensity distribution and loss distribution.

As a second example of claim 9, FIG. 26 shows an example in which a transparent region is provided at the circumference of the wavelength plate array and polarizer array. The part that functions as a wavelength plate in a wavelength plate array 2601 is only a certain region of the cyclical pattern of the center neighborhood and the other peripheral regions are transparent regions. Similarly, only the center neighborhood of a polarizer array substrate 2602 functions as a polarizer and the peripheral regions are transparent regions. Such a complex pattern can also be formed simply by using a photonic crystal technology. The polarizer array and wavelength plate array each have a rectangular shape, the ends of the pattern do not overlap each other when two arrays are overlapped, and light transmitted by both or only one of the arrays also reaches the light-receiving element. In this case, a region 2604 of a light-receiving element array 2603 measures the intensity distribution of light transmitted by both the wavelength plate and the polarizer. Light that is transmitted by only the wavelength plate in a region 2605 and light that is transmitted by only the polarizer in a region 2606 are received and the intensity of light that is not transmitted by either the polarizer or the wavelength plate in a region 2607 is measured. The loss distribution of the wavelength plate array is known from the measurement results for region 2605 and the loss distribution of the polarizer array is known through measurement of the region 2606. Further, because the incident light is normally considered to be a Gaussian beam the beam profile of the incident light can also be evaluated from the measurement results of region 2607. By using the loss distribution thus obtained and the intensity distribution of the incident light, highly accurate correction of measurement data is possible.

EXAMPLE 8

Figure 27:
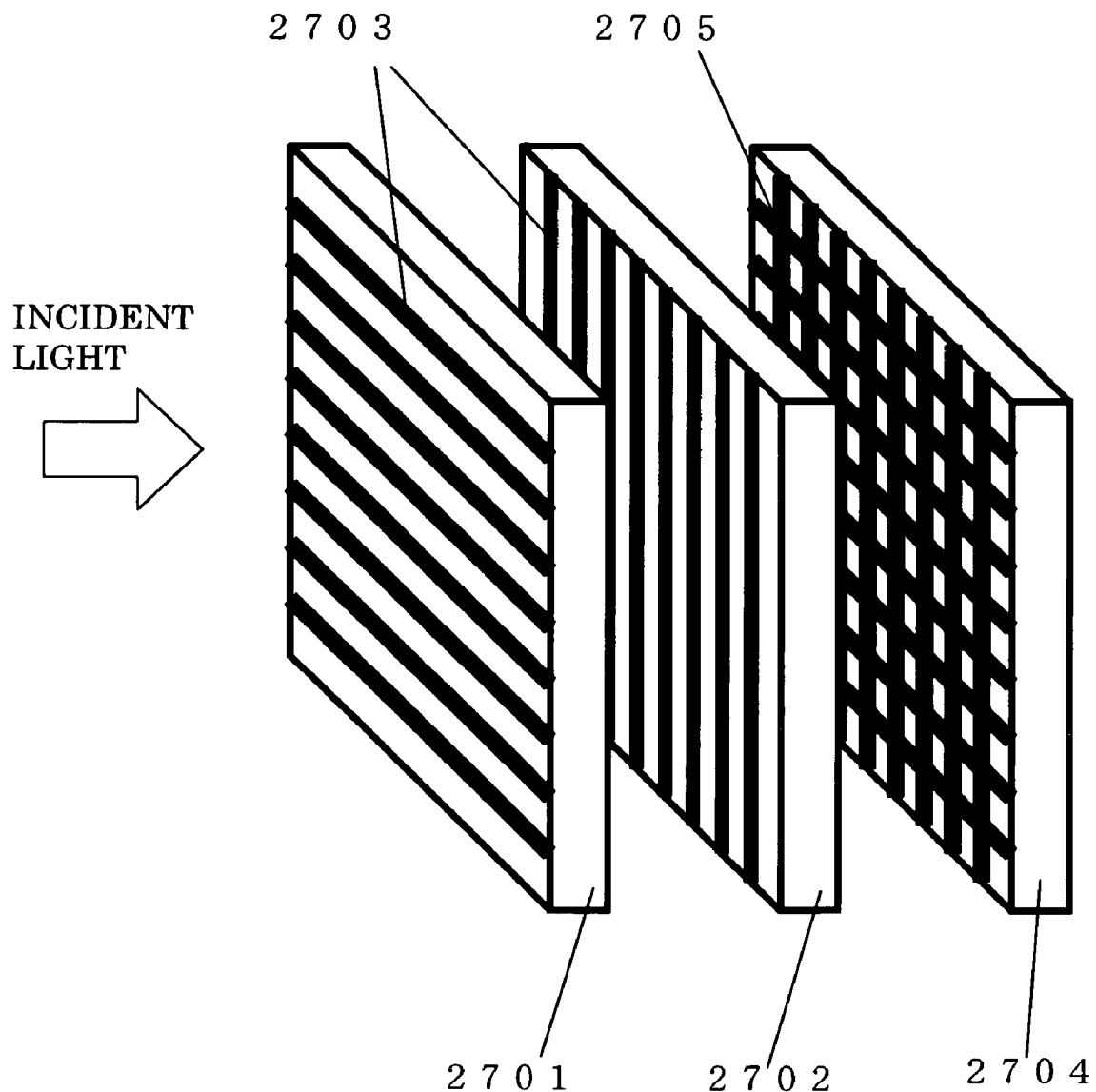
FIG. 27 is a constitutional example of a polarization analysis device that avoids the effects of scattered/diffracted light by a shielding region.

Because the scattering and diffraction of light is unavoidable on account of the structure in the boundary neighborhood of the respective regions of the wavelength plate array and the polarizer array that are used by the polarization analysis device of the present invention, the light image is disturbed. FIG. 27 shows an example of claim 10 that serves to remove light in the boundary neighborhood of the array and to obtain a more distinct intensity distribution pattern. Light-shielding regions 2703 indicated by black lines are disposed in the boundary parts of the respective regions of a wavelength plate array 2701 and a polarizer array 2702 and light falling incident on these parts cannot reach the light-receiving elements. Alternatively, scattered light and diffracted light can also be removed by providing light-shielding regions 2705 in regions in which light enters from the boundary parts of the wavelength plate array and polarizer array of a light-receiving element array 2704.

EXAMPLE 9

Figure 28:
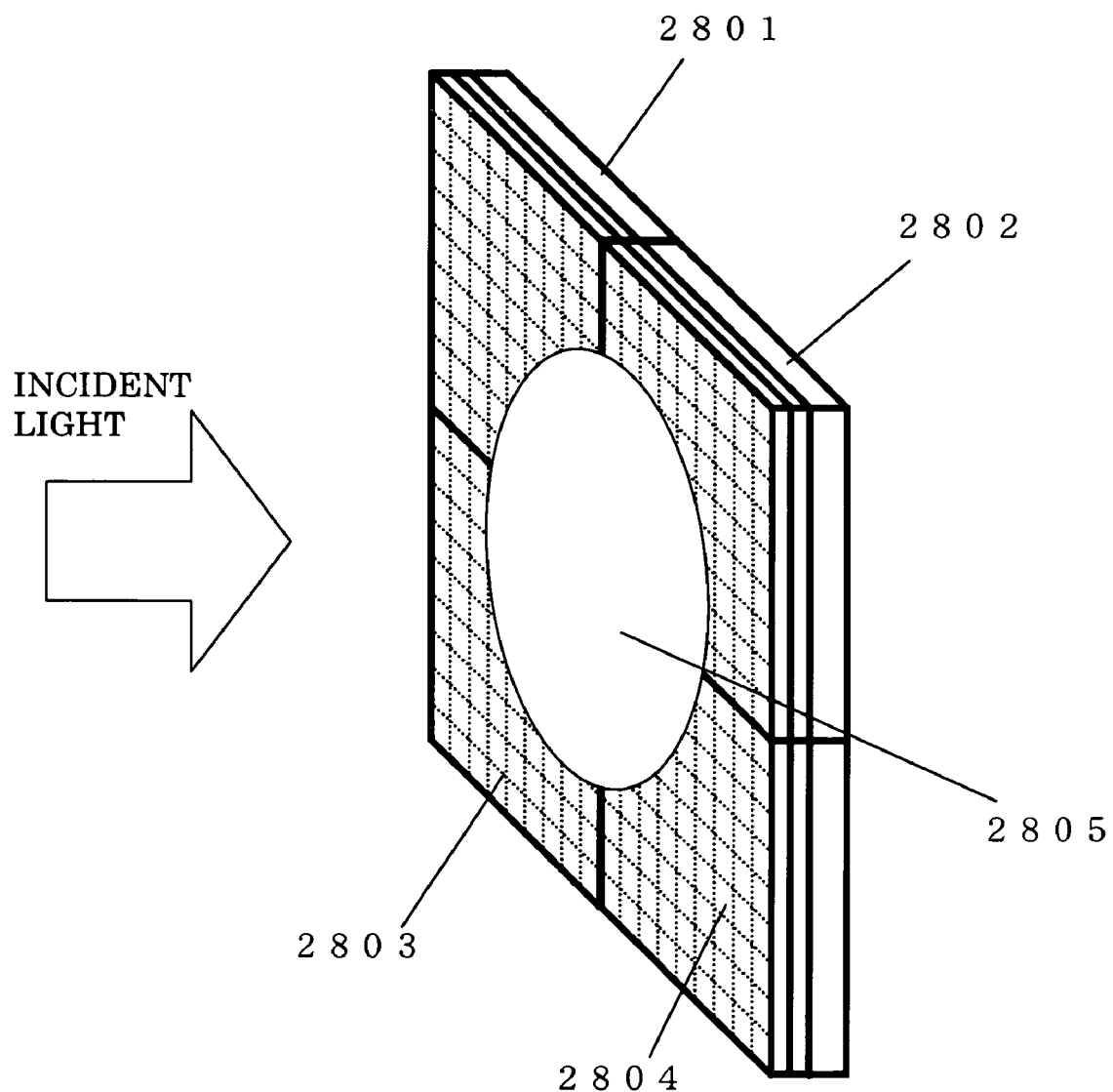
FIG. 28 is a constitutional example of a polarization analysis device for avoiding the effects of the positional fluctuations of incident light.

As an example of claim 11, FIG. 28 shows an example of a method that arranges the polarization analysis device of the present invention in four planes to avoid measurement errors caused by fluctuation of the position of the incident beam. Because the present invention allows a sufficiently small polarization analysis device to be implemented by using a photonic crystal, it is also easy to arrange a plurality of polarization analysis devices in a small region and to bring a plurality of polarization analysis devices together through integration thereof. By arranging polarization analysis devices 2801 to 2804 so that same are lined up in a plane, light is irradiated onto any of four regions even when an incident light beam fluctuates. By suitably designing the beam diameter of the incident light beam, the same or better information as that of the intensity distribution obtained from one polarization analysis device of the present invention can be obtained irrespective of the irradiation position of the beam. For example, as FIG. 28 shows, when light enters a center region 2805 of the four polarization analysis devices, ¼ of the intensity distribution information is obtained from each of the respective regions. Polarization analysis can be performed by multiplexing this information. If the number of polarization analysis devices disposed in the plane is increased further, it is possible to deal with even larger beam fluctuations.

EXAMPLE 10

Figure 29:
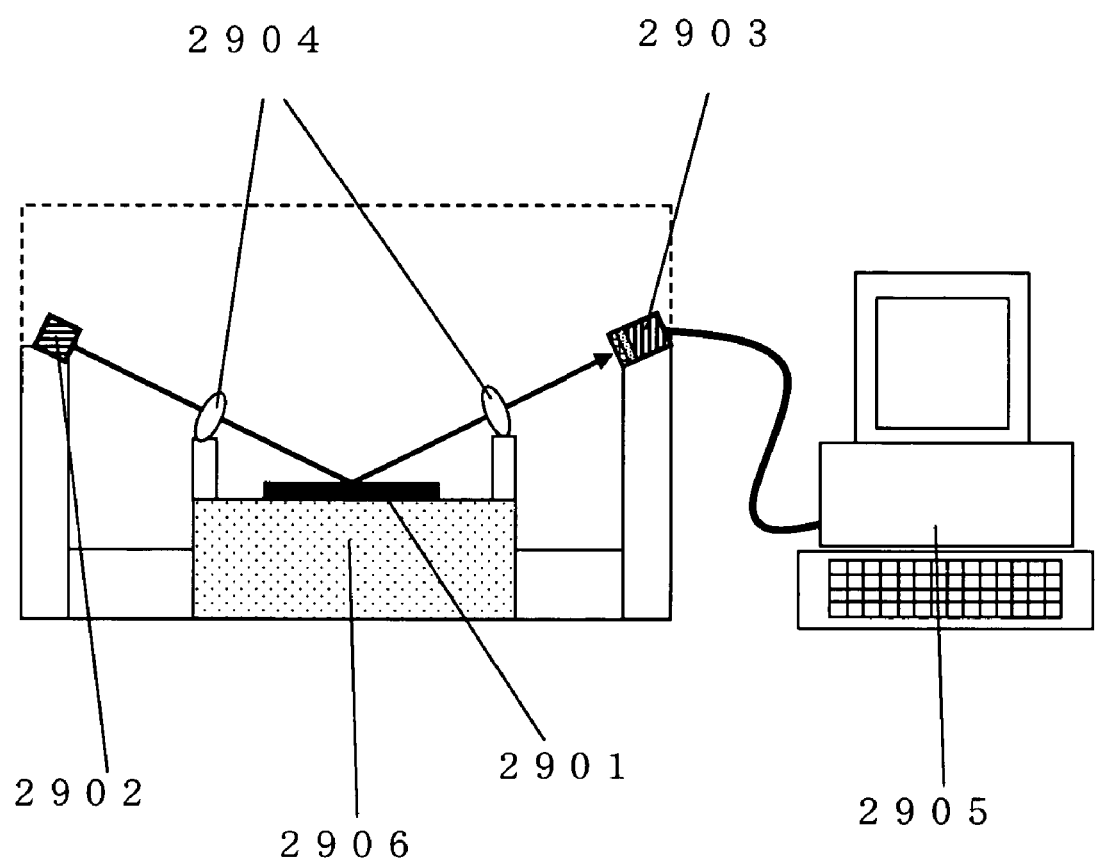
FIG. 29 is a conceptual view of the constitution of an ellipsometer that utilizes the present invention.

As an example of claim 13, FIG. 29 shows an ellipsometer that is implemented by combining the polarization analysis device of the present invention and a laser light source. FIG. 29 is a real example of an ellipsometer that employs the present invention. Other constitutions may also be considered as a constitution for implementing the ellipsometer by using the present invention. In FIG. 29, a sample stand 2906 is disposed at the center of a device in which a light-receiving element 2903 rendered by combining the wavelength plate array and the polarizer array, and a laser light source 2902 are disposed. The polarization state of the exit light from the laser is already known. A thin film sample 2901 that is to be measured is placed on the sample stand 2906 and, at the same time as focusing a laser beam on the sample, a pair of lenses 2904 are adjusted so that the reflected light is a parallel beam that reaches a polarization analysis device 2903. The reflected light from the sample is detected by the polarization analysis device 2903 and the polarization state of the reflected light is calculated from the intensity distribution measured by a CPU 2905. An ellipsometer generally represents the polarization state of light by the amplitude intensity ratio ($\psi$) and the phase difference ($\Delta$) of a wave P and a wave S. Normally, 45° linearly polarized light ($\psi=1$, $\Delta=0$) is used as the incident light and $\psi'$ and $\Delta'$ of the reflected light are measured. The Fresnel reflectance of waves P and S of the sample (Rp, Rs), that is, the film thickness and refractive index of the thin film can be found from the measurement results.

EXAMPLE 11

Figure 30:
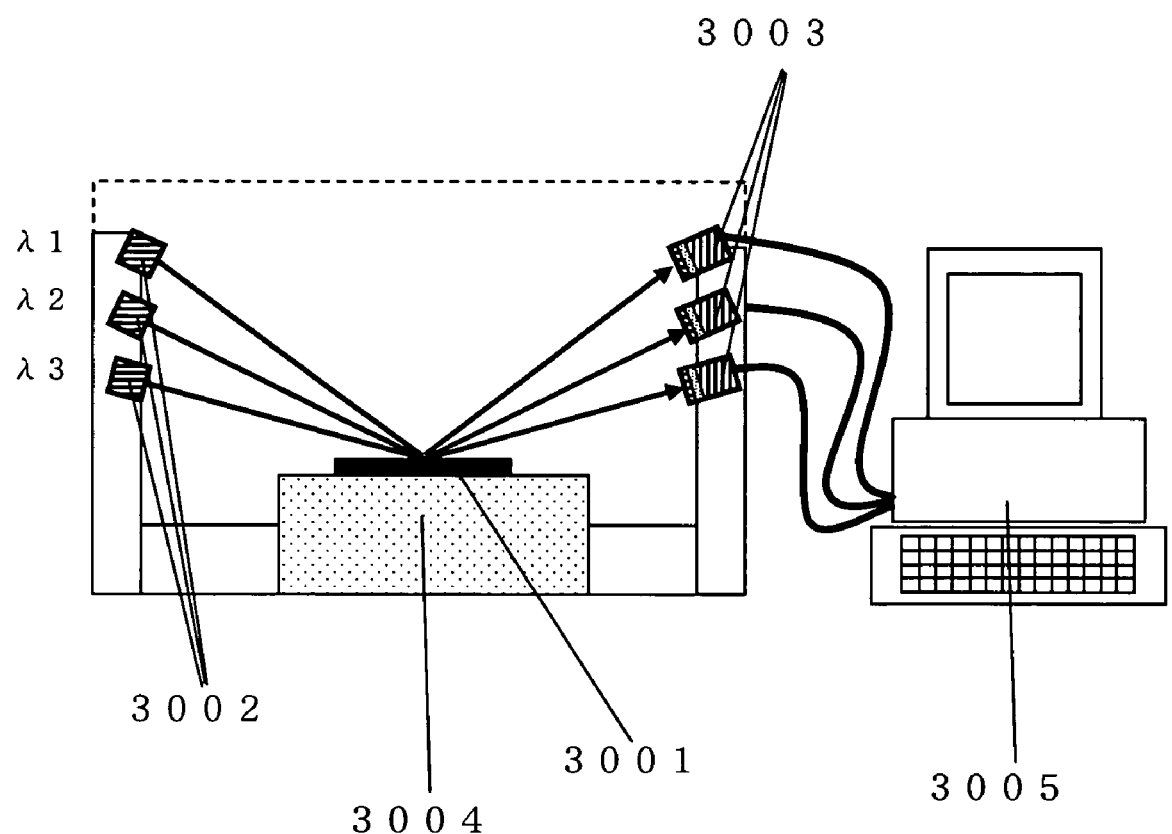
FIG. 30 is a conceptual view of the constitution of a spectro-ellipsometer that utilizes the present invention.

As another example of claim 13, FIG. 30 shows a simple spectro-ellipsometer that can be implemented by using the polarization analysis device of the present invention. As the case of the ellipsometer of the example 10, this case involves setting a sample substrate 3001 onto a sample stand 3004, irradiating light from a laser light source group 3002 of respectively different wavelengths, and detecting the reflected light of the respective wavelengths by using a light-receiving head group 3003 that corresponds with the respective wavelengths. The fact is that the polarization states detected by the respective light-receiving heads are analyzed by a CPU 3005 but the film thickness and film quality of the sample can be evaluated accurately by using a plurality of wavelengths.

When a spectro-ellipsometer of this kind was implemented by the prior art, a plurality of sets of driving parts and a high-precision rotating mechanism were required, which not only made the device large, but also produced the drawback that the measurement time was also long. On the other hand, by using a photonic crystal, the present invention is capable of implementing a small polarization analysis device. Therefore, not only is it possible to house a plurality of optical systems within one device easily, but a highly reliable device can be implemented because there are no driving parts. In addition, because a polarization state can be discriminated instantly from the results obtained by the light-receiving element array, the measurement time is also very short.

EXAMPLE 12

Figure 31:
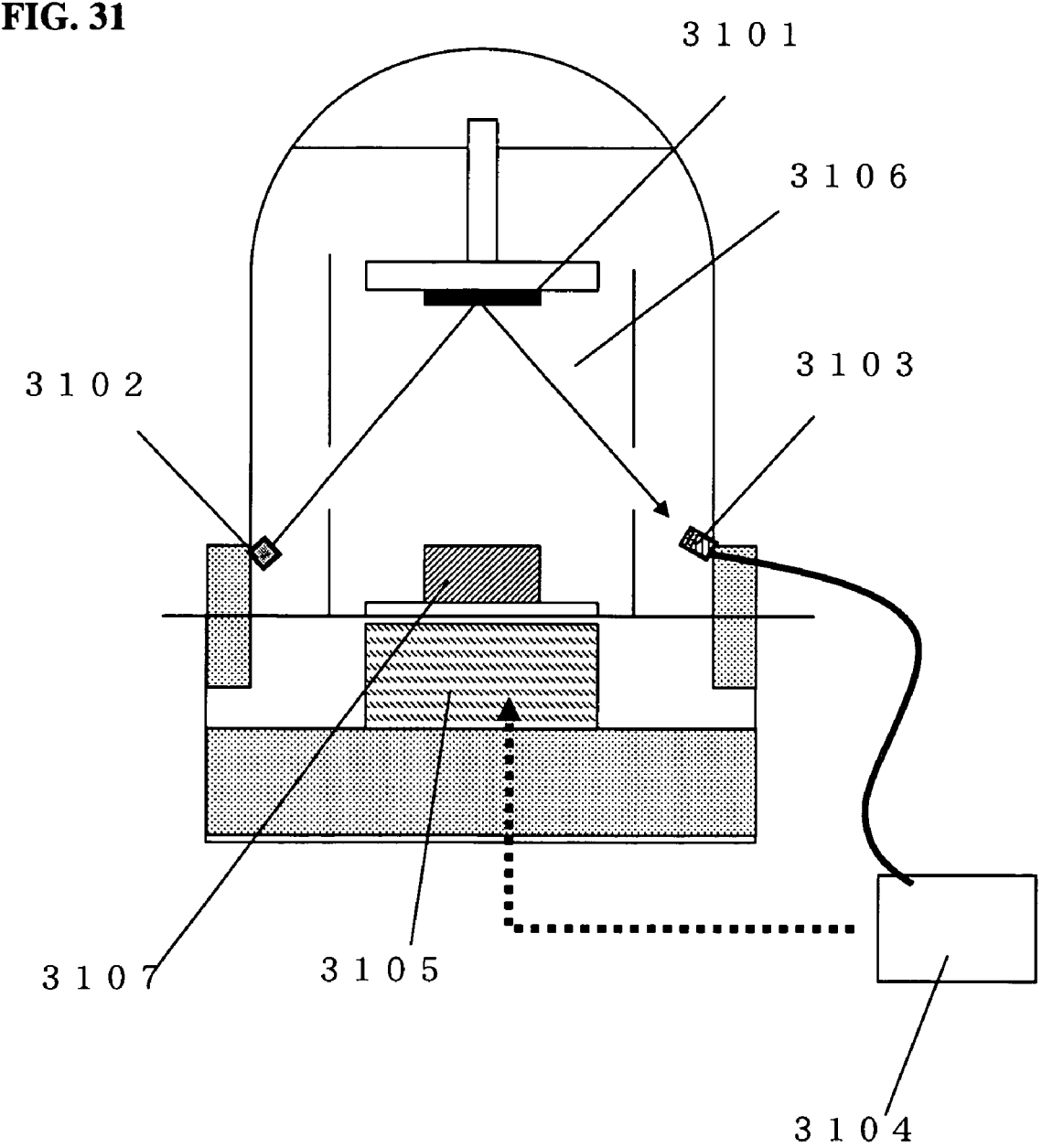
FIG. 31 is a conceptual view of an online film thickness/film quality monitor in the thin-film process.

As examples of claims 14 and 15, FIG. 31 shows an example of a film thickness/film quality monitor in a thin-film formation process such as vapor deposition or sputtering. A process device such as one in which a substrate 3101 is placed in a vacuum chamber 3106 and a material source 3107 is deposited on the substrate by controlling a control circuit 3105 may be considered. A laser light source 3102 and a light-receiving head 3103 of the polarized wave analysis device of the present invention are placed in the chamber of the film deposition device as shown in FIG. 31, laser light is irradiated onto the substrate and reflected light from the substrate is detected by the light-receiving section head. Although a small laser light source is installed in the chamber in FIG. 31, a light source can also be installed outside the chamber and light can be guided inside the chamber by using polarized-wave retention-type optical fiber or the like. Signals from the light-receiving head are analyzed by a CPU 3104 and the film thickness and refractive index of the thin film in the film deposition can be monitored in real time from the intensity distribution of light. In addition, information on the monitored film thickness and film quality and so forth can be fed back to the device to control the film deposition conditions, whereby strict film-deposition management can also be performed.

The real-time film thickness/film quality monitor in such a thin-film formation process is extremely useful in high-precision film thickness and film quality management and is not a conventional technology. A conventional ellipsometer is a large-scale device that is substantially incapable of monitoring film thickness/film quality in real time in a process device. Further, film thickness monitors such as a water-crystal oscillator, for example, have also existed but monitoring of film quality that includes the refractive index has not been possible. Because the present invention makes it possible to implement an ultra-small and highly reliable ellipsometer, the introduction into the device of a vacuum-process film thickness/film quality monitor is also straightforward. Further, as also mentioned earlier, information on the absolute value of the optical intensity is not required by the present invention and the film thickness/film quality can be judged by only the relative intensity distribution. Therefore, monitoring is possible without affecting the optical intensity fluctuations due to adhesion or the like to a window of film-deposition material.

In a normal vacuum process, film deposition is typically performed while causing a substrate holder to rotate or revolve (or both) in order to form a uniform film. Monitoring the film thickness and film quality and so forth of the substrate that is always moving has conventionally been considered to be extremely difficult. So too in this case, because sufficiently high-speed film thickness/film quality measurement can be implemented by using the present invention, film thickness/film quality monitoring is possible in real time by employing a method that matches the rotation cycle of the substrate holder with the measurement sampling cycle, or the like, for example. If a sampling cycle is devised, even when film deposition is performed on a plurality of substrates at once, monitoring of the film thickness/film quality of each substrate will then also be possible. Further, even in a case where there is sudden movement of the substrate holder and fluctuations in the position of incidence of the light, measurement errors can be avoided by widening the beam diameter of the incident light, adopting the intensity distribution correction method indicated by claim 9 and the example 6 and example 7 and the countermeasures to beam position fluctuations indicated by claim 11 and the example 9.

EXAMPLE 13

Figure 32:
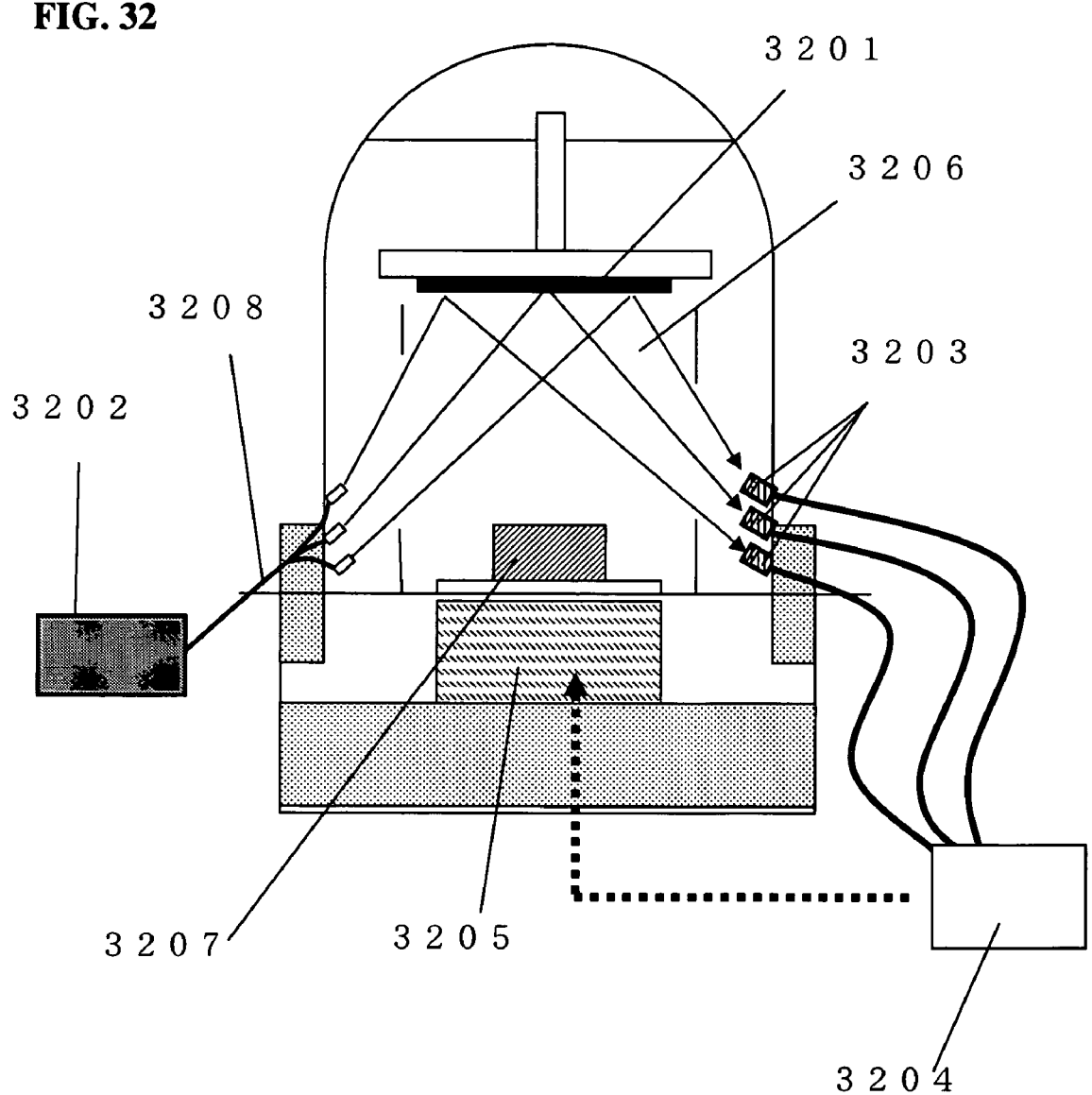
FIG. 32 is a conceptual view of an online film thickness/film quality and distribution monitor in the thin-film process.

As an example of claim 16, FIG. 32 shows a constitution rendered by introducing a plurality of ellipsometers to a process device. In this example, beam light is guided from the laser light source 3202 outside the process device into a vacuum chamber 3206 by using an optical fiber 3208. The optical fiber splits into a plurality of optical fibers and light emitted from each of the fiber ends is reflected in a different position on a substrate 3201 and detected by a polarization analysis device group 3203 of the present invention. As a result of such a constitution, the distribution of the film thickness/film quality caused by the difference in the location on the substrate can also be monitored in real time in addition to monitoring the film thickness/film quality during film deposition. If distribution information calculated by a CPU 3204 can be fed back to a film deposition control device 3205 in the apparatus and the distribution of the film composition and film deposition rate can be controlled, a more uniform film can be formed.

Figure 33:
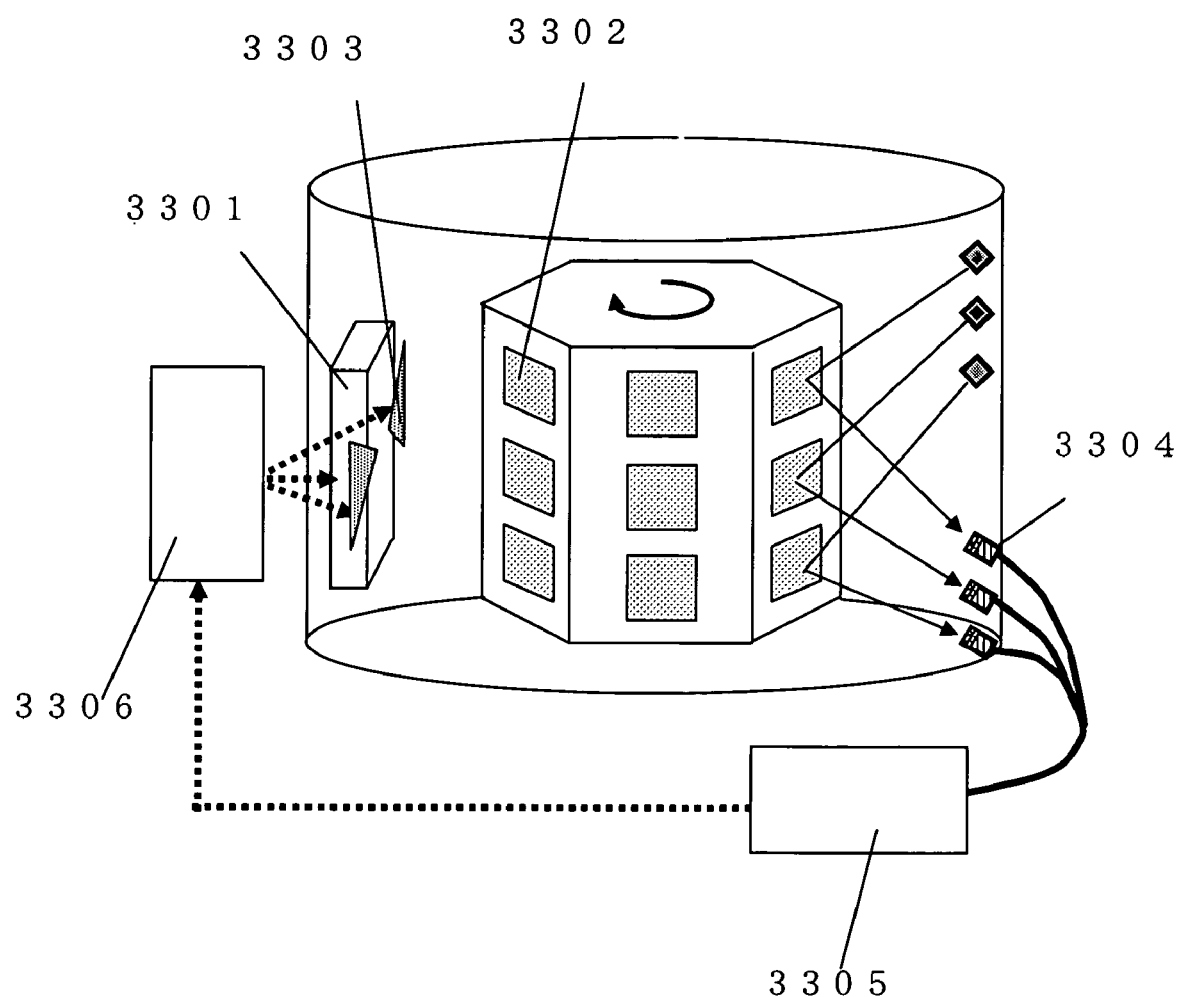
FIG. 33 is an example (1) of a method of controlling film thickness/film quality and distribution in a sputtering device.

A method of establishing film uniformity in a process that can be implemented by the present invention will now be described in simple terms. FIG. 33 is an example in which a plurality of film-thickness control devices are attached to a side sputtering device. A target 3301 is disposed upright and substrates are attached to the circumference of a rotation-type drum 3302. Usually, the film thickness and film quality are uniform in the rotation direction of the substrate but nonuniform in a vertical direction. The film thickness decreases toward the periphery. Therefore, a method of controlling the plasma density by disposing a correction plate 3303 in the periphery of the target in order to widen the uniform area in the vertical direction has been proposed. Conventionally, in order to increase the uniformity of the film, adoption of a complex method that involves offline measurement of the film thickness distribution following film deposition and repeating the film formation by adjusting the shape and attachment position of the light-shielding plate has not been possible. It has therefore been extremely difficult to make the distribution uniform to 1 to 2% or less. On the other hand, when the ellipsometer 3304 of the present invention is employed, adjustment is possible such that the film thickness distribution is fixed online by controlling the degree of opening of the light-shielding plate and the power applied to the target by feeding back distribution information on the film thickness/film quality, which is obtained by means of the calculation by the CPU 3305 from real-time measurement results, to a film-deposition control device 3306.

Figure 34:
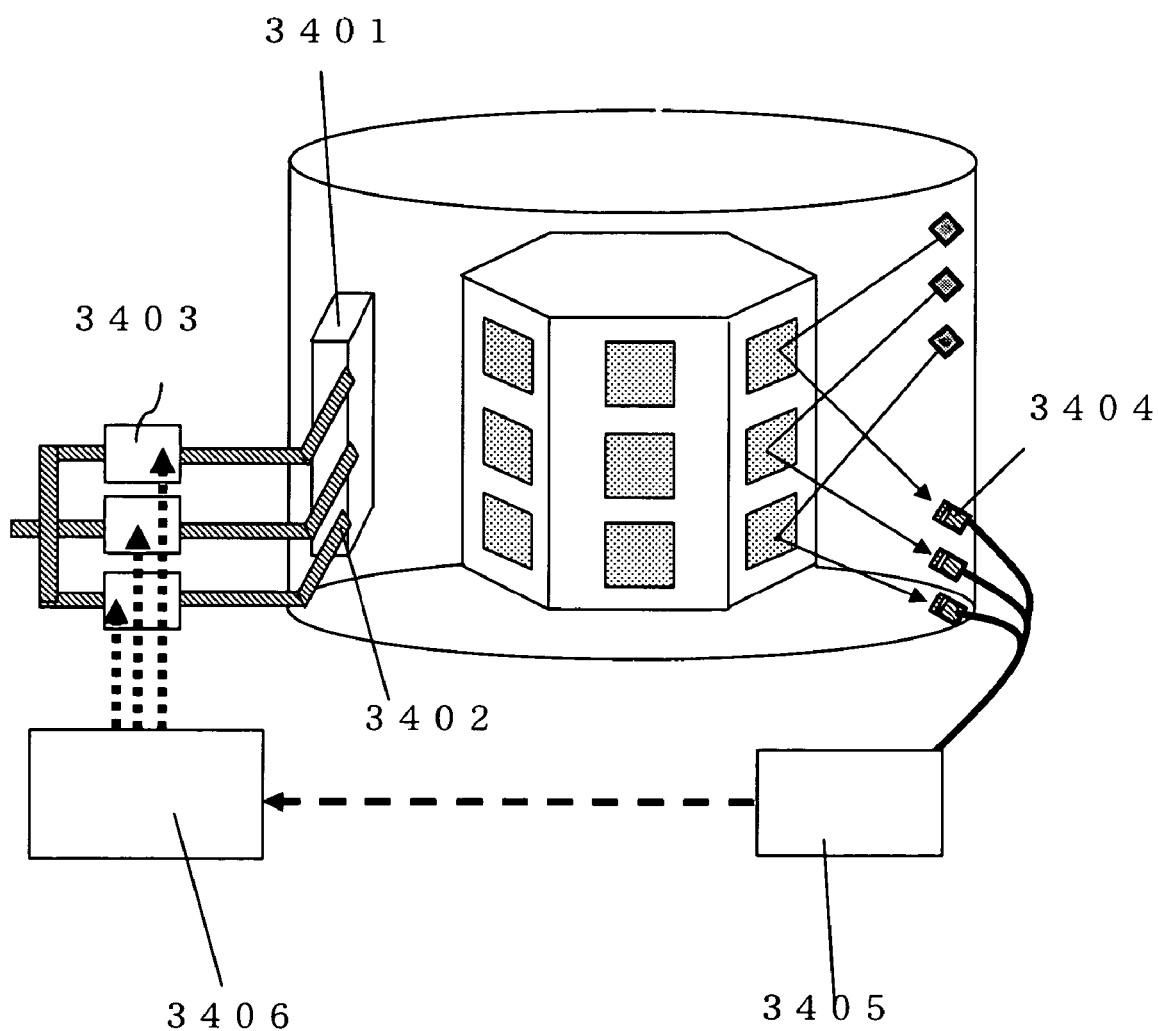
FIG. 34 is an example (2) of a method of controlling film thickness/film quality and distribution in a sputtering device.

FIG. 34 shows another example in which a film in a sputtering device is made uniform. A sputtering device in which a plurality of gas entry inlets 3402 are disposed in the periphery of a target 3401 and a mass-flow controller 3403 for controlling the gas flow amount in each case is installed may be considered. In such a sputtering device, the plasma density can be partially controlled by controlling the flow amount of gas supplied to the periphery of the target. Because there is a correlation between the film quality and film deposition rate that is typically deposited and the plasma density, the film thickness/film quality can be controlled in each position by controlling the plasma density in each position. If the ellipsometer 3404 of the present invention is used, information on the film pressure/film quality obtained by the CPU3405 is fed back to the control circuit 3406 in real time, and the plasma density in the device can be controlled online, uniform film deposition of uniform quality is possible.

Figure 35:
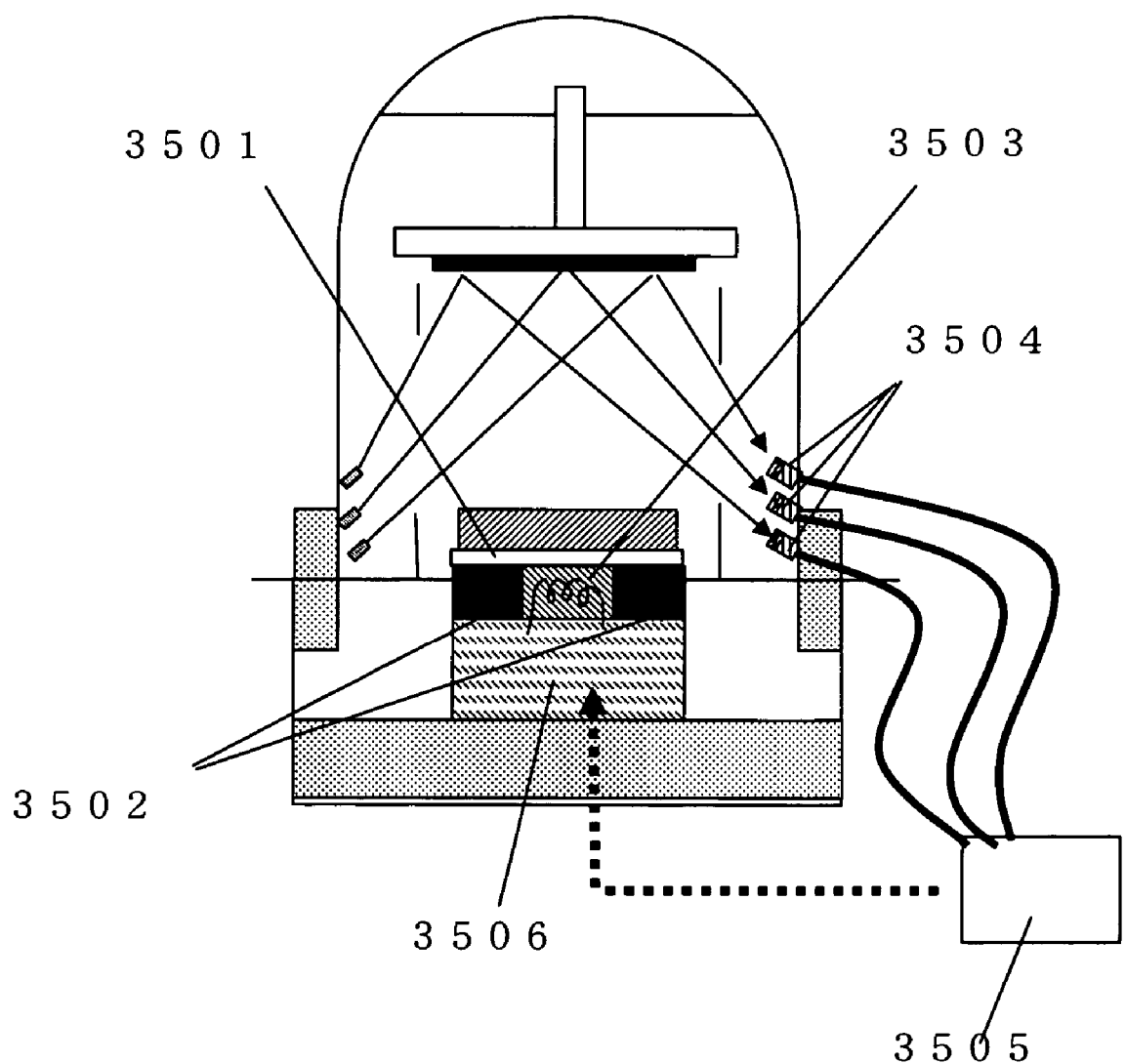
FIG. 35 is an example (3) of a method of controlling film thickness/film quality and distribution in a sputtering device.

FIG. 35 shows a third example of a film-deposition control method that employs a sputtering device. Both a permanent magnet 3502 and an electromagnet 3503 are arranged inside a cathode 3501 of a magnetron sputtering device. By controlling the current flowing through the electromagnet in this device, the overall plasma density can be controlled. Because real-time control of the plasma density is possible by feeding back distribution information monitored by using the ellipsometer 3504 and CPU3505 of the present invention to a control circuit 3506 to control the electromagnet, online control of the film thickness/film quality is possible.

Figure 36:
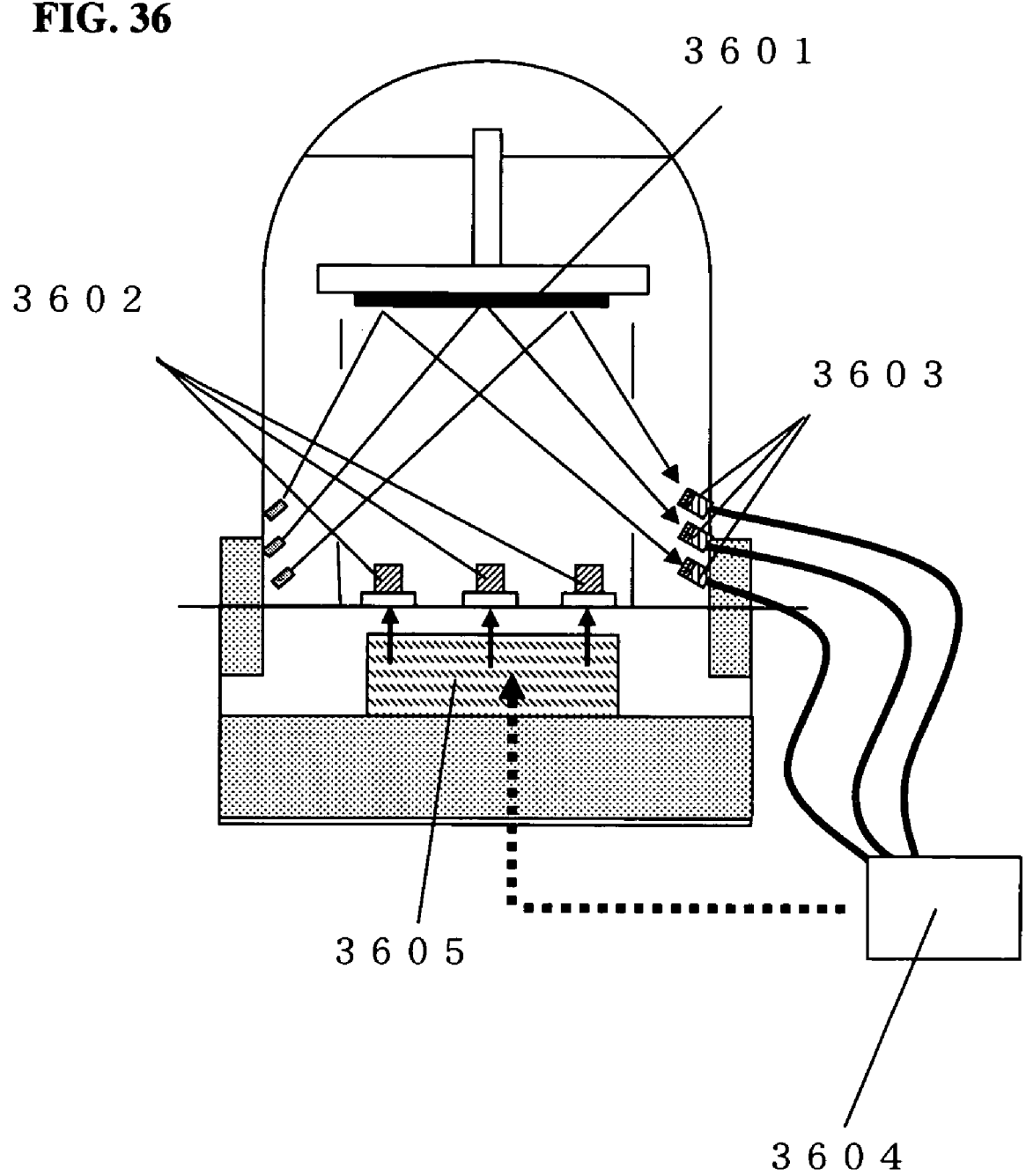
FIG. 36 is an example of a method of controlling film thickness/film quality and distribution in a vacuum deposition device.

Finally, FIG. 36 shows an example of a procedure for making a film uniform in a vacuum deposition device. A multiple source vapor deposition device in which a plurality of vapor deposition sources 3602 are arranged in a chamber may be considered. With such a device, the film thickness and film quality distribution can be controlled by controlling the distribution of power applied to the respective vapor deposition sources. An ellipsometer 3603 of the present invention is used to monitor the film thickness/film quality in each position of the substrate 3601 in real time and to feed back distribution information calculated by the CPU3604 to the film deposition control device 3605. If the power amount applied to the respective vapor deposition sources can be controlled on the basis of the distribution information obtained through measurement, the creation of a uniform film of uniform quality is possible.

EXAMPLE 14

A polarization analysis device of a new method that employs the wavelength plate array and polarizer array used by the present invention is driverless and is therefore highly reliable and is advantageous in that same permits a rapid shortening of the measurement time in comparison with conventional devices. Further, the use of a photonic crystal not only makes it possible to implement a small device but also permits highly precise control of the principal axis direction of each array. However, it is difficult to strictly match the phase difference (retardation) of the wavelength plate array with a ¼ wavelength ($\pi/2$ radians), which is the ideal value even when advanced process control is performed. When the structure and creation method of the photonic crystal are considered, there is no distribution in the process and it is expected that the phase difference of each of the wavelength plate regions of the wavelength plate array will all have a fixed value even in the event of a shift from the design values.

Figure 37:
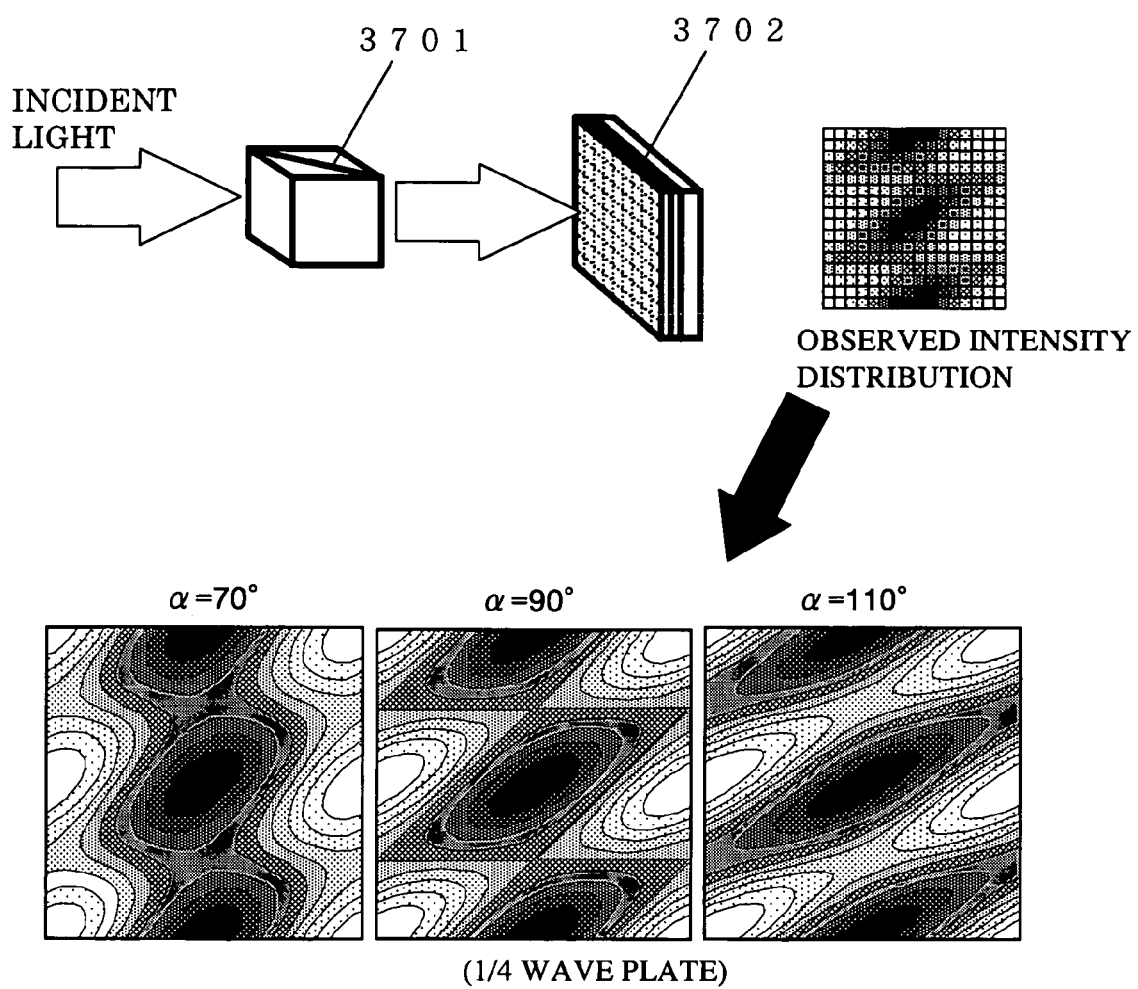
FIG. 37 shows a first example of a method for correcting phase difference shift in the wavelength plate array.

FIG. 37 shows a first example of claim 21, which is a method for correcting the phase difference shift of a wavelength plate array of this kind. This method finds the phase difference of the wavelength plate from intensity distribution information that is observed when light of a certain specified polarized wave state enters the polarization analysis device and corrects shifts in the phase difference. By way of example, a case where linearly polarized light enters the polarization analysis device 3702 by using a polarizer 3701 of a high quench ratio such as a Glan-Thomson prism may be considered (here, the tilt angle of the polarized wave is optional). Here, the optical intensity distribution observed in cases where the phase difference of the wavelength plate array in the polarization analysis device is 70°, 90°, and 110° respectively is shown. As mentioned many times earlier, the intensity distribution pattern in cases where linearly polarized light enters the device is a 'ship's bottom-type' shape. However, as can also be seen from FIG. 37, the ship's bottom elliptical shape (ellipticity) changes according to the phase difference of the wavelength plate array. Therefore, by analyzing the shape of the intensity distribution pattern obtained when linearly polarized light enters the polarization analysis device, a shift in the phase difference of the wavelength plate array can be correctly evaluated. Here, the earlier-mentioned contour analysis method and Fourier analysis method can be used as the procedure for analyzing the pattern that is observed when linearly polarized light enters the polarization analysis device.

EXAMPLE 15

Figure 38:
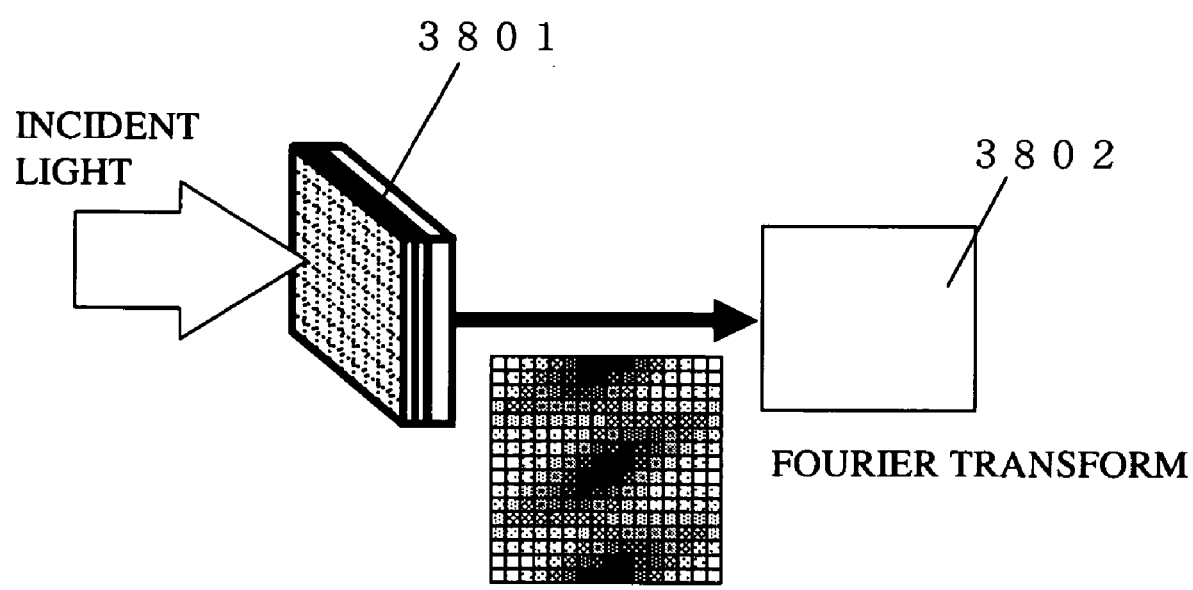
FIG. 38 shows a second example of a method for correcting phase difference shift in the wavelength plate array.

FIG. 38 shows a second example of claim 21 as a method for correcting the phase difference shift of the wavelength plate array. Light of an optional polarization state enters a polarization analysis device 3801 and the observed optical intensity distribution undergoes a Fourier transform by means of a CPU 3802. Thereupon, the respective frequency components obtained by means of the Fourier Transform are represented by Equation 8 as mentioned earlier. When the respective frequency components are X, Y, and Z, the phase difference ($\alpha$) of the respective wavelength regions of the wavelength plate array can be found by

[Equation 11]  (Equation 11)

That is, when a Fourier transform is adopted for the analysis of the intensity distribution shape, not only can the ellipticity ($\epsilon$) of the incident light and tilt ($\gamma$) of the polarized wave be found as mentioned earlier from the value of the respective frequency components determined by the Fourier transform but also the value of the phase difference ($\alpha$) of the wavelength plate can also be found at the same time.

As mentioned earlier, with the polarization analysis method of the present invention, even when the phase difference of the wavelength plate array is fixed (uniform) over all the regions of the array, the size of the phase difference is not a problem. For example, no matter what value the value of the phase difference takes (except when $\alpha=0°$), a shift in the phase difference can be accurately evaluated by analyzing the intensity distribution pattern thus observed, whereby the correct value for the incident polarized light can be obtained. This is a very beneficial point in comparison with a conventional ellipsometer that uses a single wavelength plate and polarizer. For example, in quenching methods adopted by conventional ellipsometers, when the phase difference of the wavelength plate used shifts even a little from a ¼ wavelength, the quenching point shifts from the original position when the polarizer or wavelength plate is made to rotate. Hence, accurate polarized wave analysis is impossible.

EXAMPLE 16

The wavelength plate array and polarizer array of the polarization analysis device used by the present invention are produced by arranging a plurality of different regions. Hence, the boundary part of the respective regions is discontinuous, and light scatter and diffraction are produced. The scattered light and diffracted light appear as noise in the signal processing, which causes deterioration of the accuracy of the polarization analysis. Hence, in order to implement a highly accurate device, there is also a procedure that arranges a wavelength plate array and polarizer array or light-receiving element array that are used by the polarization analysis device in a light-shielding region so that scattered light or diffracted light is not received, as illustrated by claim 10. However, FIG. 16 shows an example of a signal processing method that is illustrated by claim 22 as a procedure for removing the effects of scattered light and diffracted light without using such a light-shielding structure.

Light that has passed through a wavelength plate array 1601 and polarizer array 1602 enters the light-receiving element array 1603. When it is assumed that a general CCD is used as the light-receiving element array, the size of a single light-receiving element is on the order of a few µm and is relatively small in comparison with the size of the respective regions of the wavelength plate array and polarizer array. Therefore, a plurality of light-receiving elements exist in the light-receiving element regions that receive light that has passed through each region created by the intersections between the wavelength plate array and polarizer array. Among the electrical signals that are output by the light-receiving elements, if signals that are output by a region 1604 that receives light including scattered light and diffracted light from the boundary part of the wavelength plate array and polarizer array are not used and the optical intensity of the respective regions is found by totaling or averaging only the signals outputted by region 1605 that receives light unaffected by scattered light or diffracted light, highly accurate polarization analysis is then implemented. In FIG. 16, although region 1604 whose signals are not used is divided into one column's worth of light-receiving elements above and below the respective regions, the adoption and size of regions are optional and change depending on the structure of the polarization analysis device. A signal processing method of this kind can be calculated at high speed and very simply by means of a CPU and is therefore a very effective method of improving the polarization measurement accuracy.

INDUSTRIAL APPLICABILITY

The polarization analysis device implemented by the present invention and the ellipsometer that uses this polarization analysis device are small and driverless and capable of analyzing the polarized state of incident light highly accurately and at high speed. By using a photonic crystal, the constituent parts can be reduced and, not only can positional adjustment also be performed easily but a shift in the phase difference of the wavelength plate array can also be corrected by devising pattern analysis. A stable device of very high producibility can therefore be implemented.

Therefore, the film thickness and film quality and so forth of a sample that is conventionally measured offline by using a costly and large-scale device can also be measured online by installing a plurality of ellipsometers in one thin-film fabrication device. Thus, the polarization analysis device or ellipsometer of the present invention is suited to quality control or control of thin-film fabrication and is capable of replacing conventional methods.

The invention claimed is:

1. A polarization analysis device, comprising:
a wavelength plate array having a plurality of regions in which phase differences supplied to transmitted light are uniform and optical axis directions are different; and
a polarizer array having a plurality of regions in which the directions of transmitted polarized waves are different,
wherein the wavelength plate array and the polarizer array are arranged to overlap one another, and a light-receiving element array is disposed so as to be capable of individually receiving light passed through a specified region of the wavelength plate and a region of the polarizer that overlaps the specified region.

2. A polarization analysis device, comprising:
a wavelength plate array having at least two or more stripe-like regions in which phase differences supplied to transmitted light are uniform and individual optical axis directions are different; and
a polarizer array having at least two or more stripe-like regions in which the directions of transmitted polarized waves are different,
wherein the wavelength plate array and the polarizer array are disposed so that the respective stripes of the wavelength plate array and of the polarizer array intersect one another, and a light-receiving element array is disposed so as to be capable of individually receiving light passed through the respective regions of intersection.

3. The polarization analysis device according to claim 1 or 2, wherein the wavelength plate array and the polarizer array consist of a dielectric multilayered film in which the shape of the layers is cyclical in the stacking direction and in which the shape of each layer has a cyclical corrugated shape that is repeated in one direction in a plane determined for each region.

4. A polarization analysis device, comprising:
a wavelength plate array having a plurality of regions in which optical axis directions are uniform and phase differences of transmitted light are different; and
a polarizer array having a plurality of regions in which the directions of transmitted polarized waves are different,
wherein the wavelength plate array and the polarizer array are disposed to overlap one another, and a light-receiving element array is disposed so as to be capable of individually receiving light passed through a specified region of the wavelength plate and a region of the polarizer that overlaps the specified region.

5. A polarization analysis device, comprising:
a wavelength plate array having at least two or more stripe-like regions in which optical axis directions are uniform and phase differences of transmitted light are different; and
a polarizer array having at least two or more stripe-like regions in which the directions of transmitted polarized waves are different,
wherein the wavelength plate array and the polarizer array are disposed so that the respective stripes of the wavelength plate array and of the polarizer array intersect one another, and a light-receiving element array is disposed so as to be capable of individually receiving light passed through the respective regions of intersection.

6. A polarization analysis device according to claim 4 or 5, wherein the wavelength plate array comprises a dielectric multilayered film the shape of which is cyclical in the stacking direction and which has a common corrugated shape that is cyclical in one direction with a repetitive cycle determined for each region; and
the polarizer array comprises a dielectric multilayered film the shape of which is cyclical in the stacking direction and in which the shape of each layer has a cyclical corrugated shape that is repeated in one direction within a plane determined for each region.

7. The polarization analysis device according to any of claims 1, 2, 4 or 5, wherein unnecessary multiple reflection light is reduced by providing a light-absorbing layer between the wavelength plate array and the polarizer array or between the polarizer array and the light-receiving element array or both, or by forming a nontransparent region or transparent region at the boundary of the respective array regions for at least one of the wavelength plate array, the polarizer array and the light-receiving element array.

8. The polarization analysis device according to claim 7, wherein, by providing an isotropic transparent region for incident polarized light in a peripheral region of the wavelength plate array and the polarizer array or by providing an isotropic transparent region for incident polarized light in a portion of the boundary part of the respective regions of the wavelength plate array and the polarizer array, an intensity distribution of incident light and a transmission loss distribution of the wavelength plate array and the polarizer array are measured at the same time as an intensity distribution of light passed through respective wavelength plate regions and respective polarizer regions, and the measurement results are corrected.

9. The polarization analysis device according to claim 8, wherein the effects of diffraction and scattering of light in the boundary part are suppressed by providing a light-shielding part in the boundary part of the respective regions of the wavelength plate array and the polarizer array or by light-shielding the region of the light-receiving element array corresponding with the boundary part of the respective regions of the wavelength plate array and the polarizer array.

10. A polarization analysis device, wherein measurement errors caused by positional fluctuations of the incident light beam are avoided by arranging a plurality of the polarization analysis device according to claim 9 within a plane.

11. A light measurement device or light measurement system that uses the polarization analysis device according to claim 10.

12. An ellipsometer that causes polarized light to enter a measurement sample at a predetermined angle, introduces reflected light reflected by the measurement sample to the polarization analysis device according to claim 10 and obtains the amplitude reflectance ratio of the P polarization component and the S polarization component from an optical intensity distribution obtained by a light-receiving element array.

13. A film thickness and film quality control device, wherein film thickness and film quality information obtained by the ellipsometer according to claim 12 is fed back to a device for controlling the film deposition speed or film deposition time.

14. A film thickness and film quality control device, comprising:
at least two or more of the ellipsometers according to claim 12,
wherein information obtained by measuring the film thickness and film quality in different positions of the substrate at each point is fed back to a film thickness and film quality distribution correction control device.

15. An ellipsometer that causes polarized light to enter a substrate surface undergoing thin-film deposition at a predetermined angle in a vacuum thin-film formation device, introduces reflected light reflected by the substrate surface to the polarization analysis device according to claim 10, and obtains the amplitude reflectance ratio of the P polarization component and S polarization component from an optical intensity distribution obtained by the light-receiving element array.

16. A film thickness and film quality control device, wherein film thickness and film quality information obtained by the ellipsometer according to claim 15 is fed back to a device for controlling the film deposition speed or film deposition time.

17. A film thickness and film quality control device, comprising:
at least two or more of the ellipsometers according to claim 15,
wherein information obtained by measuring the film thickness and film quality in different positions of the substrate at each point is fed back to a film thickness and film quality distribution correction control device.

18. A polarization analysis method, wherein, in a polarization analysis device in which a wavelength plate array having a plurality of regions in which the phase differences are fixed and the optical axis directions are different and a polarizer array having a plurality of regions in which the directions of transmitted polarized waves are different are arranged to overlap one another so that the wavelength plate array is at the front and the polarizer array is at the rear and a light-receiving element array is disposed in two dimensions so as to be capable of individually receiving light passed through a certain region of the wavelength plate and a region of the polarizer that overlaps the certain region of the wavelength plate, the polarization state of incident light is obtained by using the characteristics that a two-dimensional intensity distribution pattern observed by means of the light-receiving element array is exhibited by only a DC component and at most three frequency components.

19. The polarization analysis method according to claim 18, wherein, by fitting or inserting sample values in use of the characteristics of a pattern shape in the neighborhood of a maximum point or a minimum point of an intensity distribution pattern observed by the light-receiving element array, the directions of the wavelength plate and polarizer that supply the ellipsometry quenching point or the flow amount minimum are calculated and the polarization state of incident light is obtained.

20. The polarization analysis method according to claim 18, wherein the polarization state of incident light is obtained by performing a Fourier transform on an intensity distribution pattern measured by the light-receiving element array.

21. The polarization analysis method or polarization analysis system according to claim 18, wherein, by analyzing the shape of the intensity distribution pattern observed by the light-receiving element array, the value of the phase difference of the wavelength plate array used by the polarization analysis device is detected, and phase difference errors at the time of creation of the wavelength plate array are corrected.

22. A signal processing method, wherein, in order to remove the effects of scattered light and diffracted light from the boundary part of the respective regions of the wavelength plate array or polarizer array in the polarization analysis method or polarization analysis system according to claim 18, signals from a light-receiving element region that receives the scattered light and diffracted light among signals output by the light-receiving element array are removed.

23. A polarization analysis equipment, comprising:
(a) a first polarization analysis device, including:
a wavelength plate array having a plurality of regions in which phase differences supplied to transmitted light are uniform and optical axis directions are different; and
a polarizer array having a plurality of regions in which the directions of transmitted polarized waves are different,
wherein the wavelength plate array and the polarizer array are arranged to overlap one another, and a light-receiving element array is disposed so as to be capable of individually receiving light passed through a specified region of the wavelength plate and a region of the polarizer that overlaps the specified region; and
(b) a second polarization analysis device, including:
a wavelength plate array having a plurality of regions in which optical axis directions are uniform and phase differences of transmitted light are different; and
a polarizer array having a plurality of regions in which the directions of transmitted polarized waves are different,
wherein the wavelength plate array and the polarizer array are disposed to overlap one another, and a light-receiving element array is disposed so as to be capable of individually receiving light passed through a specified region of the wavelength plate and a region of the polarizer that overlaps the specified region; and
further wherein the light beam to be measured enters each of the first and the second analysis devices.

24. A polarization analysis method, wherein the polarization state of incident light is obtained by combining the methods of:
(a) a first polarization analysis method, wherein, in a polarization analysis device in which a wavelength plate array having a plurality of regions in which the phase differences are fixed and the optical axis directions are different and a polarizer array having a plurality of regions in which the directions of transmitted polarized waves are different are arranged to overlap one another so that the wavelength plate array is at the front and the polarizer array is at the rear and a light-receiving element array is disposed in two dimensions so as to be capable of individually receiving light passed through a certain region of the wavelength plate and a region of the polarizer that overlaps the certain region of the wavelength plate, the polarization state of incident light is obtained by using the characteristics that a two-dimensional intensity distribution pattern observed by means of the light-receiving element array is exhibited by only a DC component and at most three frequency components, wherein, by fitting or inserting sample values in use of the characteristics of a pattern shape in the neighborhood of a maximum point or a minimum point of an intensity distribution pattern observed by the light-receiving element array, the directions of the wavelength plate and polarizer that supply the ellipsometry quenching point or the flow amount minimum are calculated and the polarization state of incident light is obtained; and
(b) a second polarization analysis method, wherein, in a polarization analysis device in which a wavelength plate array having a plurality of regions in which the phase differences are fixed and the optical axis directions are different and a polarizer array having a plurality of regions in which the directions of transmitted polarized waves are different are arranged to overlap one another so that the wavelength plate array is at the front and the polarizer array is at the rear and a light-receiving element array is disposed in two dimensions so as to be capable of individually receiving light passed through a certain region of the wavelength plate and a region of the polarizer that overlaps the certain region of the wavelength plate, the polarization state of incident light is obtained by using the characteristics that a two-dimensional intensity distribution pattern observed by means of the light-receiving element array is exhibited by only a DC component and at most three frequency components, wherein the polarization state of incident light is obtained by performing a Fourier transform.

* * * * *